US009072893B2

(12) United States Patent
Chi Sing et al.

(10) Patent No.: US 9,072,893 B2
(45) Date of Patent: *Jul. 7, 2015

(54) EXPANDABLE BRACHYTHERAPY APPARATUS AND METHODS FOR USING THEM

(75) Inventors: Eduardo Chi Sing, Dana Point, CA (US); George D. Hermann, Portola Valley, CA (US); Dong S. Sutton, Pacifica, CA (US); Tommy G. Nguyen, Irvine, CA (US); Mark A. Ritchart, Murrieta, CA (US); Steven L. Gex, Monarch Beach, CA (US)

(73) Assignee: CIANNA MEDICAL, INC., Aliso Viejo, CA (US)

( * ) Notice: Subject to any disclaimer, the term of this patent is extended or adjusted under 35 U.S.C. 154(b) by 1308 days.

This patent is subject to a terminal disclaimer.

(21) Appl. No.: 11/757,231

(22) Filed: Jun. 1, 2007

(65) Prior Publication Data

US 2008/0221384 A1 Sep. 11, 2008

Related U.S. Application Data

(60) Provisional application No. 60/803,828, filed on Jun. 2, 2006.

(51) Int. Cl.
*A61M 36/12* (2006.01)
*A61N 5/10* (2006.01)

(52) U.S. Cl.
CPC ....... *A61N 5/1015* (2013.01); *A61N 2005/1018* (2013.01)

(58) Field of Classification Search
CPC .................. A61N 5/1001–5/1029; A61N 2005/1003–2005/1025
USPC ............. 600/1–8; 604/104–109, 164.03, 509; 378/65; 250/492.1–492.3
See application file for complete search history.

(56) References Cited

U.S. PATENT DOCUMENTS

| 3,060,924 A | 10/1962 | Rush |
| 3,750,653 A | 8/1973 | Simon |

(Continued)

FOREIGN PATENT DOCUMENTS

| DE | 3921291 | 1/1991 |
| DE | 3924291 | 1/1991 |

(Continued)

OTHER PUBLICATIONS

PCT International Search Report for PCT/US2007/070236 , Applicant: Cianna Medical, Inc., Forms PCT/ISA/220 and PCT/ISA/210, Mar. 5, 2008, 8 pages.

(Continued)

*Primary Examiner* — Catherine B Kuhlman
(74) *Attorney, Agent, or Firm* — William A. English; Vista IP Law Group LLP

(57) ABSTRACT

Apparatus for delivering brachytherapy to a target tissue region includes an elongate body including a proximal end, a distal end sized for introduction into a tissue tract and carrying a plurality of elongate members including pathways for receiving a source of radiation. The elongate members are movable between collapsed and expanded configurations. During use, a tract is created through tissue, and the elongate body carrying the elongate members is advanced through the tract into a target location with the elongate members in the collapsed configuration. The elongate members are directed to the expanded configuration at the target location, and radiation is delivered to treat tissue at the target location, e.g., by introducing one or more radiation sources along the pathways.

51 Claims, 64 Drawing Sheets

(56) References Cited

U.S. PATENT DOCUMENTS

| | | |
|---|---|---|
| 3,968,803 A | 7/1976 | Hyman |
| 4,427,005 A | 1/1984 | Tener |
| 4,580,561 A | 4/1986 | Williamson |
| 4,706,652 A | 11/1987 | Horowitz |
| 4,714,074 A | 12/1987 | Rey et al. |
| 4,798,212 A | 1/1989 | Arana |
| 4,936,823 A | 6/1990 | Colvin et al. |
| 4,957,476 A | 9/1990 | Cano |
| 4,976,680 A | 12/1990 | Hayman et al. |
| 5,056,523 A | 10/1991 | Hotchkiss, Jr. et al. |
| 5,106,360 A | 4/1992 | Ishiwara et al. |
| 5,152,741 A | 10/1992 | Farnio |
| 5,235,966 A | 8/1993 | Jamner |
| 5,242,372 A | 9/1993 | Carol |
| 5,279,565 A | 1/1994 | Klein et al. |
| 5,302,168 A | 4/1994 | Hess |
| 5,336,178 A * | 8/1994 | Kaplan et al. .............. 604/509 |
| 5,354,257 A | 10/1994 | Roubin et al. |
| 5,411,466 A | 5/1995 | Hess |
| 5,423,747 A | 6/1995 | Amano |
| 5,429,605 A | 7/1995 | Richling et al. |
| 5,484,384 A | 1/1996 | Fearnot |
| 5,503,613 A | 4/1996 | Weinberger |
| 5,509,900 A | 4/1996 | Kirkman |
| 5,538,502 A | 7/1996 | Johnstone |
| 5,540,659 A | 7/1996 | Teirstein |
| 5,611,767 A | 3/1997 | Williams |
| 5,653,683 A * | 8/1997 | D'Andrea .................... 604/21 |
| 5,678,572 A | 10/1997 | Shaw et al. |
| 5,707,332 A | 1/1998 | Weinberger |
| 5,713,828 A | 2/1998 | Coniglione |
| 5,720,717 A | 2/1998 | D'Andrea |
| 5,730,698 A | 3/1998 | Fischell et al. |
| 5,782,740 A | 7/1998 | Schneiderman |
| 5,840,008 A | 11/1998 | Klein et al. |
| 5,843,163 A | 12/1998 | Wall |
| 5,851,171 A | 12/1998 | Gasson |
| 5,863,284 A * | 1/1999 | Klein ......................... 600/3 |
| 5,882,291 A | 3/1999 | Bradshaw et al. |
| 5,891,091 A | 4/1999 | Teirstein |
| 5,910,102 A | 6/1999 | Hastings |
| 5,913,813 A | 6/1999 | Williams et al. |
| 5,916,143 A | 6/1999 | Apple et al. |
| 5,931,774 A | 8/1999 | Williams et al. |
| 5,938,582 A | 8/1999 | Ciamacco, Jr. et al. |
| 5,942,209 A | 8/1999 | Leavitt et al. |
| 5,976,106 A | 11/1999 | Verin et al. |
| 6,013,019 A | 1/2000 | Fischell et al. |
| 6,022,308 A | 2/2000 | Williams |
| 6,030,333 A | 2/2000 | Sioshansi et al. |
| 6,033,357 A | 3/2000 | Ciezki et al. |
| 6,036,632 A | 3/2000 | Whitmore et al. |
| 6,056,722 A | 5/2000 | Jayaraman |
| 6,059,752 A | 5/2000 | Segal |
| 6,071,263 A | 6/2000 | Kirkman |
| 6,074,339 A | 6/2000 | Ganbale et al. |
| 6,083,148 A | 7/2000 | Williams |
| 6,117,064 A | 9/2000 | Apple et al. |
| 6,159,139 A | 12/2000 | Chiu |
| 6,159,141 A | 12/2000 | Apple et al. |
| 6,176,821 B1 | 1/2001 | Crocker et al. |
| 6,179,766 B1 | 1/2001 | Dickerson |
| 6,196,996 B1 | 3/2001 | Teirstein |
| 6,200,256 B1 | 3/2001 | Weinberger |
| 6,200,257 B1 | 3/2001 | Winkler |
| 6,213,976 B1 | 4/2001 | Trerotola |
| 6,217,585 B1 | 4/2001 | Houser et al. |
| 6,221,003 B1 | 4/2001 | Sierocuk et al. |
| 6,221,030 B1 | 4/2001 | Avaltroni |
| 6,234,951 B1 | 5/2001 | Hastings |
| 6,238,374 B1 | 5/2001 | Winkler |
| 6,258,099 B1 | 7/2001 | Mareiro et al. |
| 6,261,320 B1 | 7/2001 | Tam et al. |
| 6,264,599 B1 | 7/2001 | Slater et al. |
| 6,264,631 B1 | 7/2001 | Willis et al. |
| 6,267,775 B1 | 7/2001 | Clerc et al. |
| 6,287,249 B1 | 9/2001 | Tam et al. |
| 6,338,709 B1 | 1/2002 | Geoffrion |
| 6,358,195 B1 | 3/2002 | Green et al. |
| 6,371,904 B1 | 4/2002 | Sirimanne et al. |
| 6,413,204 B1 | 7/2002 | Winkler et al. |
| 6,458,069 B1 | 10/2002 | Tam et al. |
| 6,482,142 B1 | 11/2002 | Winkler et al. |
| 6,482,178 B1 | 11/2002 | Andrews et al. |
| 6,494,824 B1 | 12/2002 | Apple et al. |
| 6,506,145 B1 | 1/2003 | Bradshaw et al. |
| 6,508,784 B1 | 1/2003 | Shu |
| 6,527,692 B1 | 3/2003 | Weinberger |
| 6,527,693 B2 | 3/2003 | Munro, III et al. |
| 6,540,656 B2 | 4/2003 | Fontayne et al. |
| 6,540,734 B2 | 4/2003 | Chiu et al. |
| 6,554,757 B1 | 4/2003 | Geitz |
| 6,582,353 B1 | 6/2003 | Hastings et al. |
| 6,589,158 B2 | 7/2003 | Winkler |
| 6,592,548 B2 | 7/2003 | Jayaraman |
| 6,607,476 B1 * | 8/2003 | Barnhart ..................... 600/3 |
| 6,607,478 B2 | 8/2003 | Williams |
| 6,638,206 B2 | 10/2003 | Green et al. |
| 6,641,518 B2 | 11/2003 | Wolfson et al. |
| 6,645,135 B1 | 11/2003 | Bhat |
| 6,648,811 B2 | 11/2003 | Sierocuk et al. |
| 6,659,933 B2 | 12/2003 | Asano |
| 6,673,006 B2 | 1/2004 | Winkler |
| 6,676,667 B2 | 1/2004 | Mareiro et al. |
| 6,685,619 B2 | 2/2004 | Halpern et al. |
| 6,692,460 B1 | 2/2004 | Jayaraman |
| 6,699,170 B1 | 3/2004 | Crocker et al. |
| 6,719,805 B1 | 4/2004 | Ahern |
| 6,746,465 B2 | 6/2004 | Diederich et al. |
| 6,752,752 B2 | 6/2004 | Geitz |
| 6,910,999 B2 | 6/2005 | Chin et al. |
| 6,923,754 B2 | 8/2005 | Lubock |
| 6,955,641 B2 | 10/2005 | Lubock |
| 7,041,047 B2 | 5/2006 | Gellman et al. |
| 7,056,276 B2 | 6/2006 | Nakano et al. |
| 7,357,770 B1 | 4/2008 | Cutrer et al. |
| 2001/0007071 A1 | 7/2001 | Koblish |
| 2002/0016583 A1 | 2/2002 | Cragg |
| 2002/0032359 A1 | 3/2002 | Geoffrion et al. |
| 2002/0165427 A1 | 11/2002 | Yachia et al. |
| 2003/0069533 A1 | 4/2003 | Kakutani et al. |
| 2003/0092957 A1 | 5/2003 | Scott et al. |
| 2003/0114878 A1 * | 6/2003 | Diederich et al. ............. 606/192 |
| 2003/0158515 A1 | 8/2003 | Gonzalez et al. |
| 2003/0163017 A1 | 8/2003 | Tam et al. |
| 2003/0236443 A1 | 12/2003 | Cespedes et al. |
| 2004/0006305 A1 | 1/2004 | Hebert et al. |
| 2004/0068231 A1 | 4/2004 | Blondeau |
| 2004/0087828 A1 | 5/2004 | Green et al. |
| 2004/0116767 A1 | 6/2004 | Lebovic et al. |
| 2004/0127765 A1 | 7/2004 | Seiler et al. |
| 2004/0260142 A1 | 12/2004 | Lovoi |
| 2005/0061533 A1 | 3/2005 | Lovoi |
| 2005/0075662 A1 | 4/2005 | Pederson et al. |
| 2005/0080313 A1 * | 4/2005 | Stewart et al. ..................... 600/3 |
| 2005/0090845 A1 | 4/2005 | Boyd |
| 2005/0096647 A1 | 5/2005 | Steinke et al. |
| 2005/0101823 A1 | 5/2005 | Linares et al. |
| 2005/0101860 A1 | 5/2005 | Patrick et al. |
| 2005/0124843 A1 | 6/2005 | Singh |
| 2005/0182286 A1 | 8/2005 | Lubock |
| 2005/0240074 A1 | 10/2005 | Lubock |
| 2006/0015166 A1 | 1/2006 | Kindlein et al. |
| 2006/0020156 A1 | 1/2006 | Shukla |
| 2006/0094923 A1 | 5/2006 | Mate |
| 2006/0100475 A1 * | 5/2006 | White et al. ..................... 600/3 |
| 2006/0116546 A1 | 6/2006 | Eng |
| 2006/0173233 A1 | 8/2006 | Lovoi |
| 2006/0173235 A1 | 8/2006 | Lim et al. |
| 2006/0184192 A1 | 8/2006 | Markworth et al. |
| 2006/0199990 A1 | 9/2006 | Rioux et al. |
| 2006/0235365 A1 | 10/2006 | Terwilliger et al. |
| 2006/0258895 A1 | 11/2006 | Maschke |
| 2007/0106108 A1 * | 5/2007 | Hermann et al. ..................... 600/7 |

(56) References Cited

U.S. PATENT DOCUMENTS

| | | |
|---|---|---|
| 2007/0167664 A1 | 7/2007 | Hermann et al. |
| 2007/0167667 A1 | 7/2007 | Lubock et al. |
| 2007/0191668 A1 | 8/2007 | Lubock et al. |
| 2007/0270627 A1* | 11/2007 | Cutrer et al. ............ 600/7 |

FOREIGN PATENT DOCUMENTS

| | | |
|---|---|---|
| EP | 0318447 B1 | 9/1994 |
| EP | 0390528 B1 | 1/1997 |
| EP | 0775505 | 5/1997 |
| EP | 0536888 B1 | 1/1998 |
| EP | 0906769 | 4/1999 |
| EP | 0955071 | 11/1999 |
| EP | 0884977 B1 | 4/2003 |
| EP | 0782410 B1 | 12/2003 |
| EP | 0955071 | 2/2004 |
| EP | 1402922 | 3/2004 |
| EP | 1405600 | 4/2004 |
| EP | 0808129 B1 | 5/2004 |
| EP | 1428477 | 6/2004 |
| EP | 1568397 | 8/2005 |
| JP | 2003116982 A | 4/2003 |
| JP | 2004510685 A | 4/2004 |
| WO | 00/59378 | 10/2000 |
| WO | 01/95808 | 12/2001 |
| WO | 03/077768 | 9/2003 |
| WO | 03/079907 | 10/2003 |
| WO | 2005037363 | 4/2005 |

OTHER PUBLICATIONS

PCT Written Opinion for PCT/US2007/070326, Applicant: Cianna Medical, Inc., Forms PCT/ISA/237, Mar. 5, 2008, 13 pages.

Office Actions and Applicant Responses for related U.S. Appl. No. 11/276,851 dated Feb. 4, 2009 to Apr. 14, 2009, 51 pages.

Australian Patent Office Action and Response from related Australian Application No. 2007256766, Sep. 30, 2010 to Aug. 26, 2011, 18 pages.

European Patent Office Action and Response from related European Application No. 07798023.3, Apr. 27, 2009 to Oct. 29, 2009, 11 pages.

Japanese Patent Office Action and translation from related Japanese Application No. 2009-513474, May 8, 2012, 11 pages.

* cited by examiner

Fig. 3A
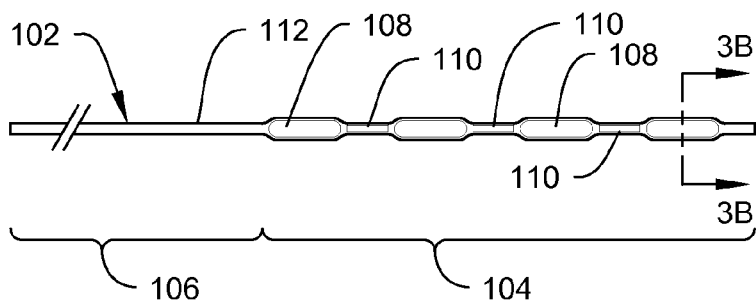
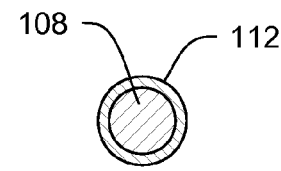
Fig. 3B
Fig. 4A
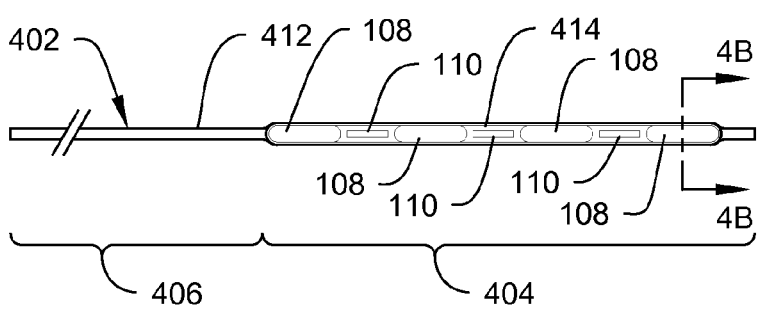
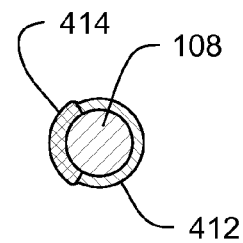
Fig. 4B
Fig. 5A
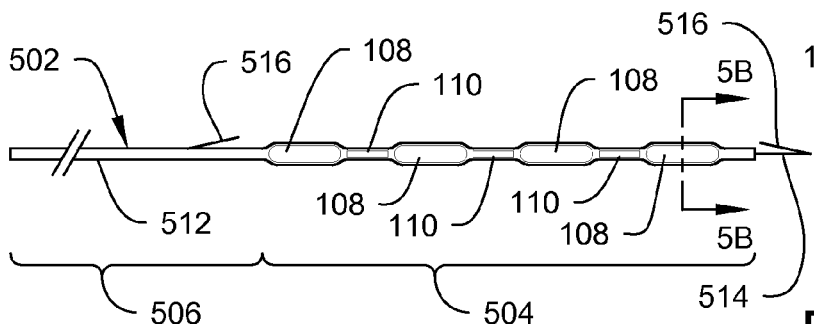
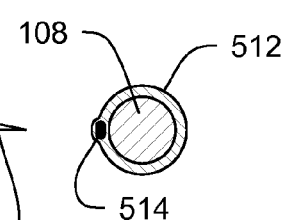
Fig. 5B
Fig. 5C
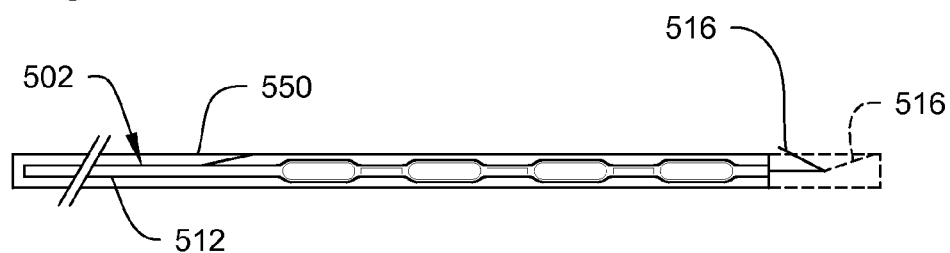

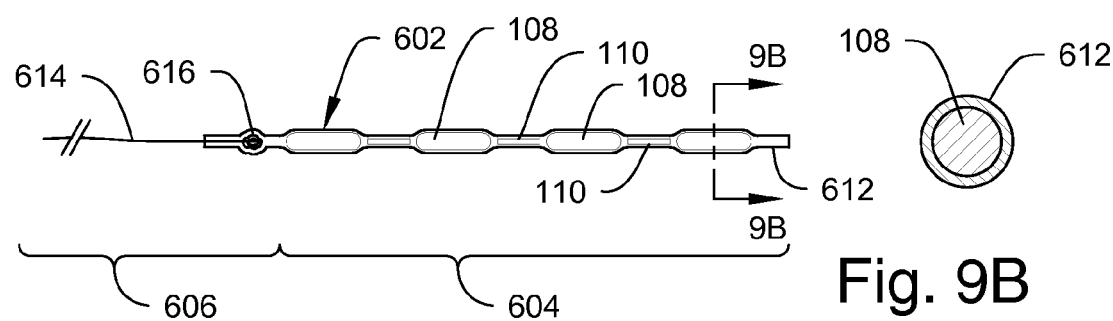
Fig. 9A
Fig. 9B
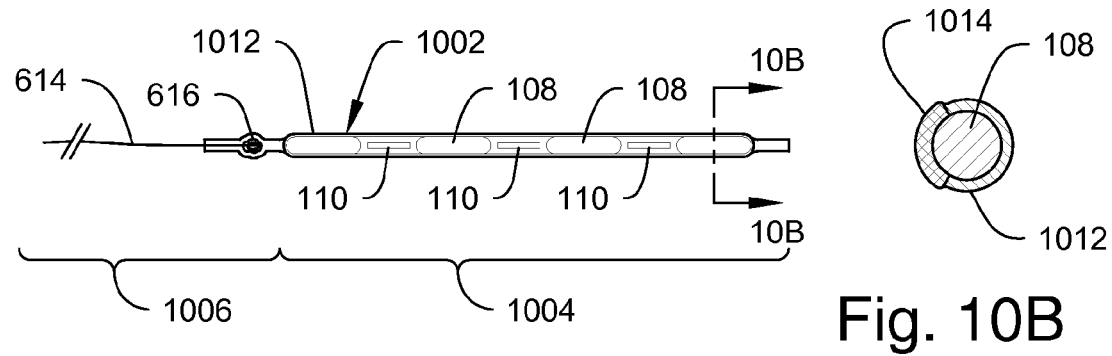
Fig. 10A
Fig. 10B
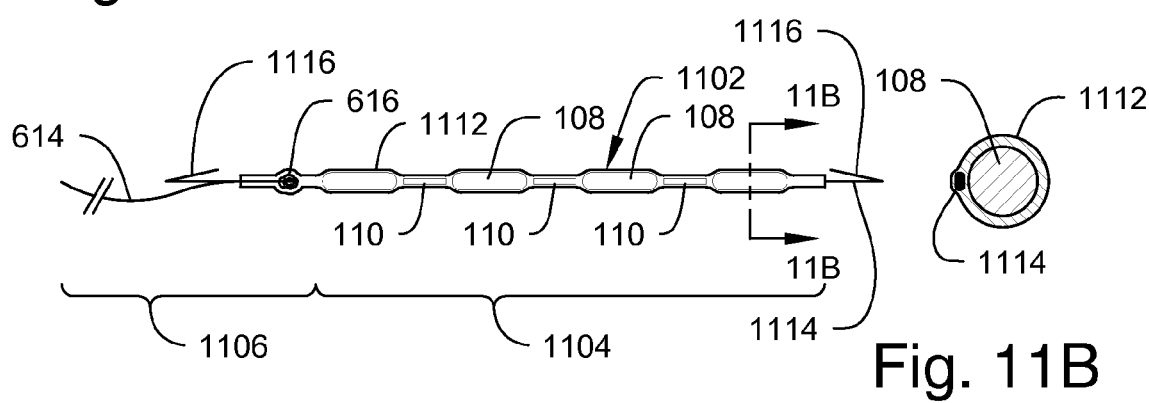
Fig. 11A
Fig. 11B

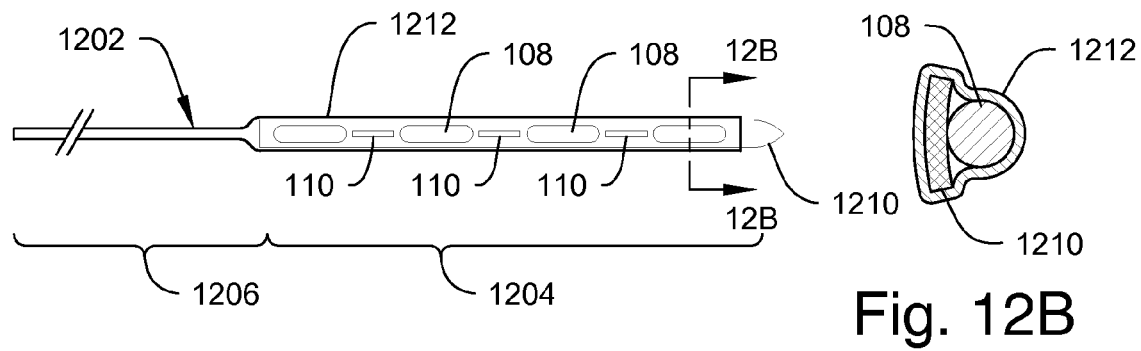
Fig. 12A
Fig. 12B
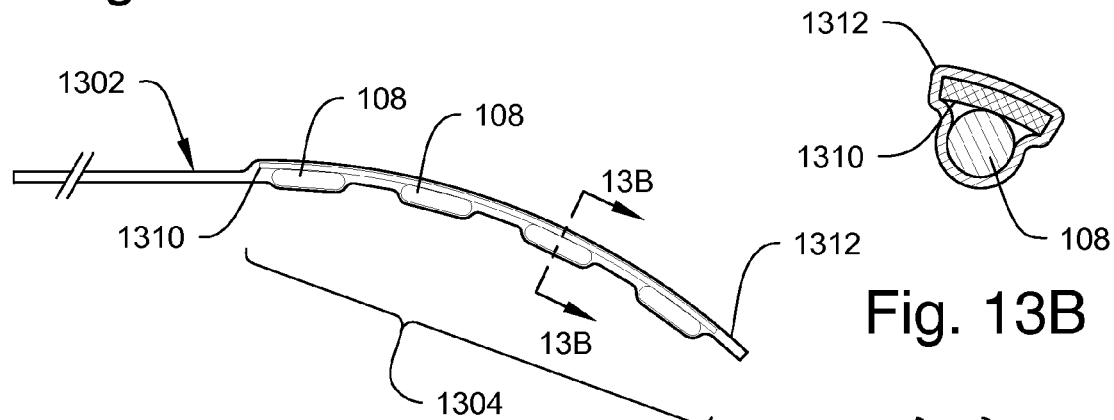
Fig. 13A
Fig. 13B
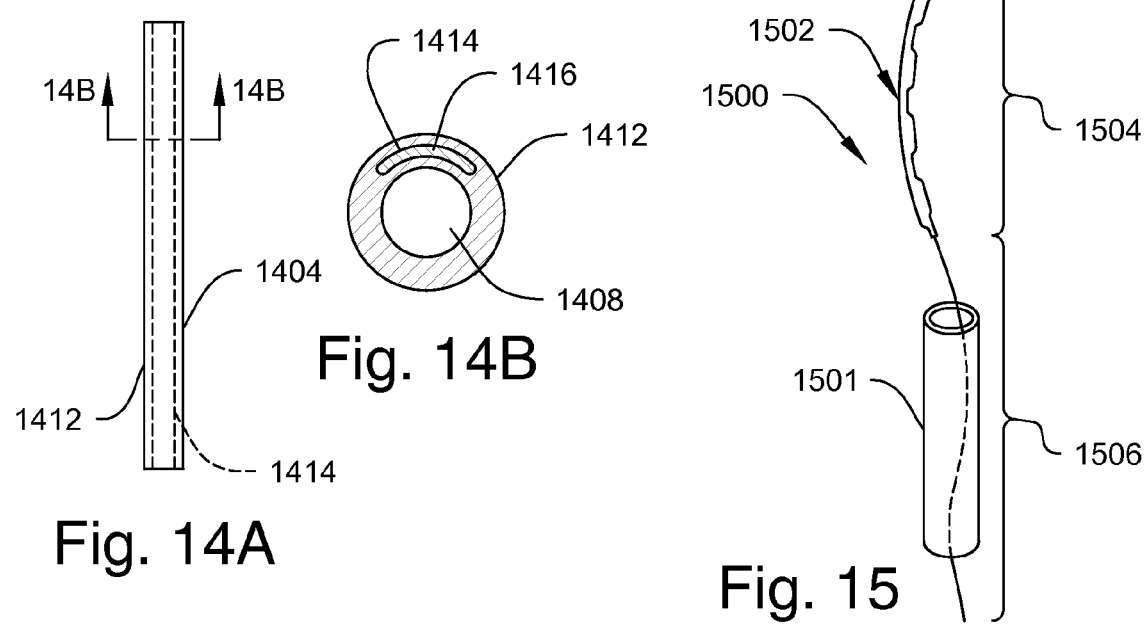
Fig. 14A
Fig. 14B
Fig. 15

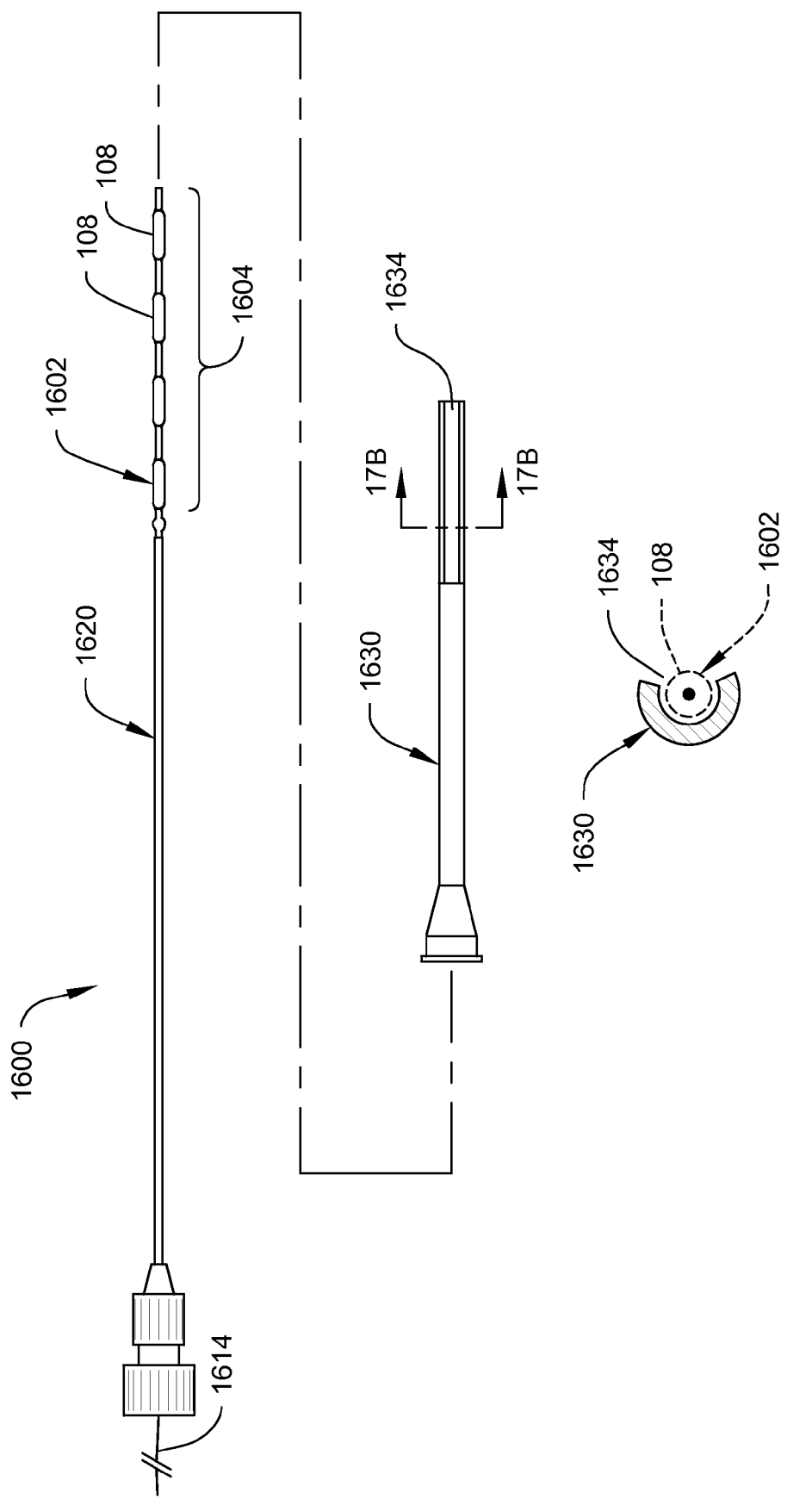

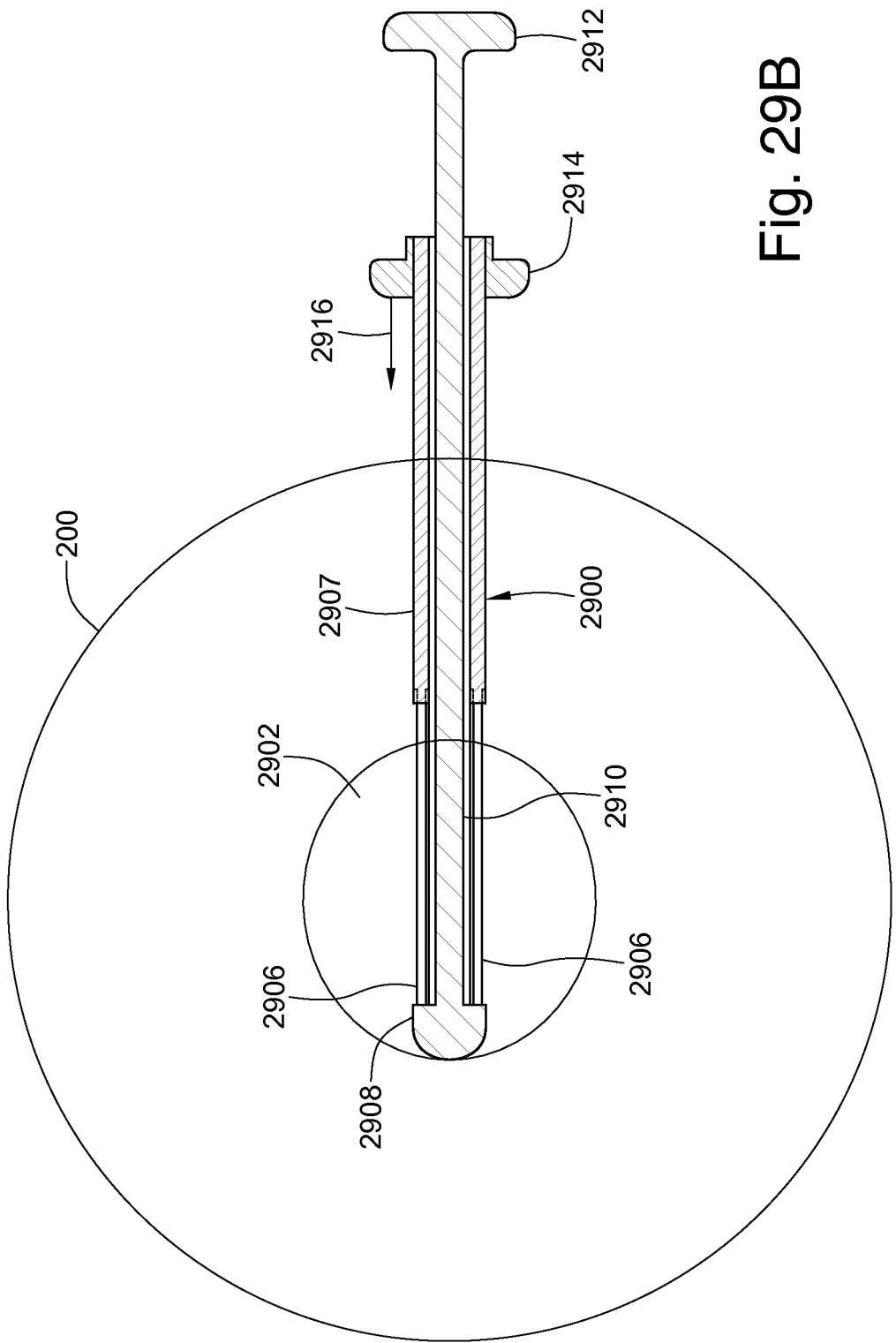

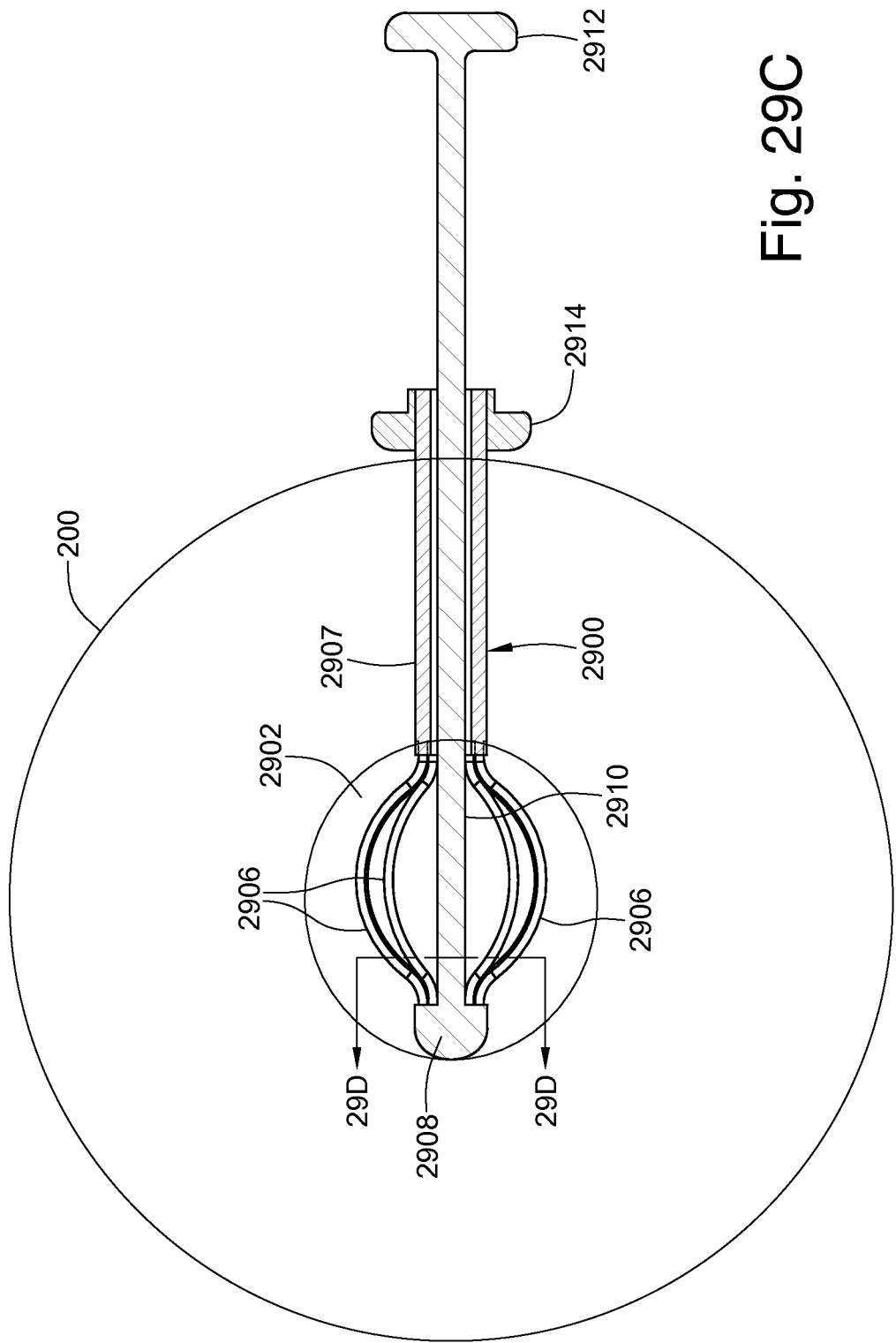

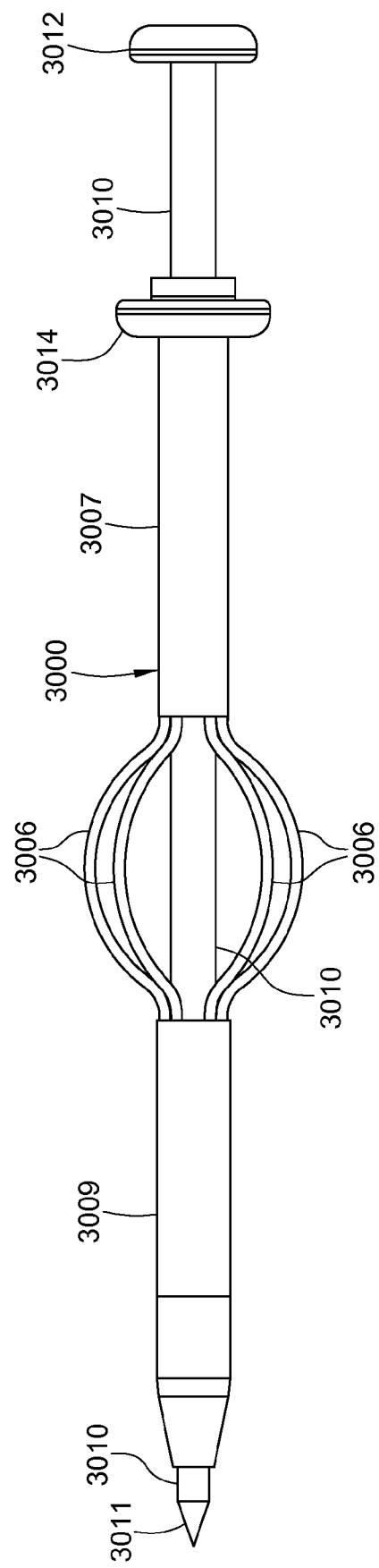

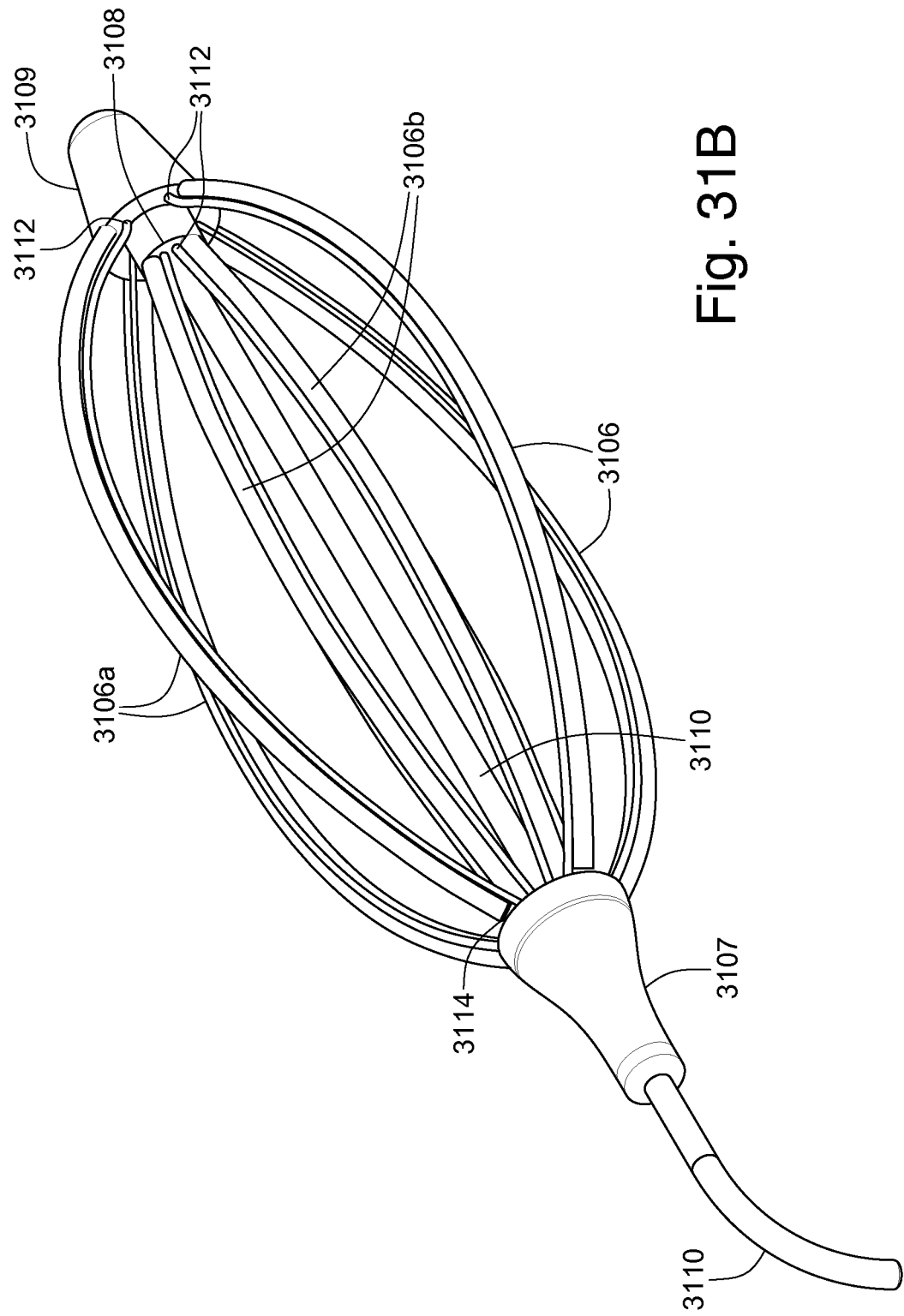

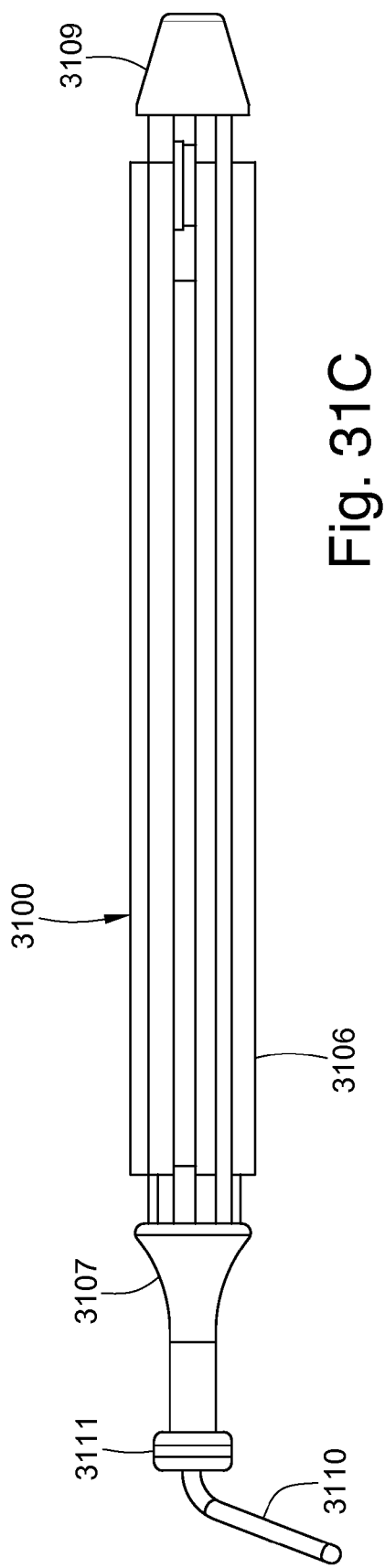
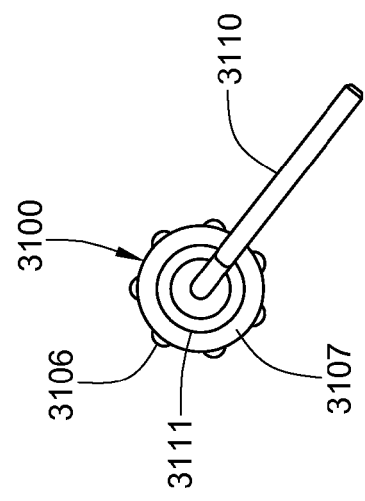
Fig. 31C
Fig. 31D

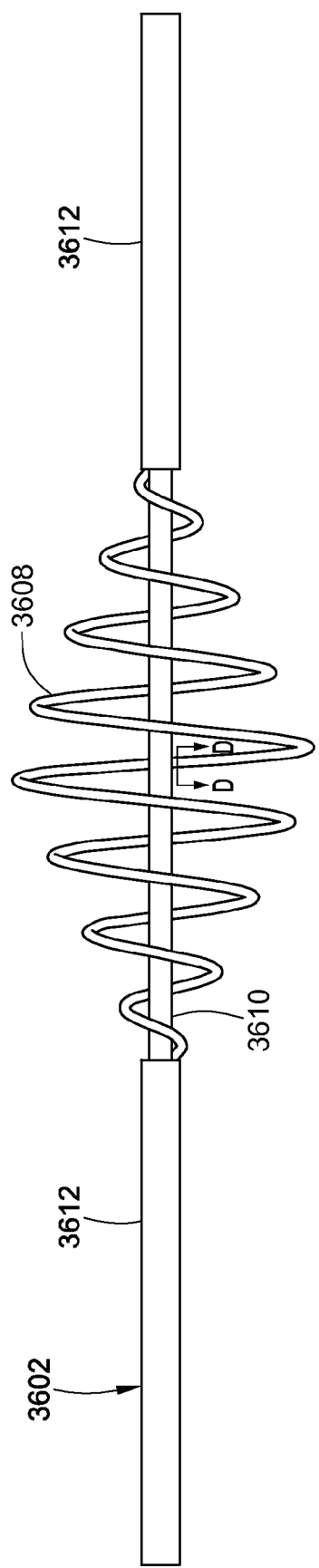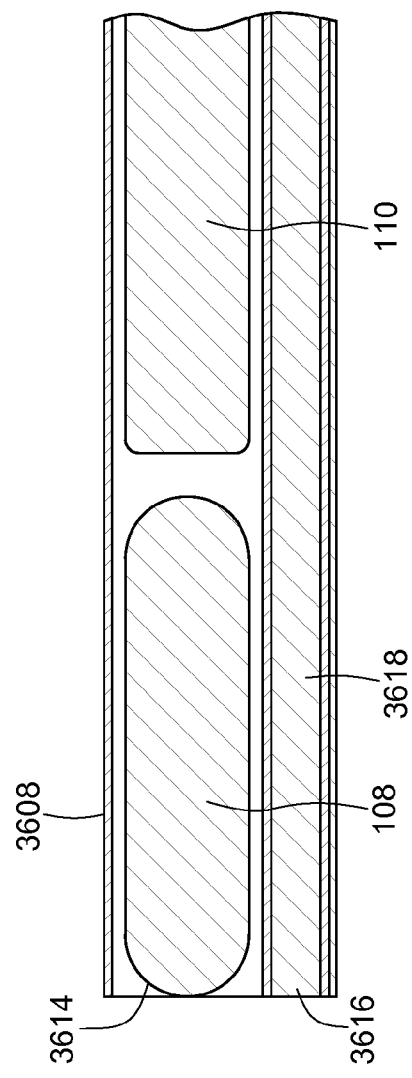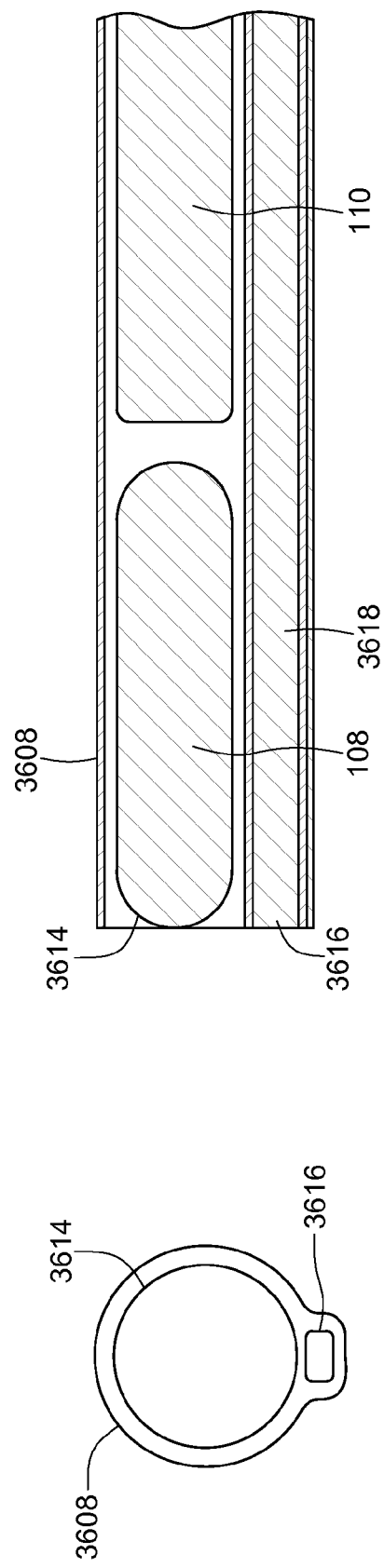

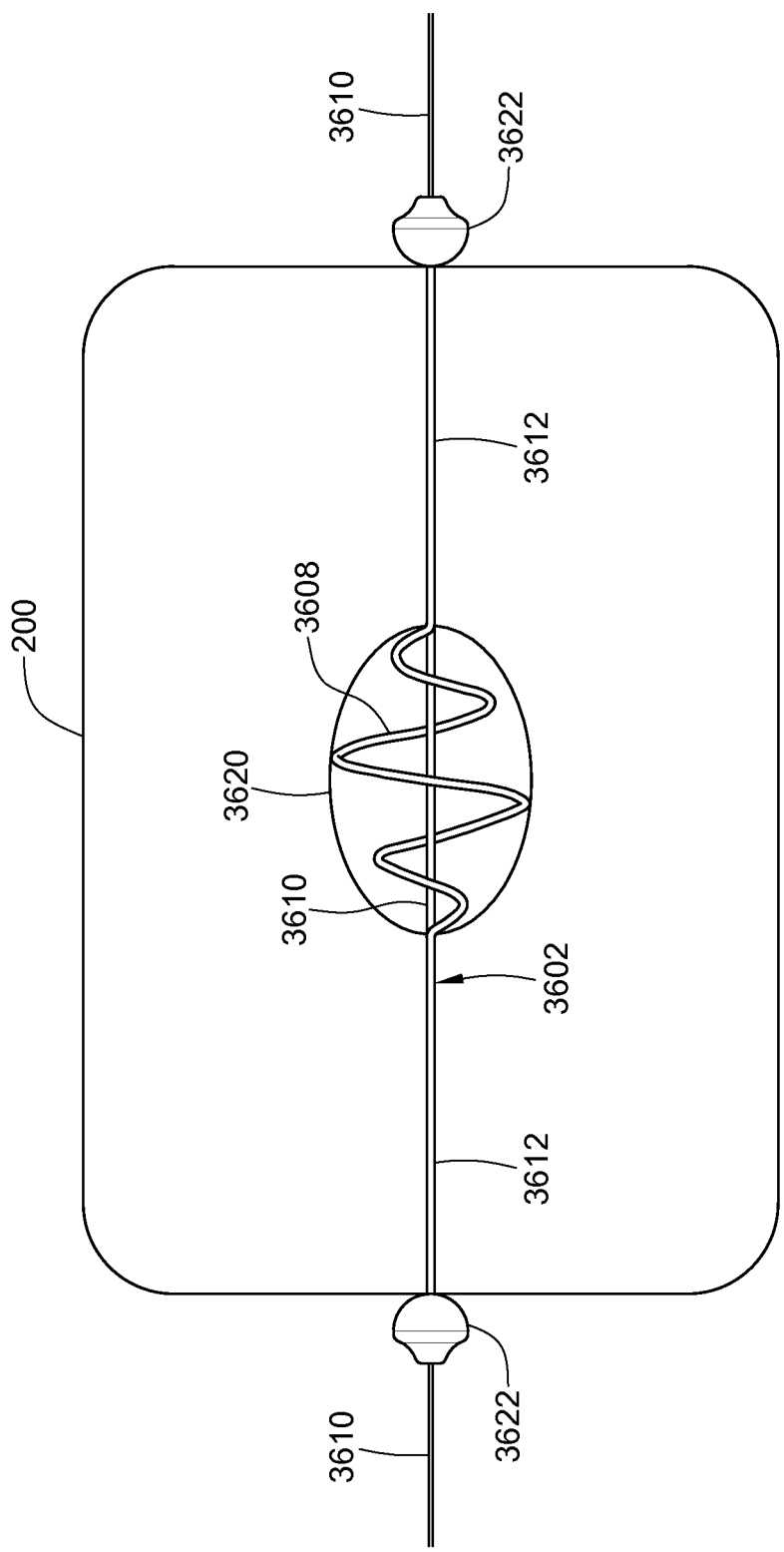

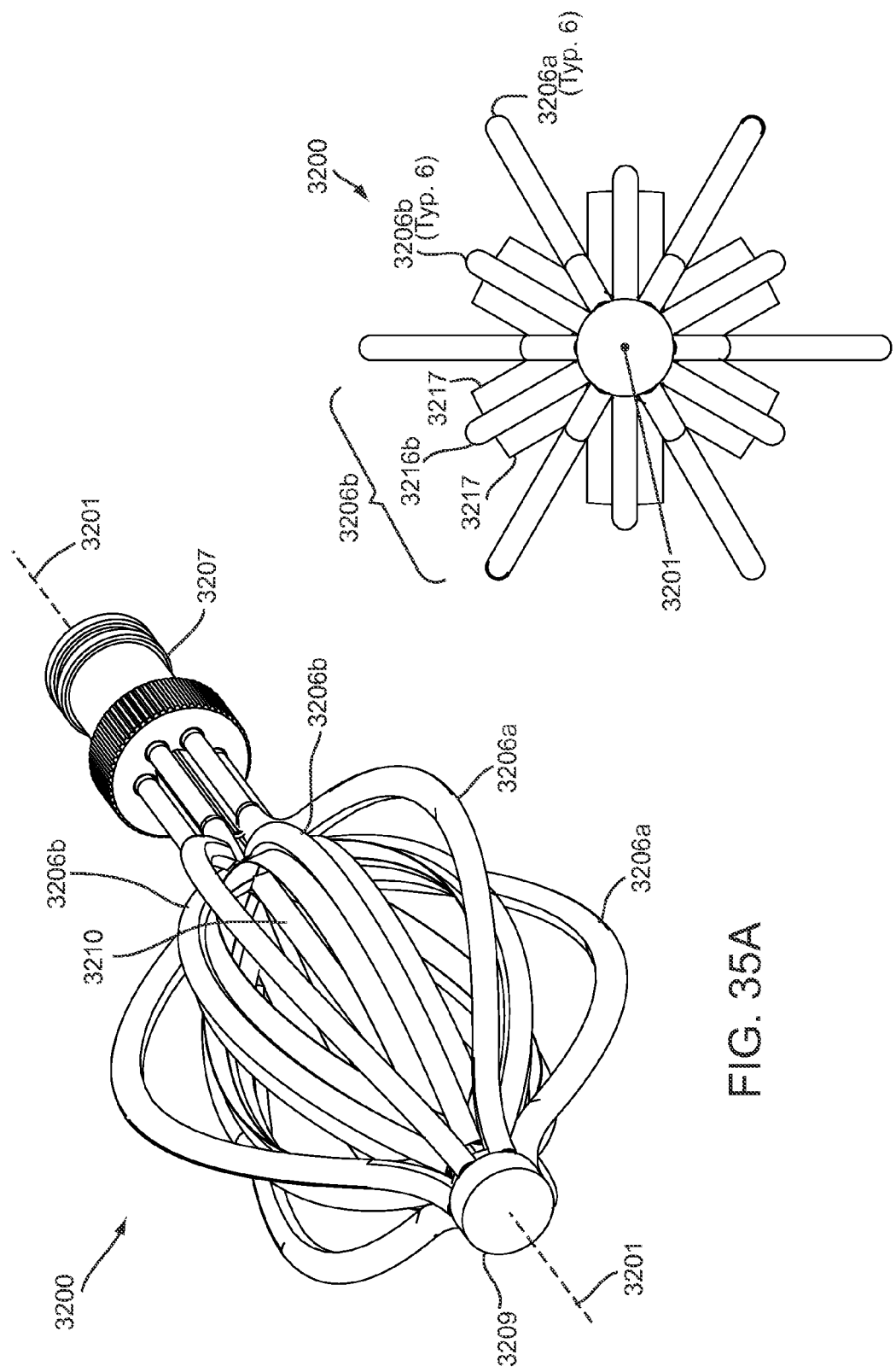

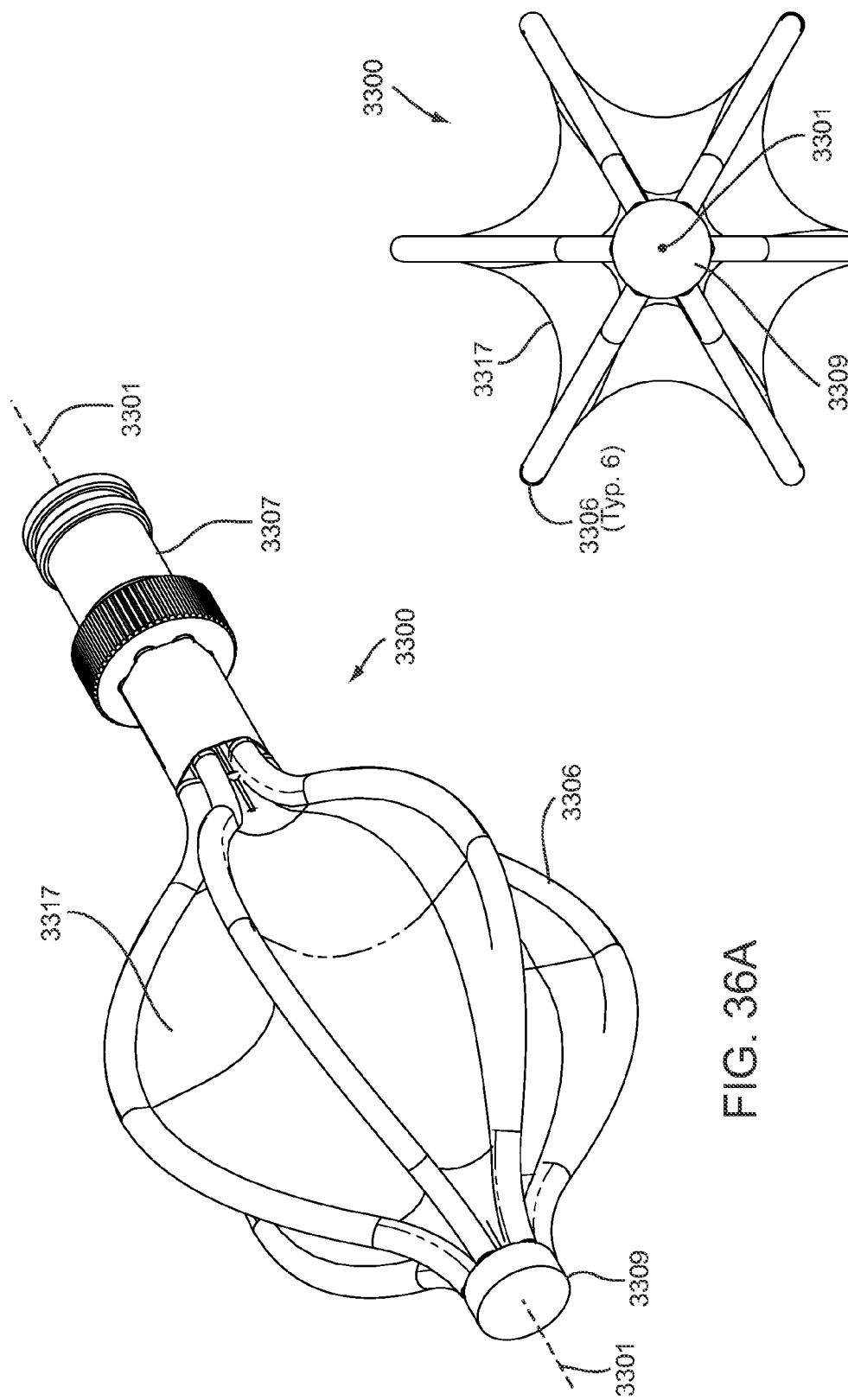

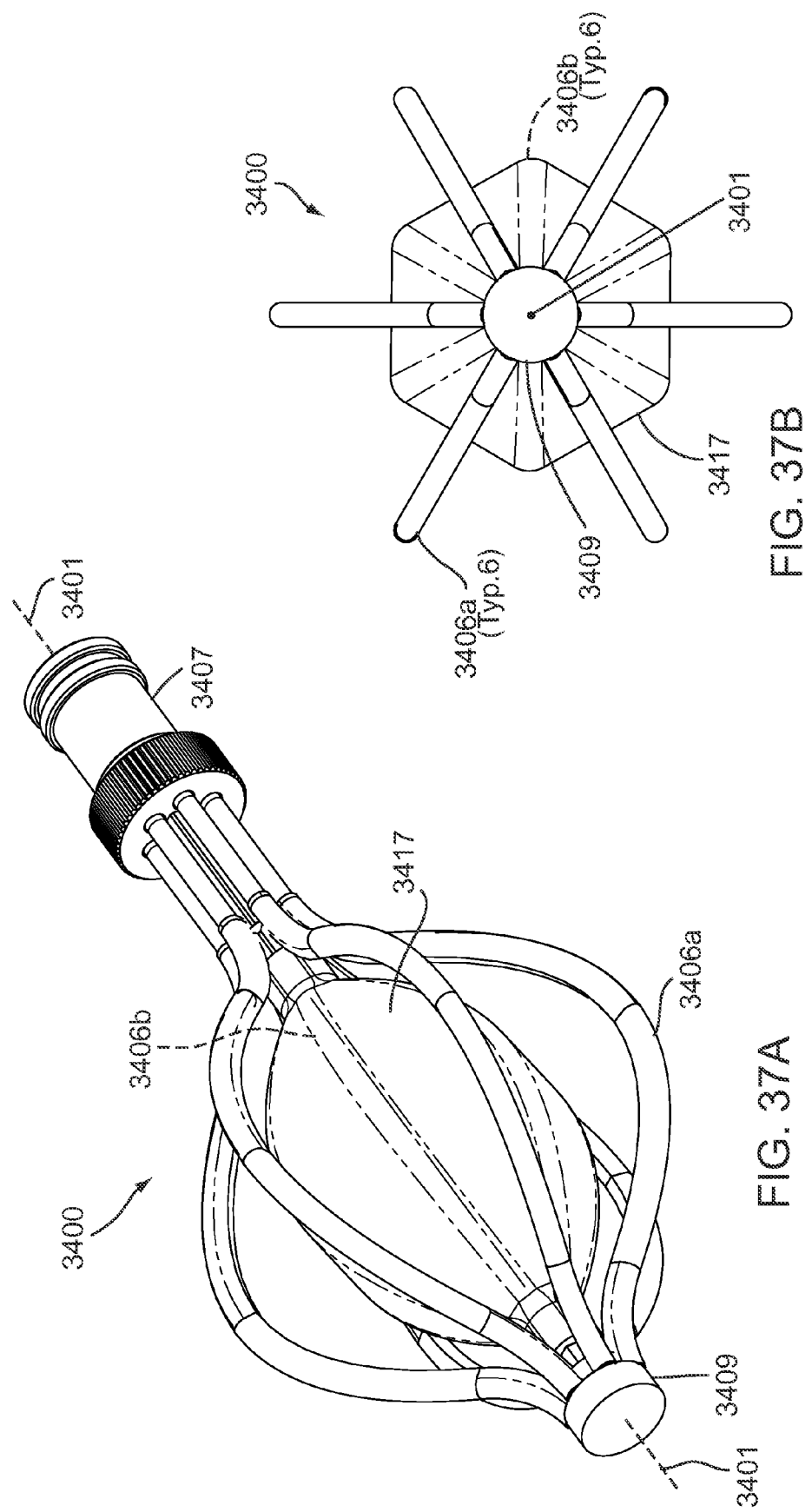

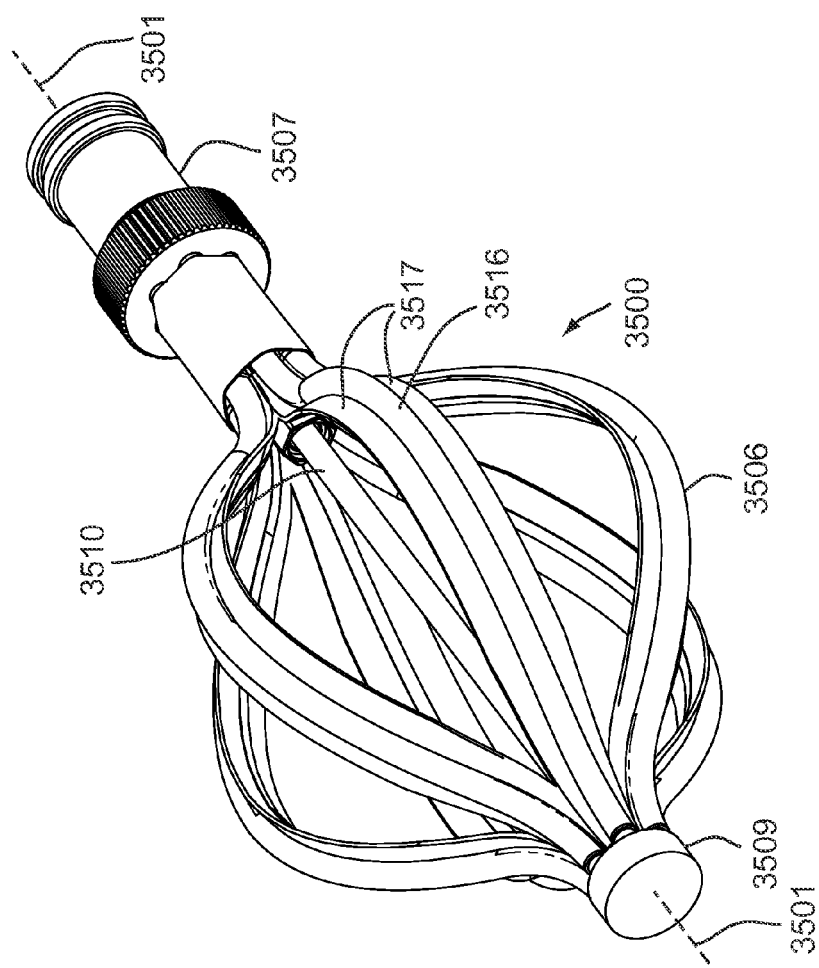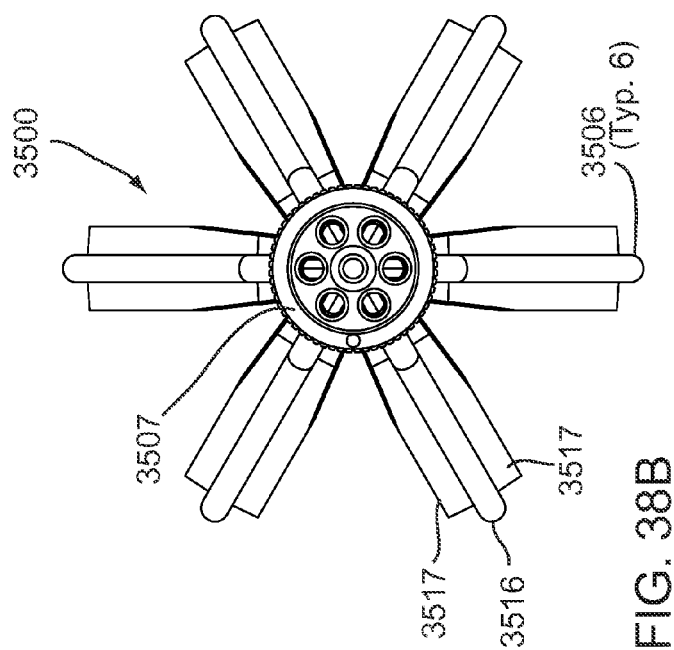
FIG. 38A
FIG. 38B

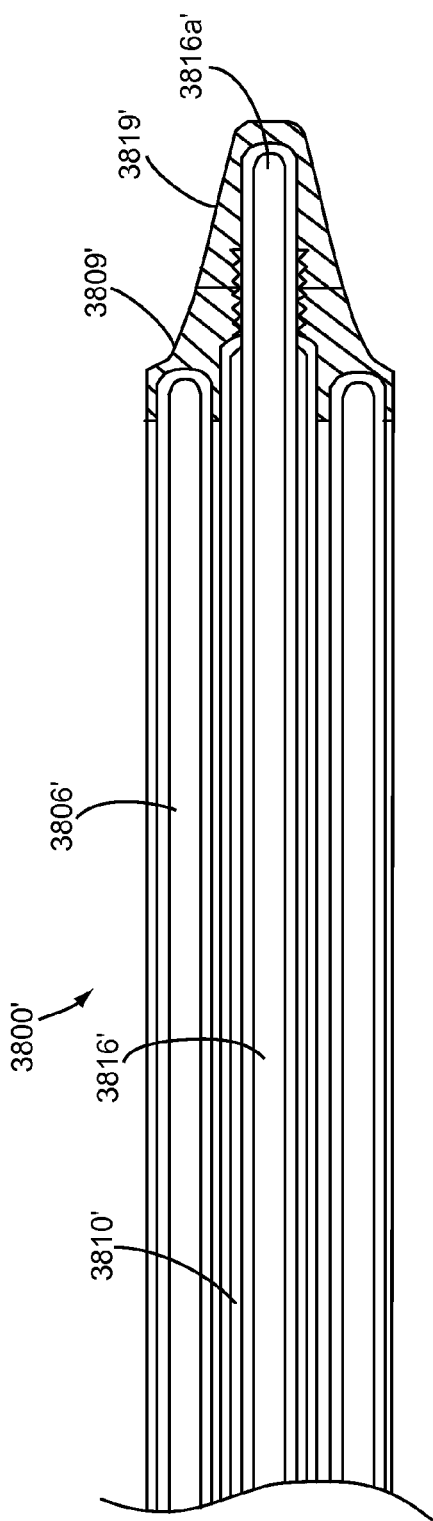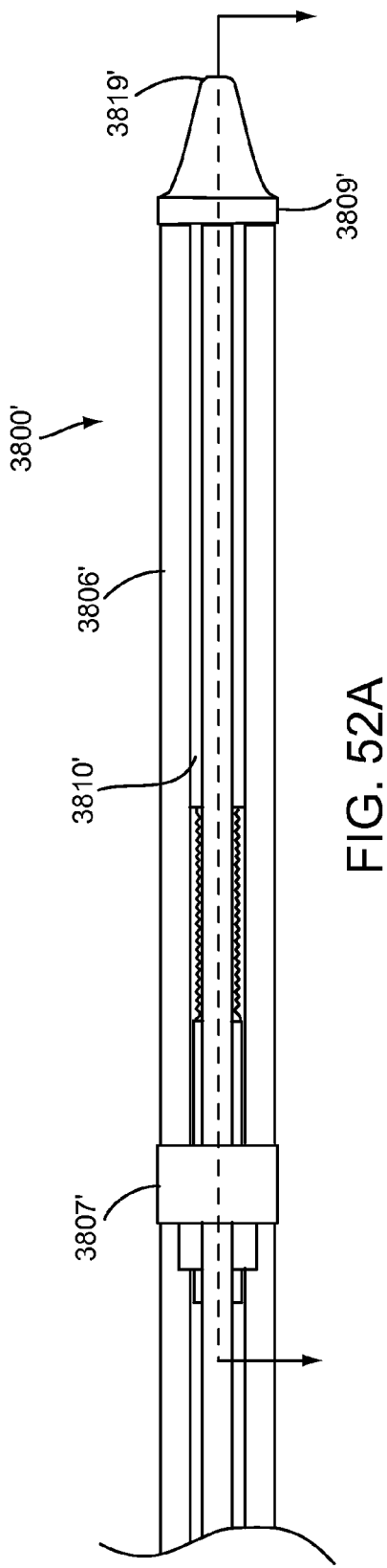
FIG. 52B
FIG. 52A

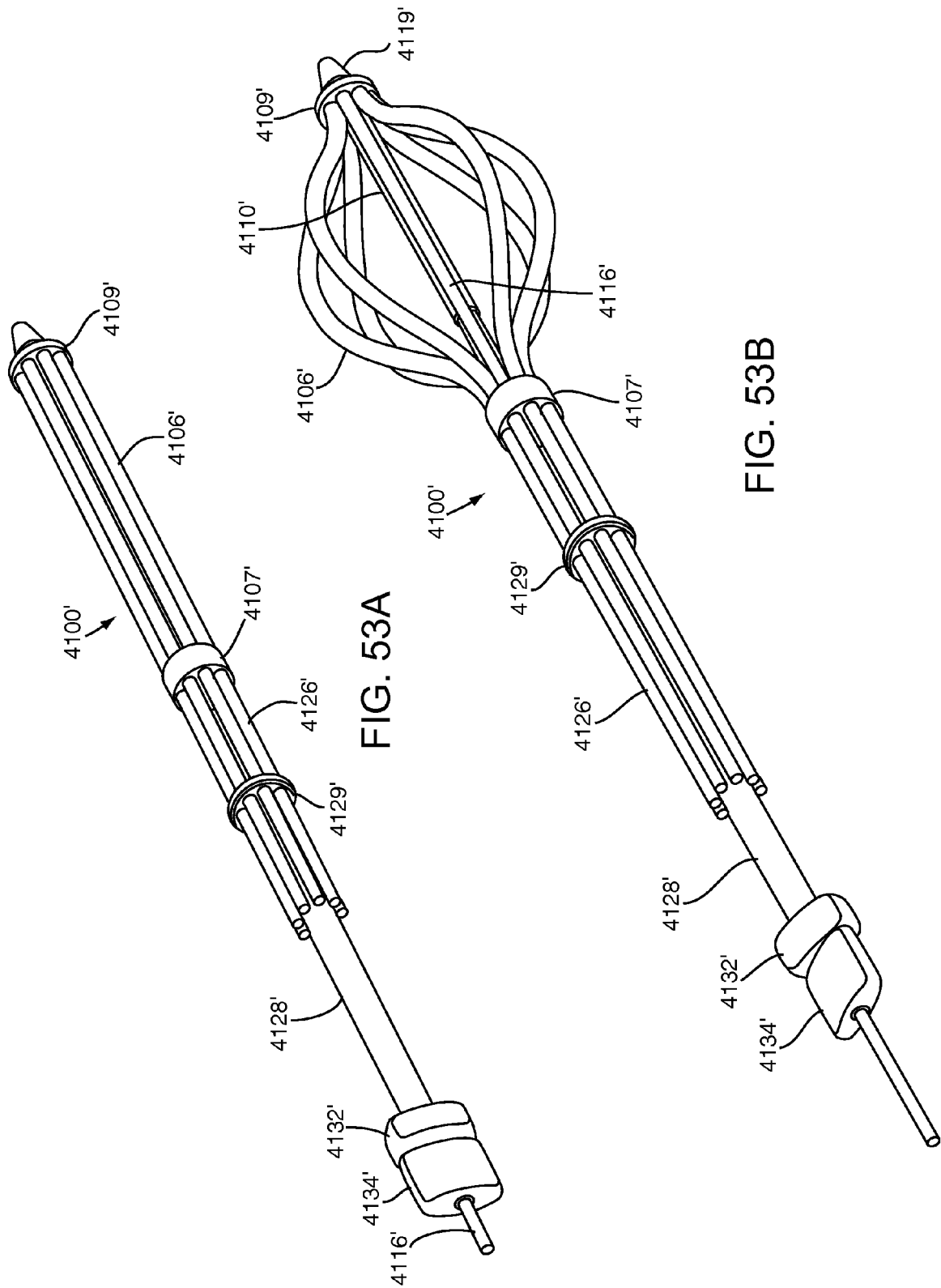

EXPANDABLE BRACHYTHERAPY APPARATUS AND METHODS FOR USING THEM

This application claims benefit of provisional application Ser. No. 60/803,828, filed Jun. 2, 2006, the entire disclosure of which is expressly incorporated by reference herein.

FIELD OF THE INVENTION

The present invention relates generally to apparatus, methods, and systems for providing brachytherapy to a human or other mammalian body, and more particularly to expandable apparatus for performing brachytherapy treatment within tissue, e.g., within breast tissue and/or within a body cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy places a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which may lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they may be provided in a standardized size of cylindrically shaped capsules that are approximately the size of a grain of rice, e.g., about 0.8 millimeter in diameter and about 4.5 millimeters in length, and are often referred to as "seeds."

LDR seeds are often delivered through needles using a guide template. The guide template may include a matrix of holes that guide the longitudinal advancement of the needles to ensure their proper position relative to the target tissue. Once the needles are properly located in the target tissue, the seeds may be deposited along the longitudinal axis of each needle, after which the needles may be withdrawn.

While effective, current brachytherapy implementations have potential drawbacks. For example, the LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus and methods for delivering brachytherapy to a localized target tissue region. While the invention is useful in treating most any area of the body, it offers particular advantages in the treatment of breast tissue, e.g., breast tumors or lumpectomy cavities. For example, the invention may be used to place and remove a localized radiation source for both neoadjuvant and post-excisional treatment.

Exemplary embodiments of the invention are directed to brachytherapy devices and apparatus. Such devices and apparatus are capable of delivering brachytherapy treatment to a target region (e.g., breast tissue region). Other embodiments are directed to delivering brachytherapy devices to the target region. Systems and methods for delivering brachytherapy to the target region are also provided.

In accordance with one embodiment, a brachytherapy treatment apparatus is provided that includes an elongate body including a proximal end and a distal end sized for introduction into a tract through tissue. A plurality of elongate members may be provided on the distal end including pathways for receiving a source of radiation therealong, the elongate members being movable from a collapsed configuration for introduction through a tissue tract to a target location, and an expanded configuration. A source of radiation may be introduceable along the pathways for delivering radiation to the target location.

In accordance with another embodiment, a method is provided for brachytherapy treatment of tissue within a body that includes creating a tract through tissue to a target location comprising a cavity, and advancing an elongate body carrying a plurality of elongate members through the tract into the target location with the elongate members in a collapsed configuration. The elongate members may be directed to an expanded configuration at the target location to position the elongate members away from a central axis such that tissue in the target region (e.g., surrounding the cavity) extends between at least a portion of adjacent elongate members, and radiation may be delivered to the target location to treat tissue at the target location.

The above summary is not intended to describe each embodiment or every implementation of the present invention. Rather, a more complete understanding of the invention will become apparent and appreciated by reference to the following detailed description and claims in view of the accompanying drawing.

BRIEF DESCRIPTION OF THE DRAWINGS

FIG. 3A is a side view of a first exemplary embodiment of a brachytherapy device;

FIG. 3B is a cross-sectional view of the device of FIG. 3A, taken along line 3B-3B;

FIG. 4A is a side view of a second exemplary embodiment of a brachytherapy device;

FIG. 4B is a cross-sectional view of the device of FIG. 4A, taken along line 4B-4B;

FIG. 5A is a side view of a third exemplary embodiment of a brachytherapy device;

FIG. 5B is a cross-sectional view of the device of FIG. 5A, taken along line 5B-5B;

FIG. 5C is a side view of the device of FIGS. 5A-5B, illustrating an exemplary removal method;

FIG. 9A is a side view of a fourth embodiment of a brachytherapy device;

FIG. 9B is a cross-sectional view of the device of FIG. 9A, taken along line 9B-9B;

FIG. 10A is a side view of a fifth embodiment of a brachytherapy device;

FIG. 10B is a cross-sectional view of the device of FIG. 10A, taken along line 10B-10B;

FIG. 11A is a side view of a sixth embodiment of a brachytherapy device;

FIG. 11B is a cross-sectional view of the device of FIG. 11A, taken along line 11B-11B;

FIG. 12A is a side view of a seventh embodiment of a brachytherapy device;

FIG. 12B is a cross-sectional view of the device of FIG. 12A, taken along line 12B-12B;

FIG. 13A is a side view of an eighth embodiment of a brachytherapy device;

FIG. 13B is a cross-sectional view of the device of FIG. 13A, taken along line 13B-13B;

FIG. 14A is a side view of a ninth embodiment of a brachytherapy device;

FIG. 14B is a cross-sectional view of the device of FIG. 14A, taken along line 14B-14B;

FIG. 15 is a side view of a brachytherapy device, showing a method for deploying the device in a curved configuration;

FIG. 17A is a side view of still another brachytherapy apparatus including a brachytherapy device and a delivery cannula;

FIG. 17B is a cross-section of the apparatus of FIG. 17A, taken along line 17B-17B;

FIGS. 29B and 29C are longitudinal cross-sectional views of the apparatus of FIG. 29A positioned within a lumpectomy cavity, showing the apparatus in collapsed and expanded configurations, respectively;

FIG. 30A is a side view of a third exemplary embodiment of an expandable brachytherapy apparatus in an expanded configuration;

FIGS. 31A and 31B are perspective views of a fourth exemplary embodiment of an expandable brachytherapy apparatus in collapsed and expanded configurations, respectively;

FIGS. 31C and 31D are side and end views, respectively, of the apparatus of FIGS. 31A and 31B in the collapsed configuration;

FIG. 33C is a side view of the apparatus of FIGS. 33A and 33B in the expanded configuration;

FIG. 33D is a cross-sectional detail of a coil member of the apparatus of FIG. 33C, taken along line 33D-33D;

FIG. 33E is another cross-sectional detail taken along a length of the coil member of FIG. 33C;

FIGS. 33F and 33G are cross-sectional views of a tissue structure, showing the apparatus of FIGS. 33A-33C implanted within the tissue structure, showing the apparatus partially expanded and fully expanded, respectively, within a cavity within the tissue structure;

FIGS. 35A and 35B are perspective and end views, respectively, of a seventh exemplary embodiment of an expandable brachytherapy apparatus, including inner and outer expandable layers of elongate members, the inner layer including wings to increase lateral surface area of the inner layer and/or increase lateral stability of the elongate members of the inner layer;

FIGS. 36A and 36B are perspective and end views, respectively, of an eighth exemplary embodiment of an expandable brachytherapy apparatus, including expandable elongate members and web members extending between adjacent elongate members;

FIGS. 37A and 37B are perspective and end views, respectively, of a ninth exemplary embodiment of an expandable brachytherapy apparatus, including inner and outer expandable layers, the inner layer including a sleeve for tissue shaping;

FIGS. 38A and 38B are perspective and end views, respectively, of a tenth exemplary embodiment of an expandable brachytherapy apparatus, including elongate members with wings to increase surface area of the elongate members;

FIG. 52A is a side view of a fifteenth exemplary embodiment of an expandable brachytherapy apparatus including expandable elongate members in a collapsed configuration, and an extended distal hub to provide a center lumen that extends distally beyond the expandable elongate members.

FIG. 52B is a longitudinal cross-section of the apparatus of FIG. 52A.

FIGS. 53A and 53B are perspective views of a sixteenth exemplary embodiment of an expandable brachytherapy apparatus, shown in collapsed and expanded configurations, respectively.

DETAILED DESCRIPTION OF EXEMPLARY EMBODIMENTS

Generally speaking, the present invention is directed to brachytherapy apparatus and methods. For example, in one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. For example, the apparatus and methods described herein may facilitate indwelling therapy using pre-arranged packages of radioactive sources, e.g., seeds, but also allow easy removal of the radiation sources at the completion of brachytherapy.

As used herein, "radiation source" and "radioactive source" may include most any therapeutic element operable to deliver a dose of radiation. For example, the radiation source may be one or more radioactive seeds or, alternatively, one or more LDR or HDR wire elements (e.g., Iridium wire).

The term "implantable," as used herein, indicates the capability of a device to be inserted into the body and then maintained in a relatively fixed or static position within the surrounding tissue for an extended period of time, e.g., an hour or more and, more preferably, several hours or more, including several days or more.

Furthermore, "target tissue," "target tissue region," "target region," and "target tissue volume," as used herein, may include most any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that the apparatus and methods described herein may be used for LDR or HDR brachytherapy, as described further below. Moreover, while described herein with respect to brachytherapy, the apparatus and methods may apply to other therapy regimens that benefit from the removable implantation of therapy-delivering elements. In an exemplary application, the apparatus and methods are described herein for treating breast cancer. However, it will be appreciated that the apparatus and methods described herein may be used for treating other cancers or conditions that may benefit from brachytherapy treatment.

Figure 1:
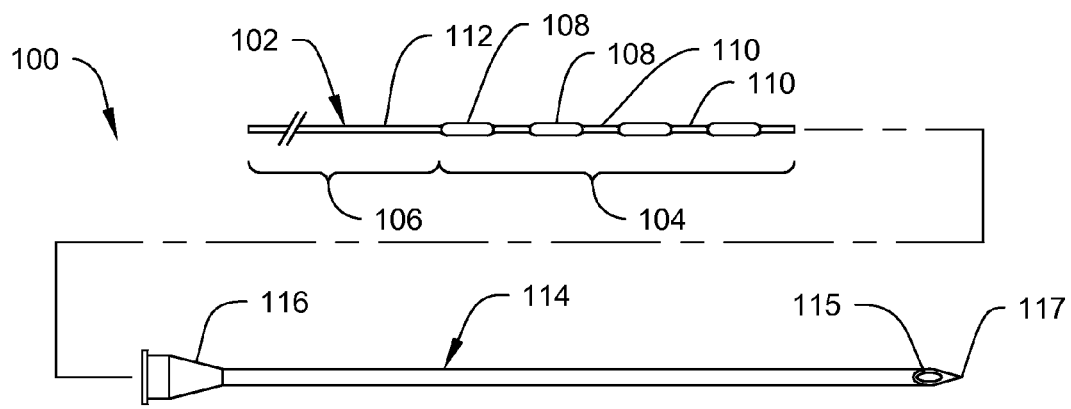
FIG. 1 is a side view of an exemplary embodiment of a brachytherapy apparatus including a strand of radioactive seeds or brachytherapy device, and a needle for receiving the device therein.
Figure 2A:
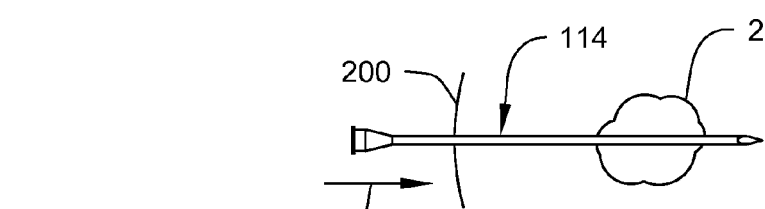
FIGS. 2A-2E are cross-sectional views of a breast, showing a method for using the brachytherapy apparatus of FIG. 1.
Figure 2B:
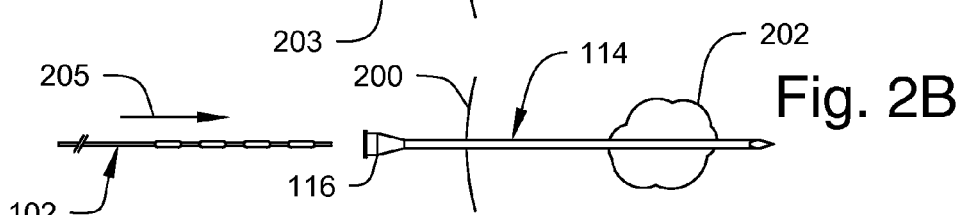
Figure 2C:
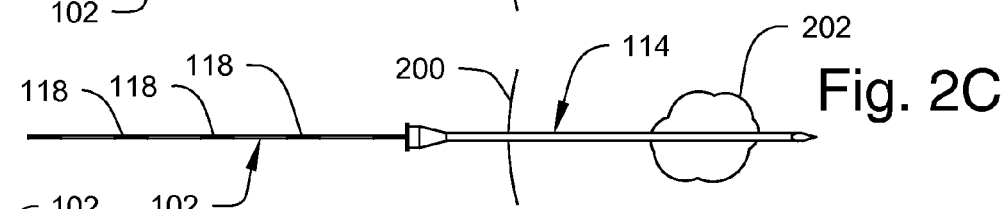
Figure 2D:
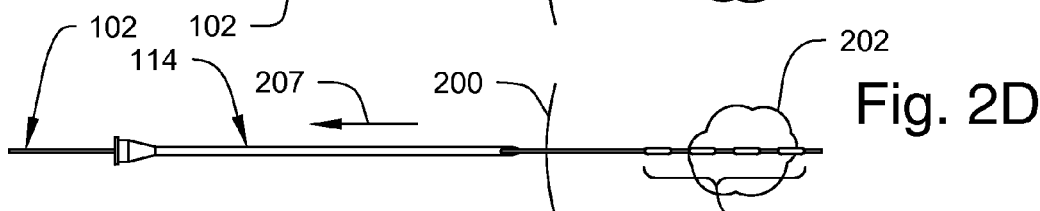
Figure 2E:
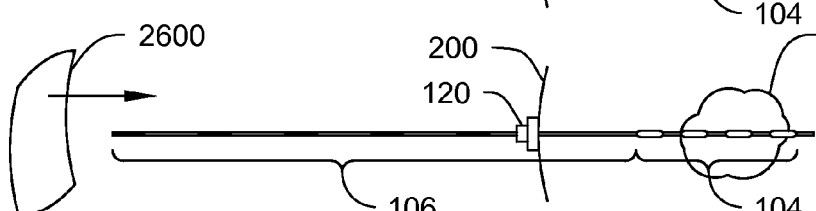
Figure 2F:
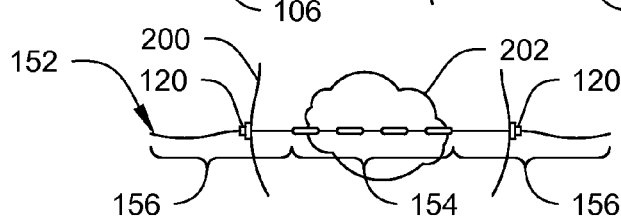
FIG. 2F is a cross-sectional view of a breast, showing another method for using the brachytherapy apparatus of FIG. 1.
Figure 6:
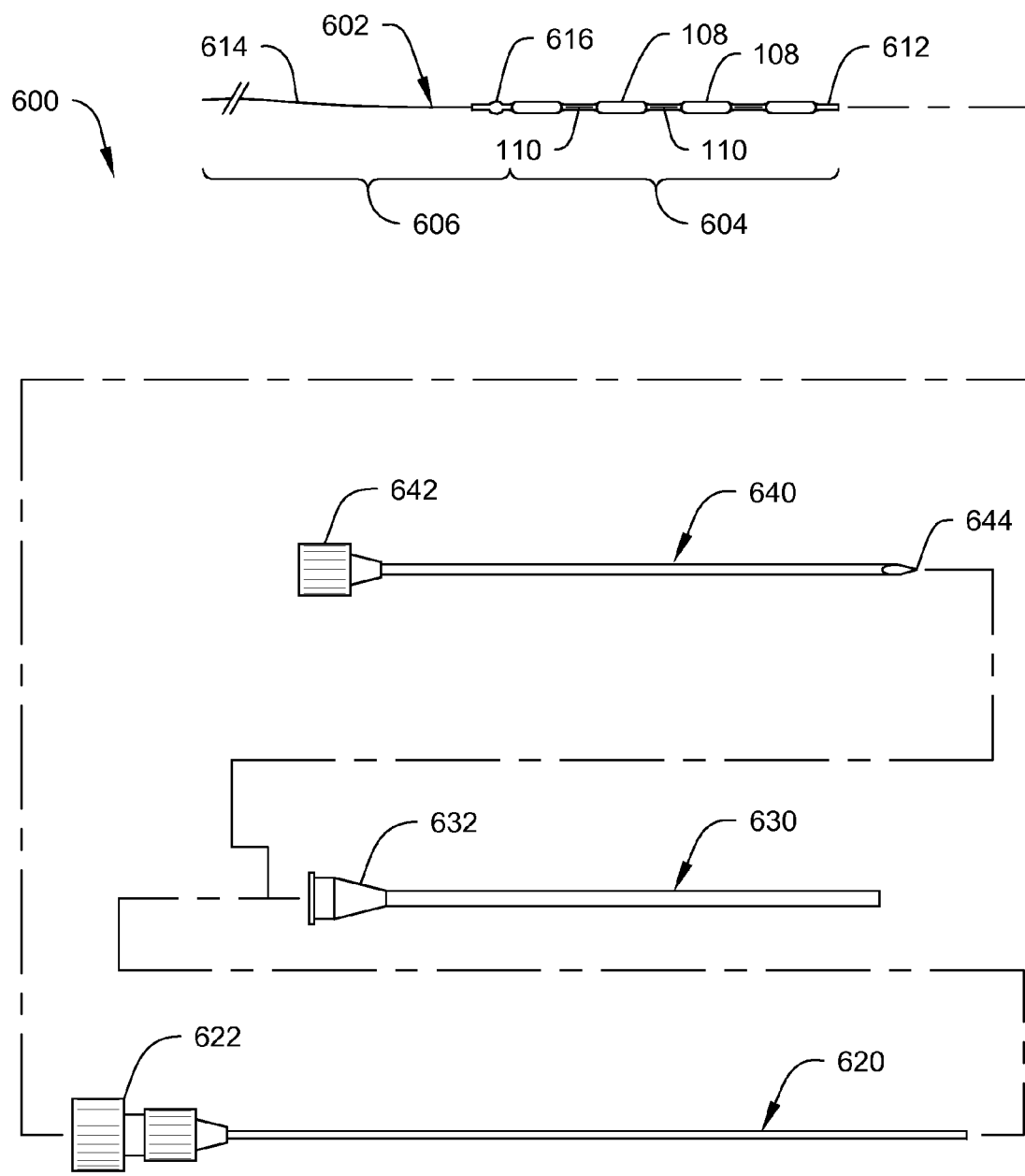
FIG. 6 is an exploded side view of another embodiment of a brachytherapy apparatus or kit.
Figure 7:
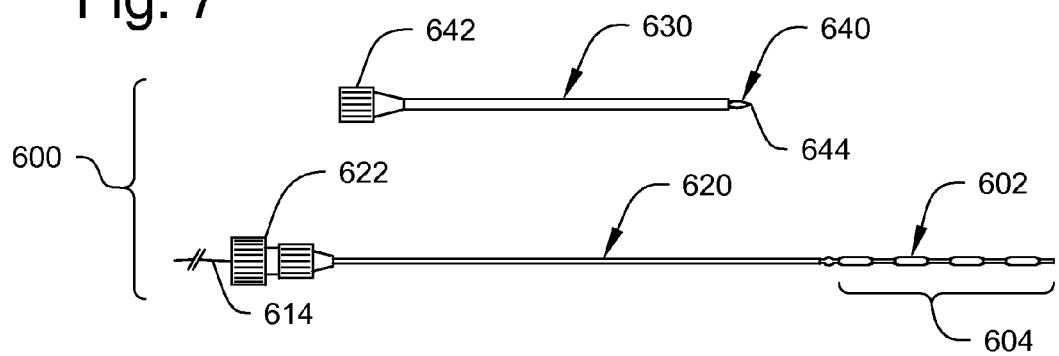
FIG. 7 is a side view of the brachytherapy apparatus of FIG. 6, partially assembled.
Figure 8A:
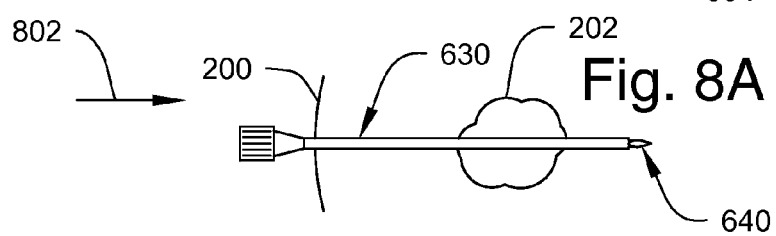
FIGS. 8A-8E are cross-sectional views of a breast, showing a method for using the brachytherapy apparatus of FIGS. 6 and 7.
Figure 8B:
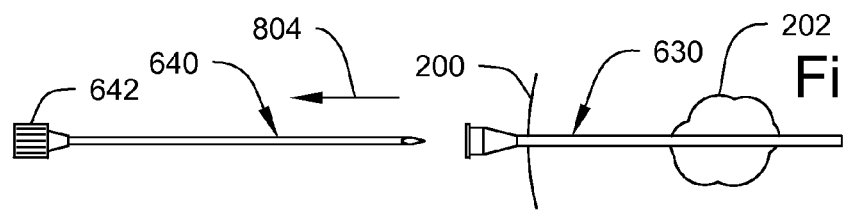
Figure 8C:
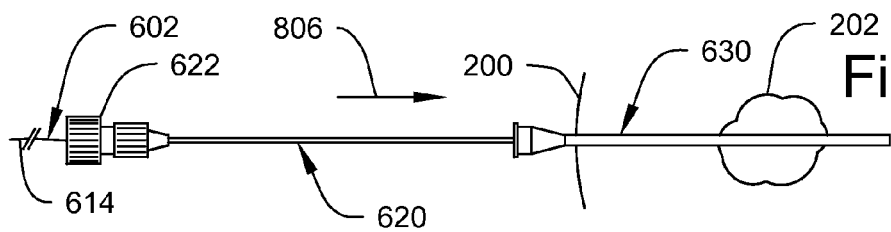
Figure 8D:
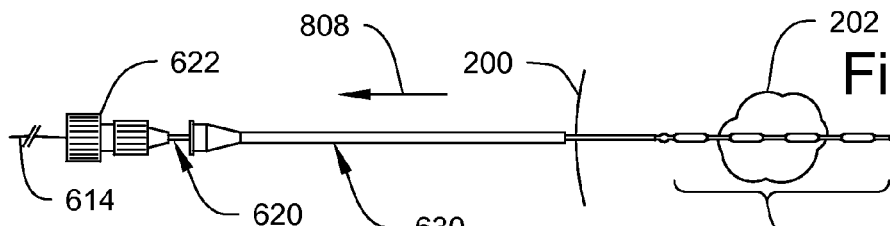
Figure 8E:
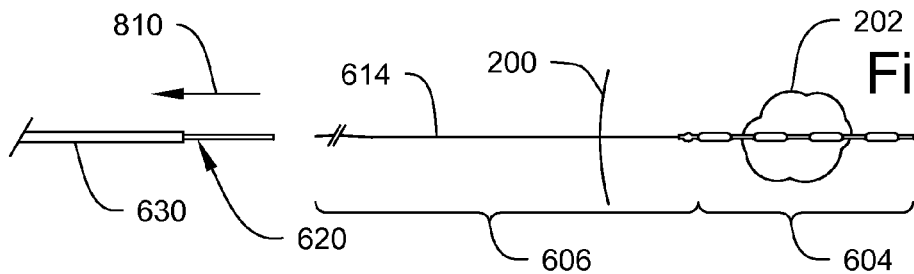
Figure 16A:
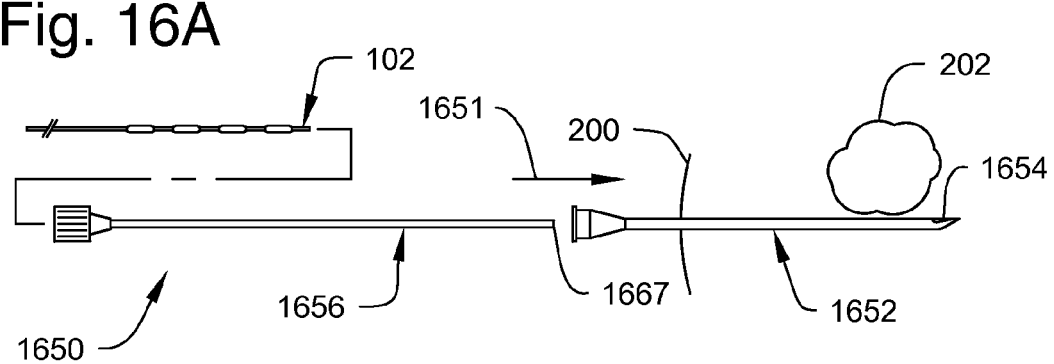
FIGS. 16A-16E are cross-sectional views of a breast, showing a method for delivering a brachytherapy device from a catheter along a curved pathway.
Figure 16B:
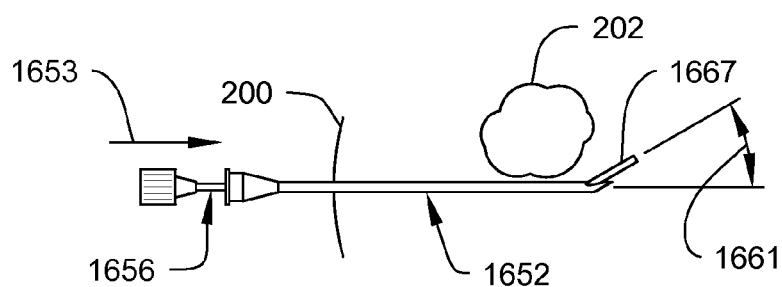
Figure 16C:
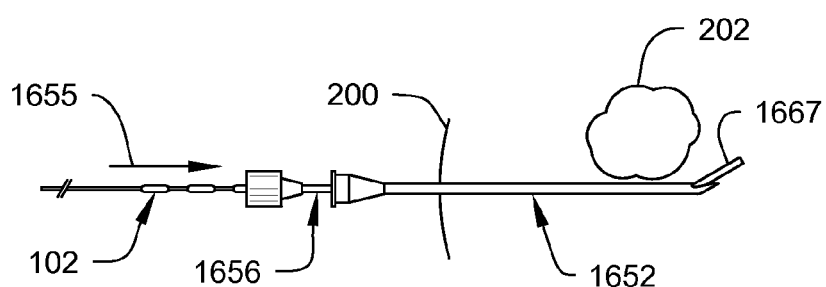
Figure 16D:
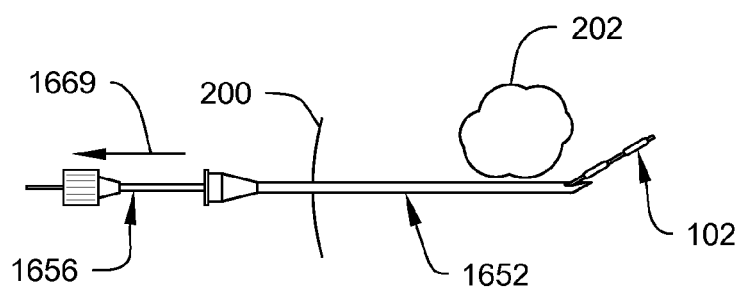
Figure 16E:
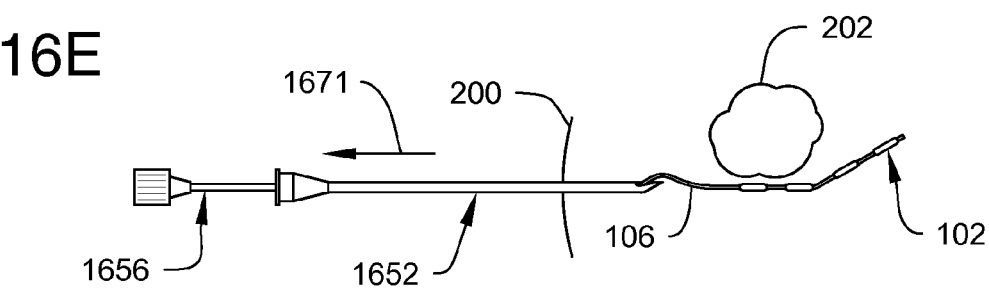
Figure 16F:
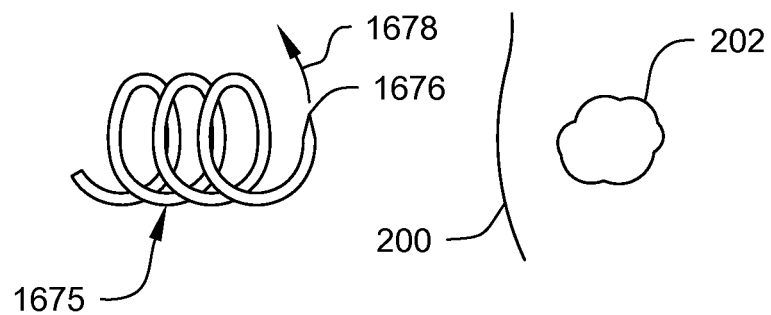
FIGS. 16F and 16G are cross-sectional views of a breast, showing method for delivering a brachytherapy device using a spiral-shaped catheter.
Figure 16G:
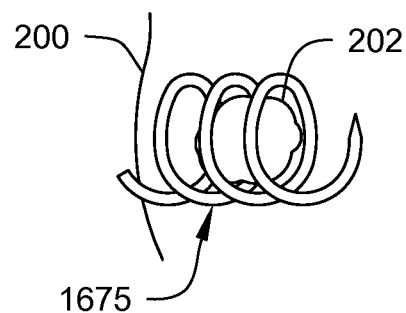
Figure 18:
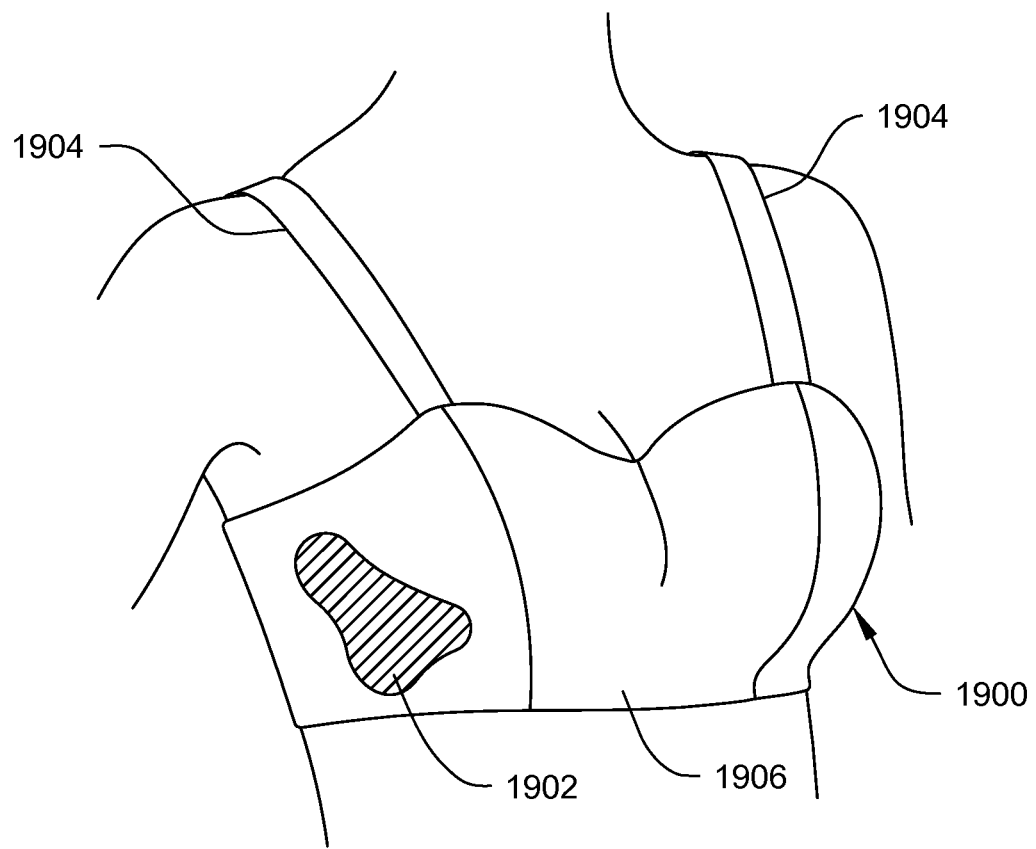
FIG. 18 is a perspective view of a radiation attenuating garment, e.g., brassiere.

With this introduction, turning to the drawings, FIG. 1 shows an exemplary kit or apparatus 100 for providing brachytherapy to a target tissue region of a body. The apparatus 100 may include an elongate and flexible, removably implantable brachytherapy treatment device 102 and a catheter, needle, or other delivery device 114. As shown, the brachytherapy device 102 is a strand including a therapy delivery portion 104 carrying radiation sources and an elongate and flexible tail portion 106. The tail portion 106 may facilitate removing the device 102 after completing treatment. Other components described below, e.g., locking members, may also be included with the apparatus 100.

The therapy delivery portion 104 may form a carrier pod of therapeutic elements, e.g., radiation sources such as radioactive seeds 108, secured relative to one another and to the therapy delivery portion 104. One or more spacers 110 may optionally be located between each seed 108 to obtain the desired seed separation. In some embodiments, the brachytherapy device 102 may include a flexible casing or casing member 112, in which the seeds 108 and optional spacers 110 are securely retained. FIGS. 2A-2E illustrate an exemplary method of using the brachytherapy apparatus 100 of FIG. 1. FIGS. 2F-17B show alternative embodiments of the therapy device 102 of FIGS. 2A-2E, and methods for using them. Additional information on making and using the apparatus 100 may be found in application Ser. No. 10/658,518, filed Sep. 9, 2003, Ser. No. 11/554,731, filed Oct. 31, 2006, Ser. No. 11/557,747, filed Nov. 8, 2006, and Ser. No. 11/276,851, filed Mar. 16, 2006. The entire disclosures of these applications are expressly incorporated by reference herein.

Figure 19A:
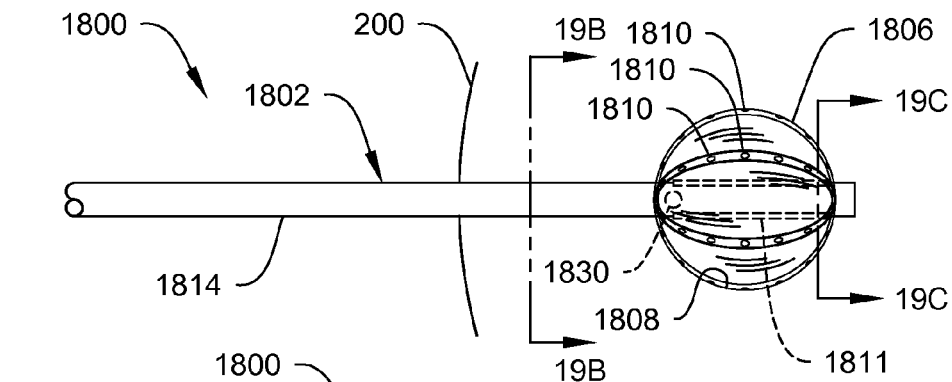
FIG. 19A is a side view of a balloon catheter apparatus, e.g., an HDR catheter.
Figure 19B:
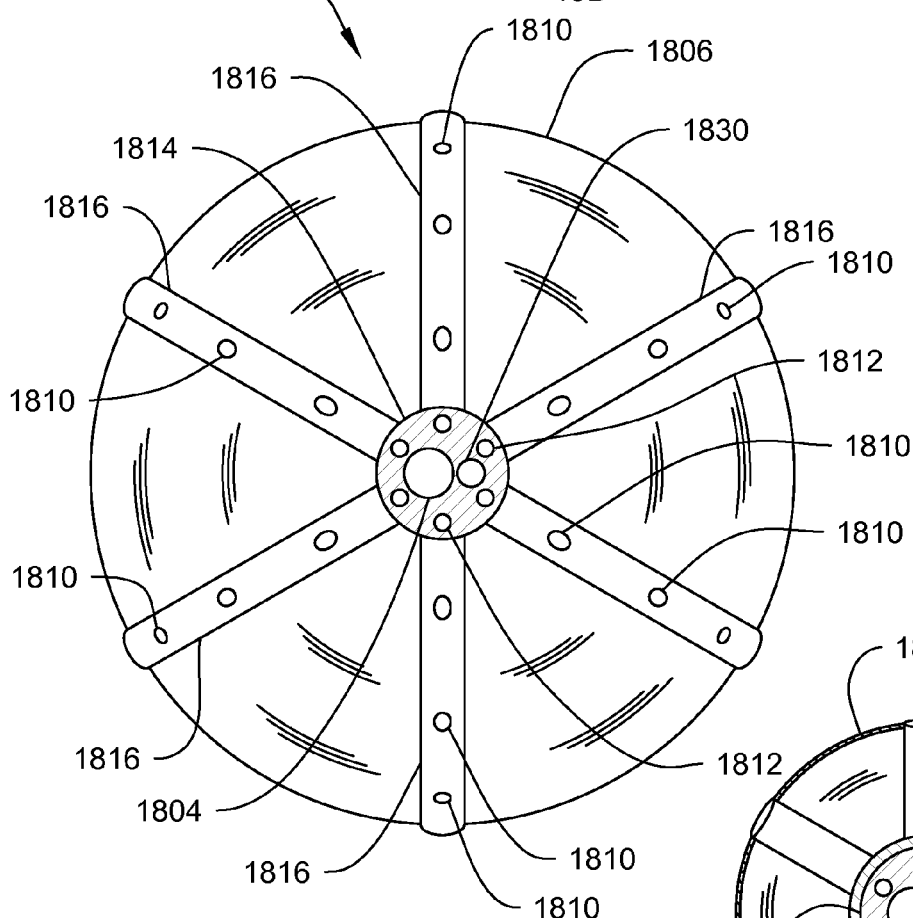
FIGS. 19B and 19C are cross-sectional views of the apparatus of FIG. 19A, taken along lines 19B-19B and 19C-19C, respectively.
Figure 19C:
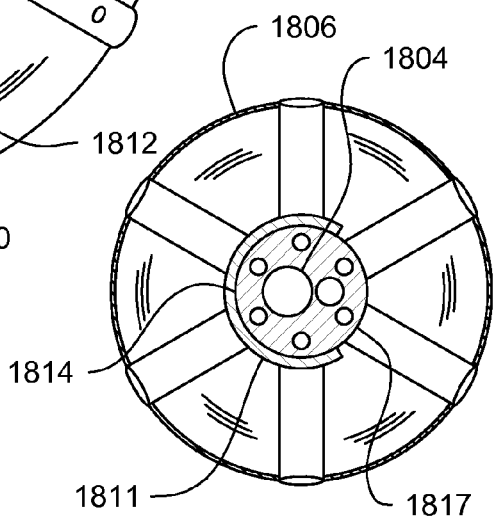
Figure 20:
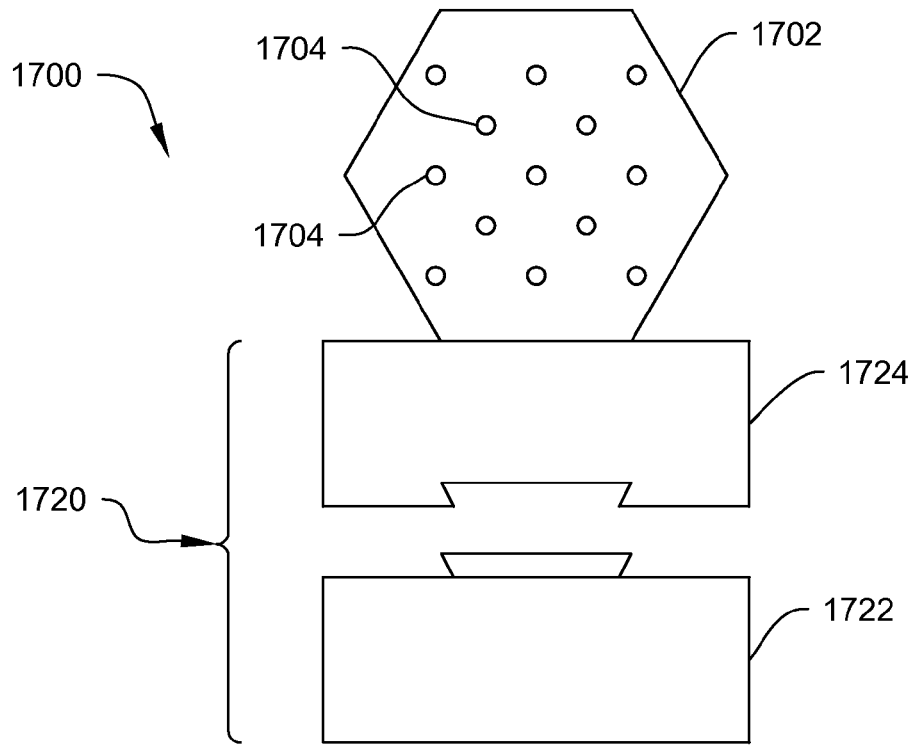
FIG. 20 is a side view of an exemplary embodiment of a delivery or implantation system that may be used with the brachytherapy methods and apparatus described herein.
Figure 21:
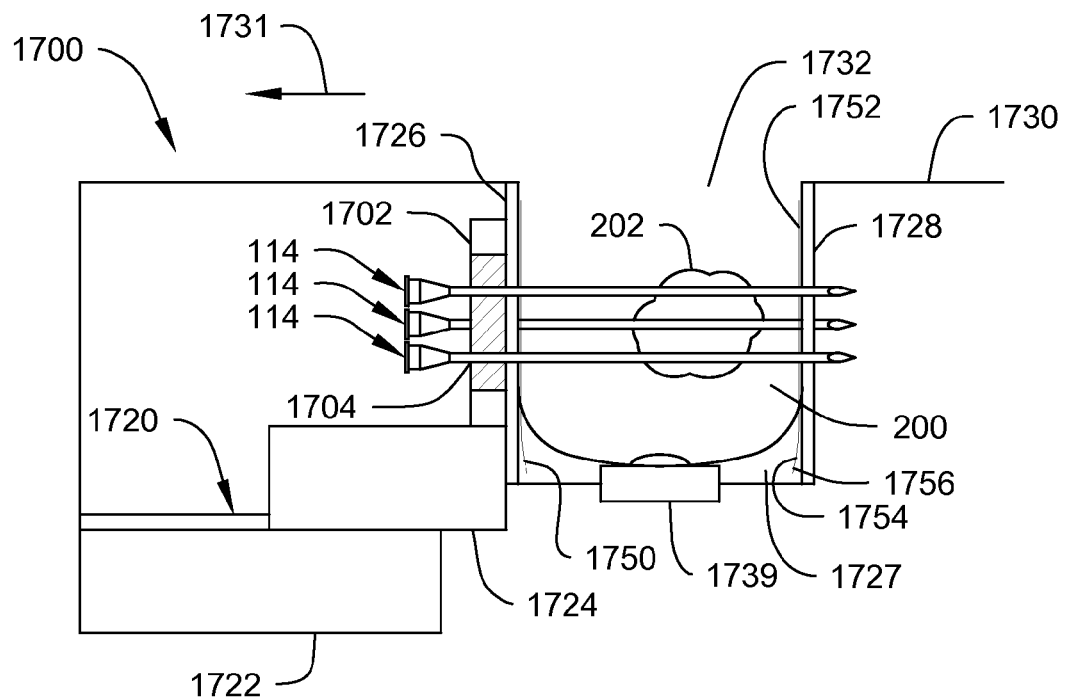
FIG. 21 is a top view of the delivery system of FIG. 20 being used to deliver a plurality of brachytherapy devices into a breast.
Figure 22:
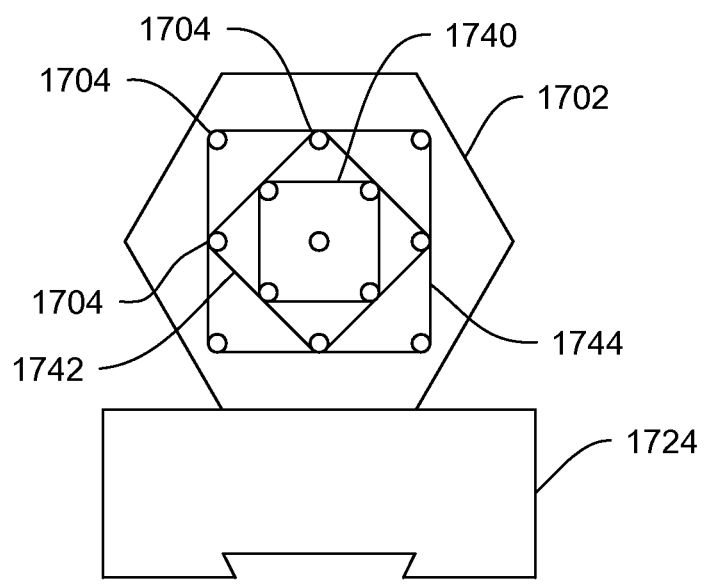
FIG. 22 is a side view of an exemplary catheter or needle guiding template, e.g., that may be used with the system of FIG. 21.
Figure 23:
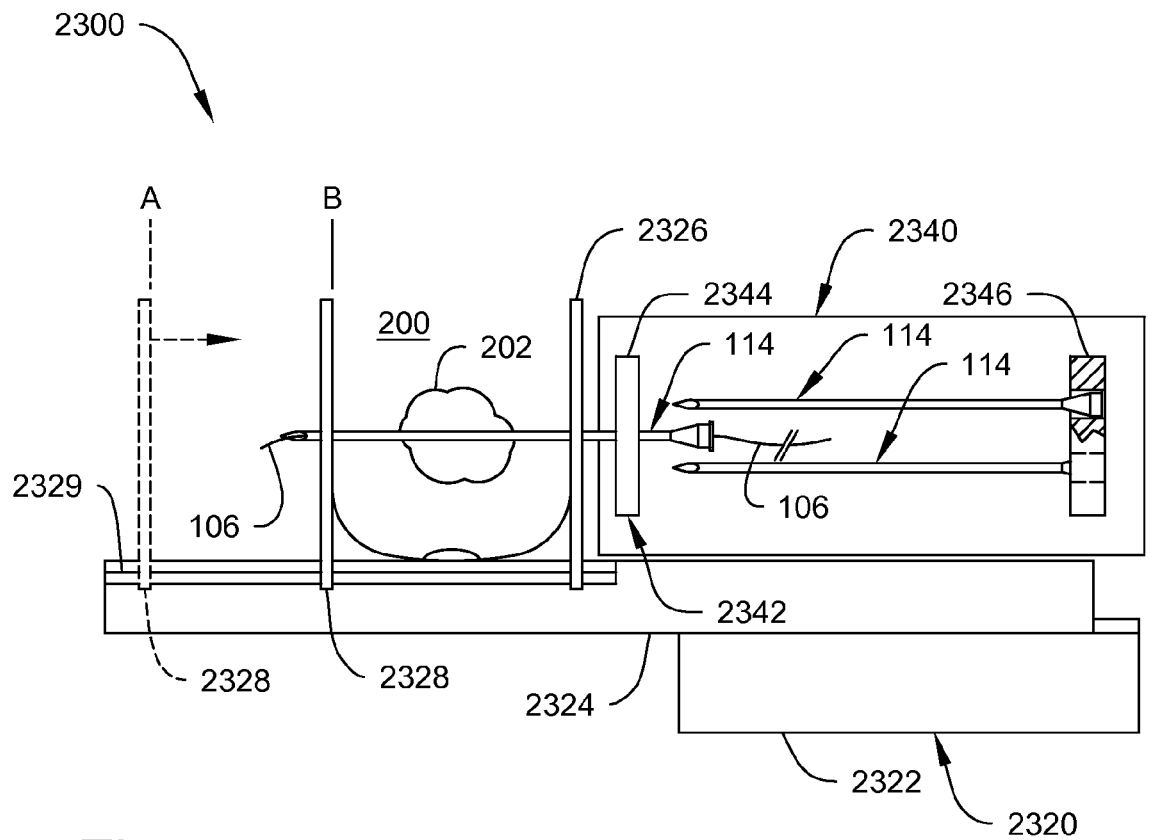
FIG. 23 is a top view of another delivery or implantation system being used to deliver a plurality of brachytherapy devices into a breast.
Figure 24:
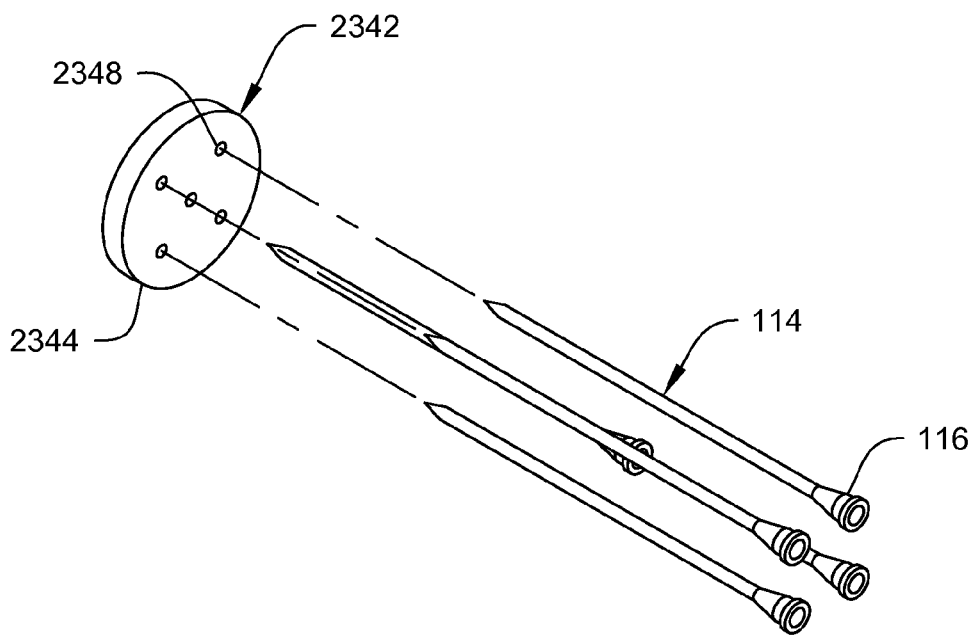
FIG. 24 is an exploded perspective view of a cartridge for receiving needles that may be included in the system of FIG. 23.
Figure 25A:
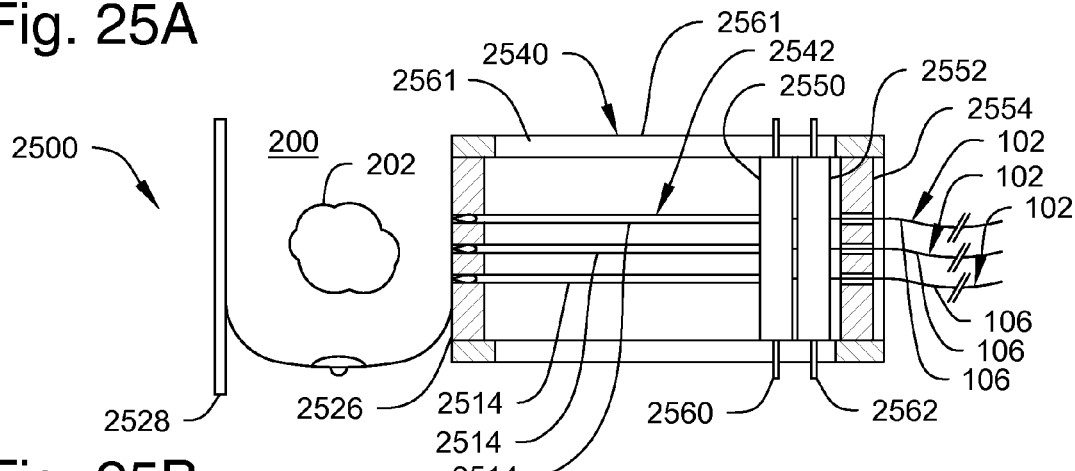
FIGS. 25A-25D are top views of another embodiment of a delivery or implantation system being used to deliver a plurality of brachytherapy devices into a breast.
Figure 25B:
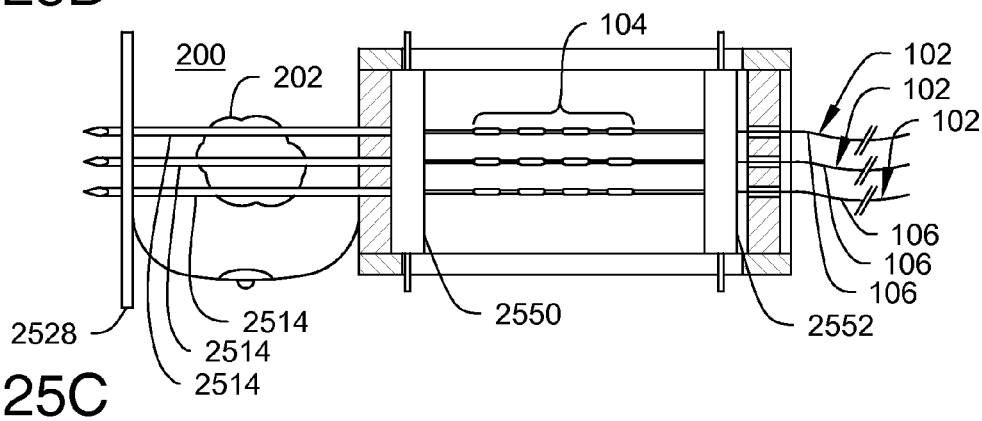
Figure 25C:
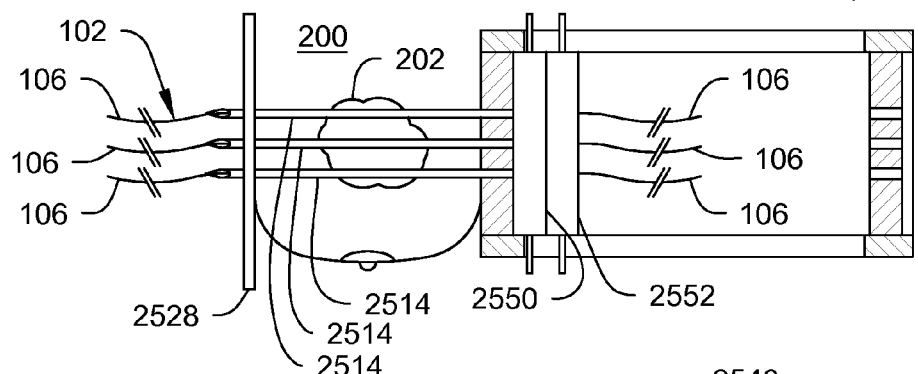
Figure 25D:
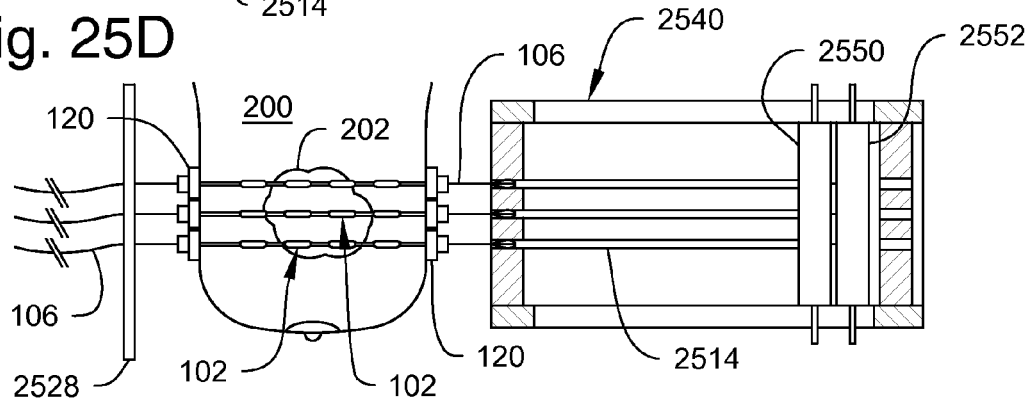
Figure 26:
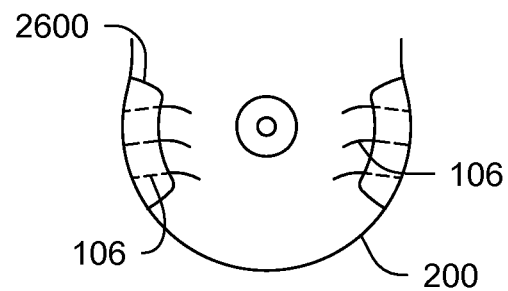
FIG. 26 is a front view of a portion of a human body, showing a plurality of brachytherapy devices implanted and secured within a breast.
Figure 27:
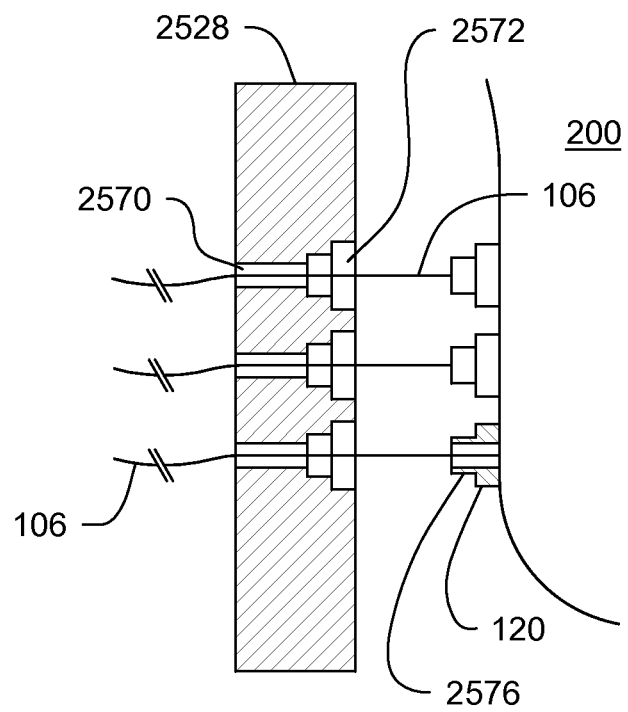
FIG. 27 is a cross-sectional view of a portion of the system of FIGS. 25A-25D.

FIGS. 19A-19C illustrate incorporation of a HDR shielded catheter on a balloon-type brachytherapy treatment device 1800. The device 1800 may be similar to the device disclosed in U.S. Pat. No. 5,913,813 to Williams et al., the disclosure of which is expressly incorporated by reference herein. For example, it may include a brachytherapy catheter assembly 1802 having a catheter shaft 1814 with a proximal end and a distal end. An inflatable balloon 1806 may be coupled to the catheter shaft 1814 between the proximal end and the distal end. An inflation lumen 1830 may extend along the catheter shaft 1814 between the inflatable balloon 1806 and the proximal end to allow inflation of the balloon. A dose delivery lumen 1804 (see FIG. 19B) may also be provided and extend along the catheter shaft 1814 from the proximal end towards and the distal end, e.g., extending between the inflatable balloon 1806 and the proximal end. Methods for using the device 1800 are disclosed in the applications incorporated by reference above.

FIGS. 20-27 show various exemplary systems for implanting LDR brachytherapy devices, such as those described elsewhere herein. For example, in the embodiment shown in FIGS. 20-22, a system 1700 is shown that includes a catheter or needle guiding template 1702 having a predetermined number and pattern (array) of openings 1704. The template 1702 may form part of an adjustable catheter or needle guiding apparatus by coupling to a stereotactic table 1720, e.g., using base portion 1722 and translating portion 1724. The stereotactic table 1720 may be coupled or attached to a patient locating or treatment surface 1730, e.g., patient table. Use of the systems is described in the applications incorporated by reference above.

While many of the devices and apparatus described herein are directed to linear placement, it may be beneficial to locate radioactive sources within a tumor or lumpectomy cavity in a more sophisticated geometry. Moreover, apparatus, devices, and methods in accordance with other embodiments described herein may permit implantation of brachytherapy devices in a first or collapsed, e.g., substantially straight, configuration, after which they may be externally actuated to a second or deployed, e.g., curvilinear, configuration once located within the target tissue region, e.g., within a lumpectomy cavity.

The apparatus may include one or more brachytherapy devices having one or more radiation sources, such as those shown and described elsewhere herein (e.g., device 102 shown in FIG. 1). Alternatively, one or more radiation sources may be introduced into the apparatus after implantation, as described elsewhere herein.

Such apparatus and methods may permit implantation through a single, minimally-sized incision, yet may subsequently deploy in-situ to provide a dose delivery region that is geometrically better suited to the curvilinear shape of the target tissue (e.g., the region of tissue surrounding the lumpectomy cavity). In addition, the deployed configuration may provide a broader array from which radiation sources may deliver their desired dose, as compared to the first collapsed configuration.

Additionally, such in-situ deployable apparatus, devices, and systems may enhance fixation of radiation sources within a specific location of the lumpectomy cavity. Such fixation may allow a substantially fixed geometry to be selected between the implanted radiation sources and the surrounding target tissue. By minimizing movement of the radiation sources (relative to the target tissue) during subsequent patient activity, brachytherapy exposure may more closely follow pre-implant dose planning regimens.

One embodiment of such a deployable apparatus is diagrammatically illustrated in FIGS. 28A-28D by an expanding cage-type apparatus 2800. Generally, the intracavitary apparatus 2800 includes a therapy delivery portion 2800a, which may be deployed within a target location of a patient's body, e.g., tumor or cavity within a breast or other body structure 200, and a tail portion 2800b, which extends from the therapy delivery portion 2800a, e.g., such that the tail portion 2800b protrudes outside of the body structure 200. As shown in FIGS. 28A-28D, the therapy delivery portion 2800a may be movable between a collapsed configuration, e.g., for introduction through a tissue tract to a target location, and an expanded configuration, e.g., for providing a three dimensional array of pathways at the target location 2802, as described further below.

Figure 54:
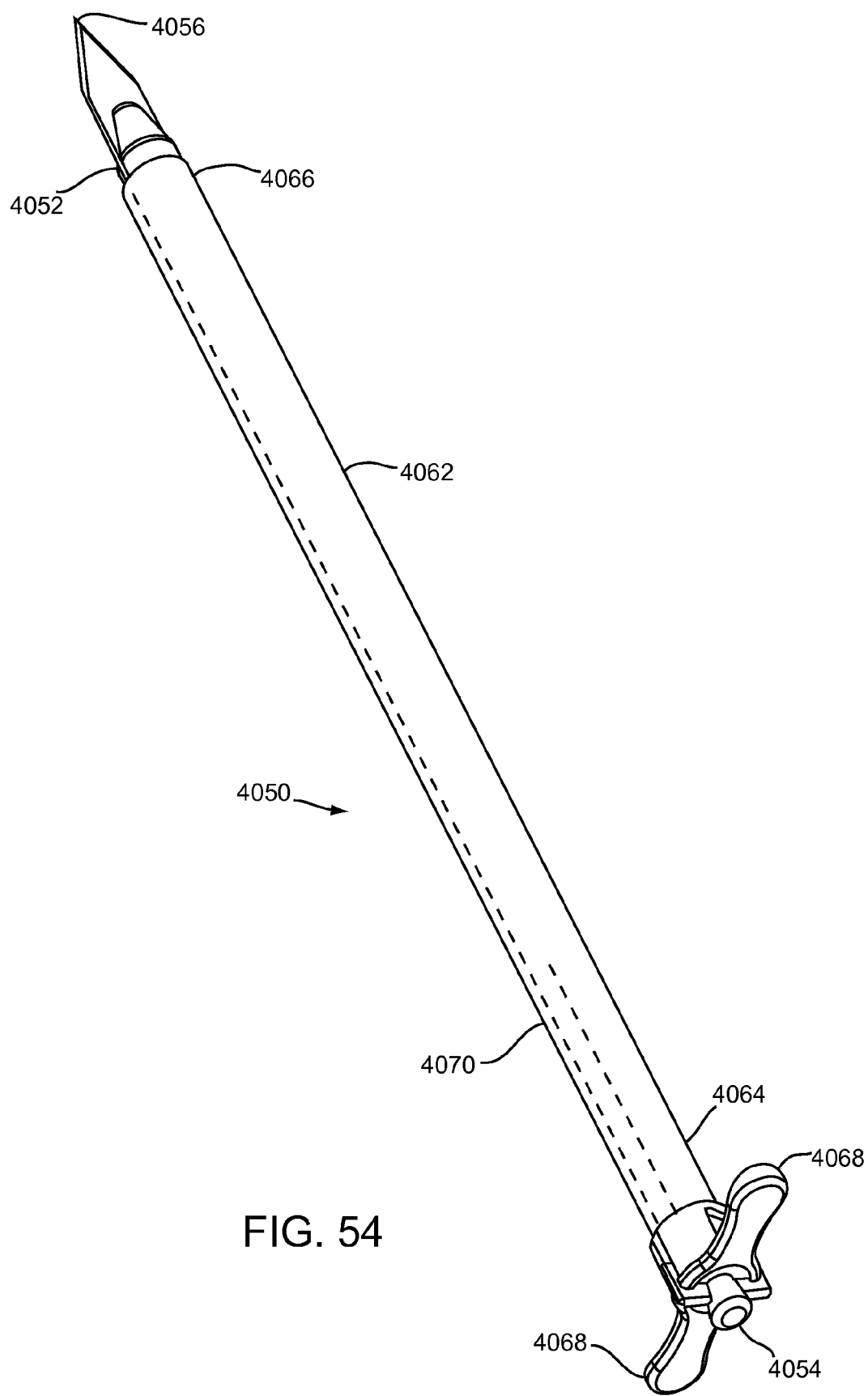
FIG. 54 is a perspective view of an apparatus for delivering an expandable brachytherapy apparatus into tissue, the apparatus including a tear-away sheath over a trocar.

Optionally, the apparatus 2800 may include a sheath or other cover (not shown), which may overly the therapy delivery portion 2800a, e.g., until deployment. In addition or alternatively, a tubular delivery device, such as catheter, cannula, or needle 2804, may be provided for introducing the apparatus 2800 into the target location. A trocar or other instrument (not shown) may be disposed within the needle 2804 such that a sharpened tip (also not shown) of the trocar extends beyond a distal end 2804a of the needle 2804 to facilitate insertion of the needle 2804 through tissue, e.g., to create a tissue tract from the patient's skin to the target location. The trocar may be removed after creating the tract, thereby allowing the apparatus 2800 to then be introduced into the needle 2804. An exemplary embodiment of a delivery apparatus 4050 including a trocar 4052 and sheath 4062 are shown in FIG. 54 and described further below.

Alternatively, the needle 2804 may include a sharpened distal tip (not shown). In this alternative, the trocar may be eliminated, and, optionally, an obturator or other instrument (also not shown) may be initially provided to occlude the lumen while the needle 2804 is advanced through tissue. After removing the obturator, the apparatus 2800 may be introduced into the needle 2804, e.g., directly or carried within a sheath or cover (not shown).

In a further alternative, the apparatus 2800 may include a sharpened distal tip (not shown), e.g., similar to other embodiments described herein. The distal tip may extend beyond the distal end 2804a of the needle 2804, thereby creating the tract when the needle 2804 and apparatus 2800 are advanced together through tissue. In yet another alternative, the apparatus 2800, with a sharpened distal tip, may be advanced directly through tissue to create the tissue tract, and the needle 2804 may be eliminated.

Figure 28A:
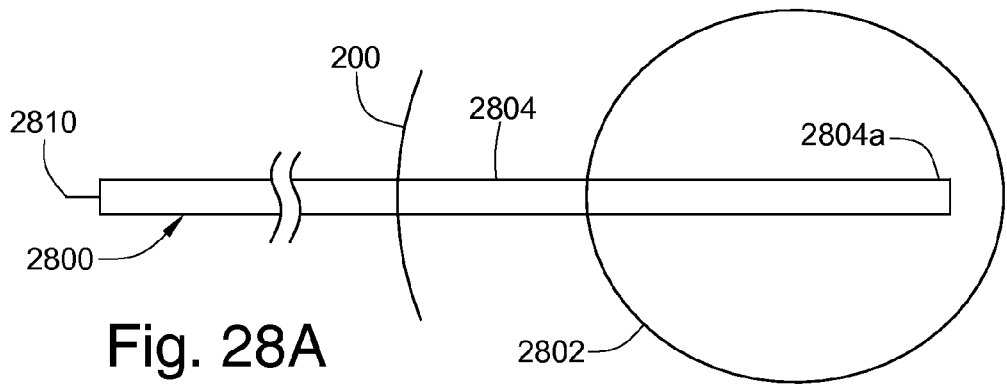
FIGS. 28A-28D are cross-sectional views of a breast including a lumpectomy cavity, showing a first exemplary embodiment of an expandable brachytherapy treatment apparatus being delivered into the cavity.

FIG. 28A illustrates the brachytherapy apparatus 2800 after insertion through an incision in the body. The apparatus 2800 is positioned such that the therapy delivery portion 2800a is located within a hollow target region, e.g., lumpectomy cavity 2802. As illustrated in FIG. 28A, a catheter or needle 2804 has been inserted through the body structure, e.g., breast 200, and into the cavity 2802. Once the apparatus 2800 is in place, the needle 2804 may be retracted or removed, exposing the therapy delivery portion 2800a.

Figure 28B:
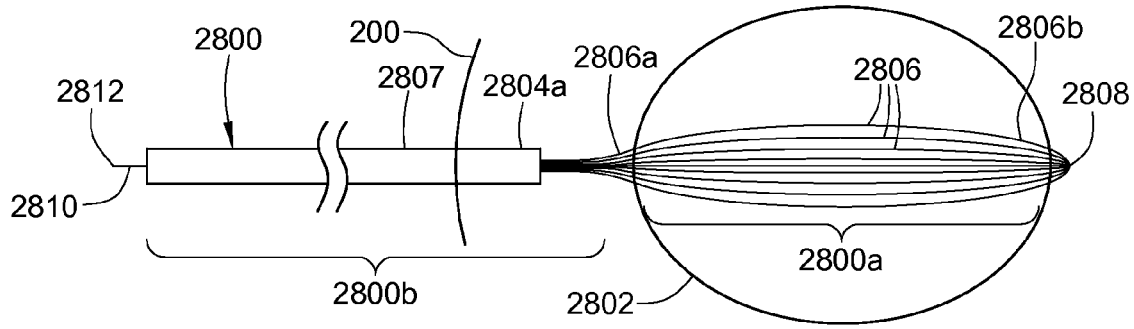

As shown, the therapy delivery portion 2800a includes a plurality of radioactive brachytherapy devices, e.g., flexible, elongate members 2806 including proximal and distal ends 2806a, 2806b and configured for carrying one or more radiation sources. The apparatus 2800 includes a hub or outer body member 2807 to which the proximal ends 2806a of the elongate members 2806 are secured, as shown in FIG. 28B. The distal ends 2806b of the elongate members 2806 may be fixed or otherwise retained at a distal end 2808 of a core member 2810. As shown, the core member 2810 extends through the body member 2807 such that a proximal end 2812 of the core member 2810 extends out of the body structure 200. Alternatively, a handle (not shown) may be coupled or otherwise extend proximally from the core member 2810.

Figure 28C:
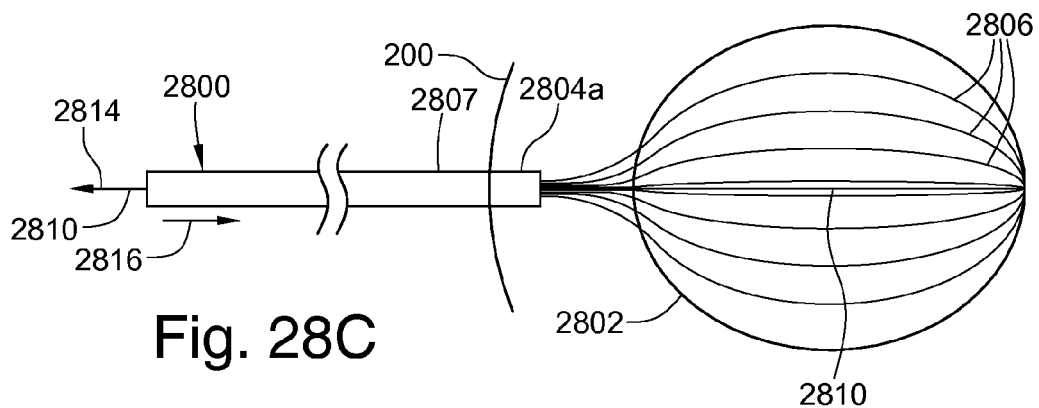
Figure 28D:
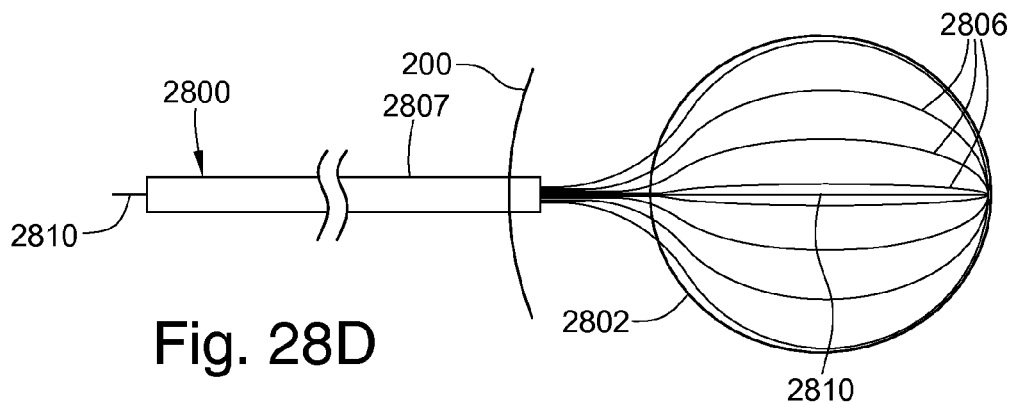

The hub and core member 2810 may be movable axially relative to one another to expand and/or collapse the therapy delivery portion 2800a. For example, by manipulating the proximal end 2812 of the core member 2810 and the body member 2807, e.g., by displacing the core member 2810 in a first (proximal) direction 2814 and/or the body member 2807 in a second (distal) direction 2816, the elongate members 2806 may be expanded within the volume of the cavity 2802, as shown in FIG. 28C. When fully expanded, the elongate members 2806 may contact walls of the cavity 2802, as shown in FIG. 28D, and/or push into tissue surrounding the walls of the cavity 2802.

Figure 29A:
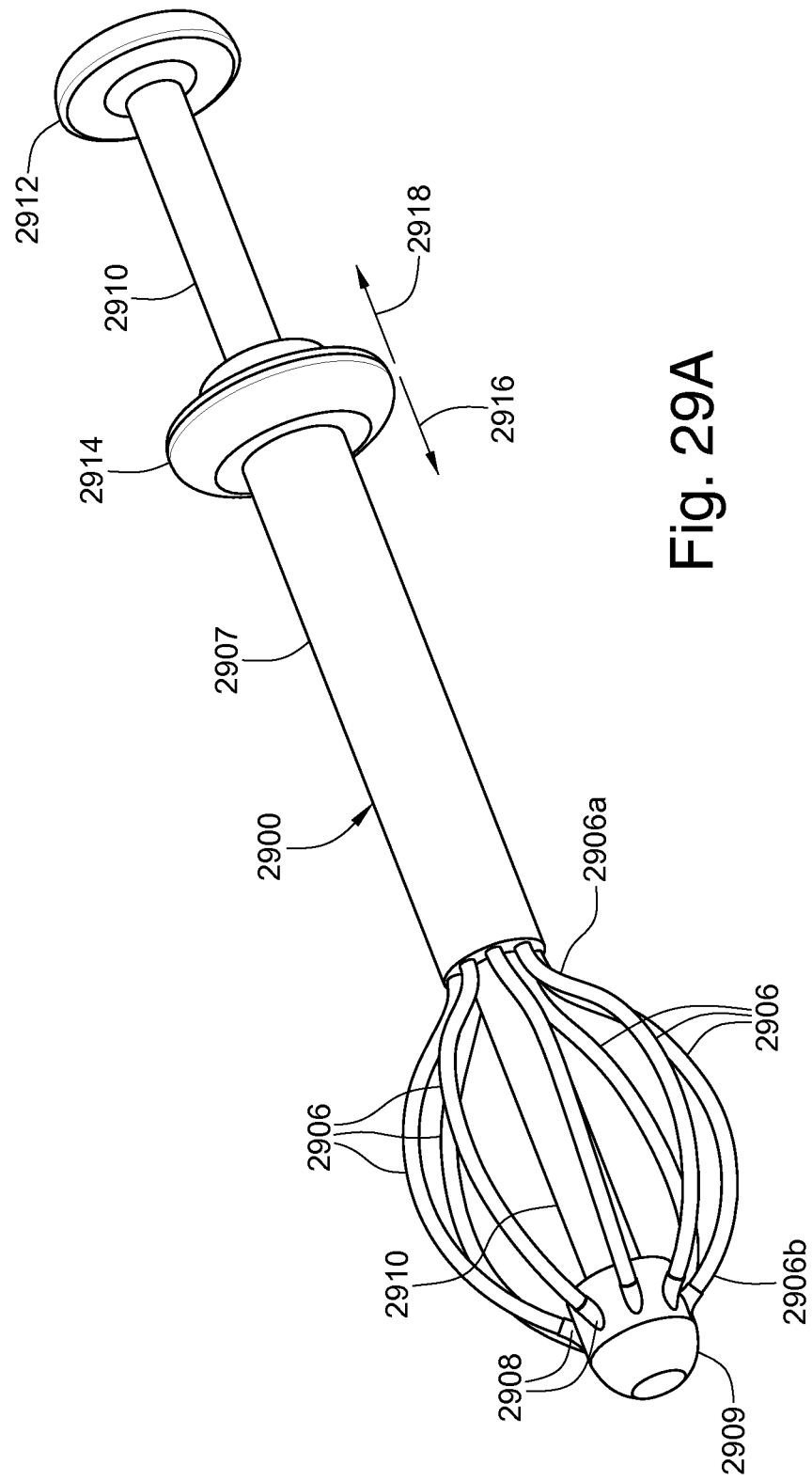
FIG. 29A is a perspective view of a second exemplary embodiment of an expandable brachytherapy apparatus in an expanded or deployed configuration.

FIGS. 29A-29F illustrate another embodiment of an in-situ deployable brachytherapy apparatus 2900. The apparatus is similar in many respects to the apparatus 2800 described above. For example, the apparatus 2900 may include an expandable cage of radioactive brachytherapy devices, e.g., flexible, elongate members 2906. Each elongate member 2906 includes a distal end 2906b coupled to a hub 2909 and a proximal end 2906a coupled to a body member 2907. A flange 2914 may be provided at a proximal end of the body member 2907, as shown in FIG. 29A. A core member 2910, also coupled to the hub 2909, may extend through the body member 2907 and past the flange 2914, terminating at a button or other handle 2912.

The proximal ends 2906a of the elongate members 2906 may terminate within the body member 2907. However, as explained further below, other body member embodiments may include passageways that provide access to lumens formed in the elongate members 2906 from a proximal side of the flange 2914. In a further alternative, tubular members (not shown) may extend proximally from the body member, similar to other embodiments described herein.

The apparatus 2900 may be moved from a first collapsed configuration where the elongate members 2906 are generally straight and parallel to a central axis of the core member 2910 (shown in FIG. 29B), to a second deployed configuration where the elongate members 2906 are curvilinear (shown in FIGS. 29A and 29C). For example, movement to the deployed configuration may be achieved by moving the flange 2914, and thus the body member 2907, away from the button 2912 (i.e., in the distal direction 2916). Similarly, the apparatus 2900 may be collapsed by moving the flange 2914 towards the button 2912 (i.e., in the proximal direction 2918).

It will be appreciated that other actuators may be provided in addition to the flange 2914 and button 2912. For example, the core member 2910 and body member 2907 may include mating threads (not shown), e.g., on an inner surface of the body member 2907 and on an outer surface of the core member 2910 within the body member 2907. Rather than axial movement of the button 2912, the button 2912 may be rotated in a first direction, thereby causing the body member 2907 to move axially, i.e., distally, over the core member 2910 to expand the elongate members 2906 to the expanded configuration. The button 2912 may be rotated in a second opposite direction to collapse the elongate members 2906 back to the collapsed configuration. Additional information on exemplary embodiments of removable actuators are described further below.

Optionally, in any of these embodiments, the button 2912 and/or portion of the core member 2910 beyond the flange 2914 may be detachable from the rest of the core member 2910 (within the body member 2907 and extending to the hub 2909), e.g., to reduce a profile of the apparatus 2900 after implantation. For example, the detachable portion and the remaining portion of the core member (not shown) may include mating male/female ends, e.g., connected by threads or other releasable connectors (also not shown). Alternatively, a barrel or other structure may be disposed within the body member 2907 that is coupled to the proximal ends 2906a of the elongate members 2906 such that axial movement of the barrel relative to the body member 2907 causes expansion or collapse of the elongate members 2906.

In another option, the core member 2910 (and/or actuator) may include one or more stops (not shown) to limit movement of the body member 2907, e.g., to limit expansion of the elongate members 2906. The stops may provide a maximum size for the expanded configuration or may provide a range of sizes through which the elongate members 2906 may be expanded and fixed. For example, ratchets or detents (not shown) may allow the body member 2907 to be moved, yet maintained at a position to which the body member 2907 is moved relative to the core member 2910.

FIGS. 29B and 29C illustrate the brachytherapy apparatus 2900 after insertion through an incision in the body structure, e.g., breast 200. The apparatus 2900 may be positioned such that its distal end, e.g., hub 2908, is located within the lumpectomy cavity 2902. In the illustrated embodiment, the apparatus 2900 is inserted through an existing incision. However, the apparatus 2900 may have features (e.g., a sharp distal tip) that permit it to make its own incision, as described above. The sharp distal tip may enable the tip of the apparatus 2900 to be positioned beyond the edge of the cavity, e.g., in order to position the expanded elements in an optimal position within the cavity.

In some embodiments, the apparatus 2900 may include a tear-away sheath (not shown) that covers the elongate members 2906 during handling and/or implantation. After the apparatus 2900 is positioned as shown in FIG. 29B, the sheath may be removed (e.g., using a tear-strip positioned outside the body and/or one or more weakened seams or regions extending along the sheath) to expose the elongate members 2906. An exemplary embodiment of a tear-away sheath 4062 is shown in FIG. 54 and described further below.

Once the apparatus 2900 is in place, e.g., as shown in FIG. 29B, the physician may displace the flange 2914 towards the body (in the distal direction 2916). Similarly, the button 2912 may be displaced proximally away from the flange 2914. This motion causes the elongate members 2906 to deploy, as shown in FIG. 29C, within the volume of the cavity 2902. When further expanded, the elongate members 2906 may contact the walls of the cavity and, when fully expanded, may press into the surrounding tissue sufficiently to cause the cavity walls to reconfigure in an interdigitating manner between the members 2906 (see, e.g., FIGS. 32D-32G, as described further below). This interdigitation or invagination of the walls results in generally fixing the apparatus 2900 relative to the tissue surrounding the cavity 2902.

As used herein, the terms "invagination" and "interdigitation" refer to pressing of one or more portions or elements of the apparatus 2900 outwardly from within a cavity 2902, into the tissue surrounding the cavity 2902, such that tissue adjacent the elements flows, folds, or extrudes inwardly between the elongate members 2906. FIGS. 32D-32H, for example, illustrate this concept. In addition to being substantially surrounded by tissue, one or more of the elongate members 2906 may penetrate into the surrounding tissue, e.g., such that the elongate member(s) 2906 may be completely surrounded by tissue, as described further below.

Figure 29D:
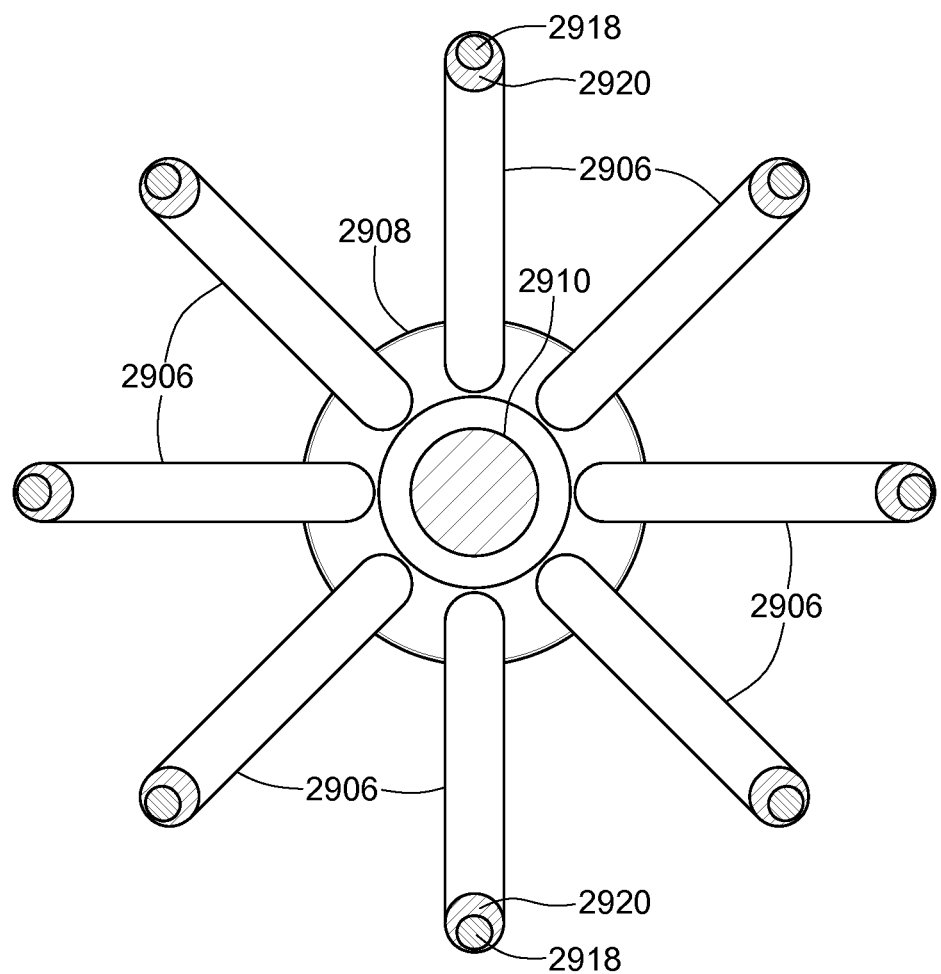
FIG. 29D is a cross-section of the apparatus of FIG. 29C, taken along lines 29D-29D.

FIG. 29D is a cross-sectional view of the apparatus 2900, taken along line 29D-29D of FIG. 29C. As shown in this view, the elongate members 2906 may be tubular members including one or more lumens, e.g., a first lumen 2918 and a second lumen 2920. The first lumen 2918 may be sized to receive a brachytherapy device, e.g., similar to the devices 102, 152, 402, 502, and 602 already described elsewhere herein, while the second lumen 2920 may be configured to hold a stiffening member (not shown). The stiffening member may assist in maintaining the proper orientation of the elongate members 2906, e.g., may assist in ensuring that the lumens 2918 (and, thus, the brachytherapy devices) are sufficiently stiff so as to prevent their deflection during expansion into the surrounding tissue and/or ensure that the elongate members 2906 expand substantially in a predetermined configuration.

Figure 29E:
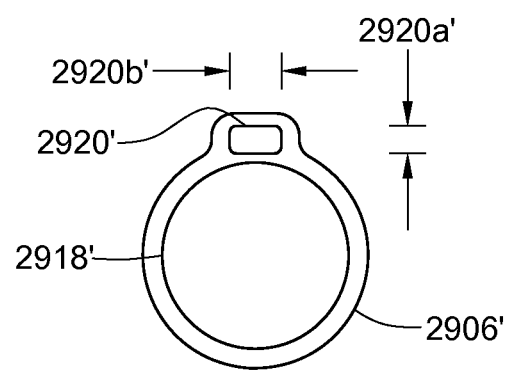
FIG. 29E is a cross-sectional detail of an alternative embodiment of an elongate member that may be included in the apparatus of FIGS. 29A-29D.

While illustrated in FIG. 29D as round in cross section, one or both of the first and second lumens may have other shapes. For example, FIG. 29E illustrates a cross section of an alternate member 2906' having a round first lumen 2918' and a second lumen 2920' that is rectangular or otherwise elongate in cross section. The rectangular cross section lumen 2920,' when occupied by a stiffening member of matching shape (e.g., a nitinol wire or band of rectangular cross section), may reduce rotational deflection (as well as other forms of deflection) of the elongate members 2906 during deployment. For example, because of the lesser moment about the minor dimension 2920a' compared to the major dimension 2920b,' the elongate members 2906' may preferentially bend outwardly during expansion, rather than laterally, e.g., towards an adjacent elongate member.

While FIGS. 29D and 29E illustrate the elongate members 2906 as dual lumen tubing, the elongate members 2906 may also be made with a single lumen, such as polymer or other flexible tubing. The polymer tubing, while flexible enough to be deployed into a curved configuration, may also be sufficiently stiff so as not to require a secondary stiffening member. Such tubing may be fabricated from high durometer polymers, such as nylons, polyetheretherketones (PEEK), polyimides, and the like. Optionally the tubing cross section may be non-circular in cross section (e.g. trapezoidal, rectangular) to facilitate the proper orientation of bending during device expansion and/or to increase lateral stability of the elements while in the expanded position. Additionally, the tubing may include reinforcing elements (e.g., flat wire braid, not shown) within its wall to provide enhanced torsional and/or flexural stiffness.

In further alternatives, the elongate members 2906 may include other features providing pathways extending between the proximal and distal ends 2906a, 2906b. For example, the elongate members 2906 may include grooves or tracks (not shown), which may receive one or more sources of radiation (also not shown), as described further below. The features may include any other interlocking features that restrict movement of one or more sources of radiation, e.g., to axial movement along the elongate members. Thus, as used herein, "pathway" may include a lumen, track, rail, or other feature on an elongate member configured for guiding one or more radiation sources along the elongate member.

Figure 29F:
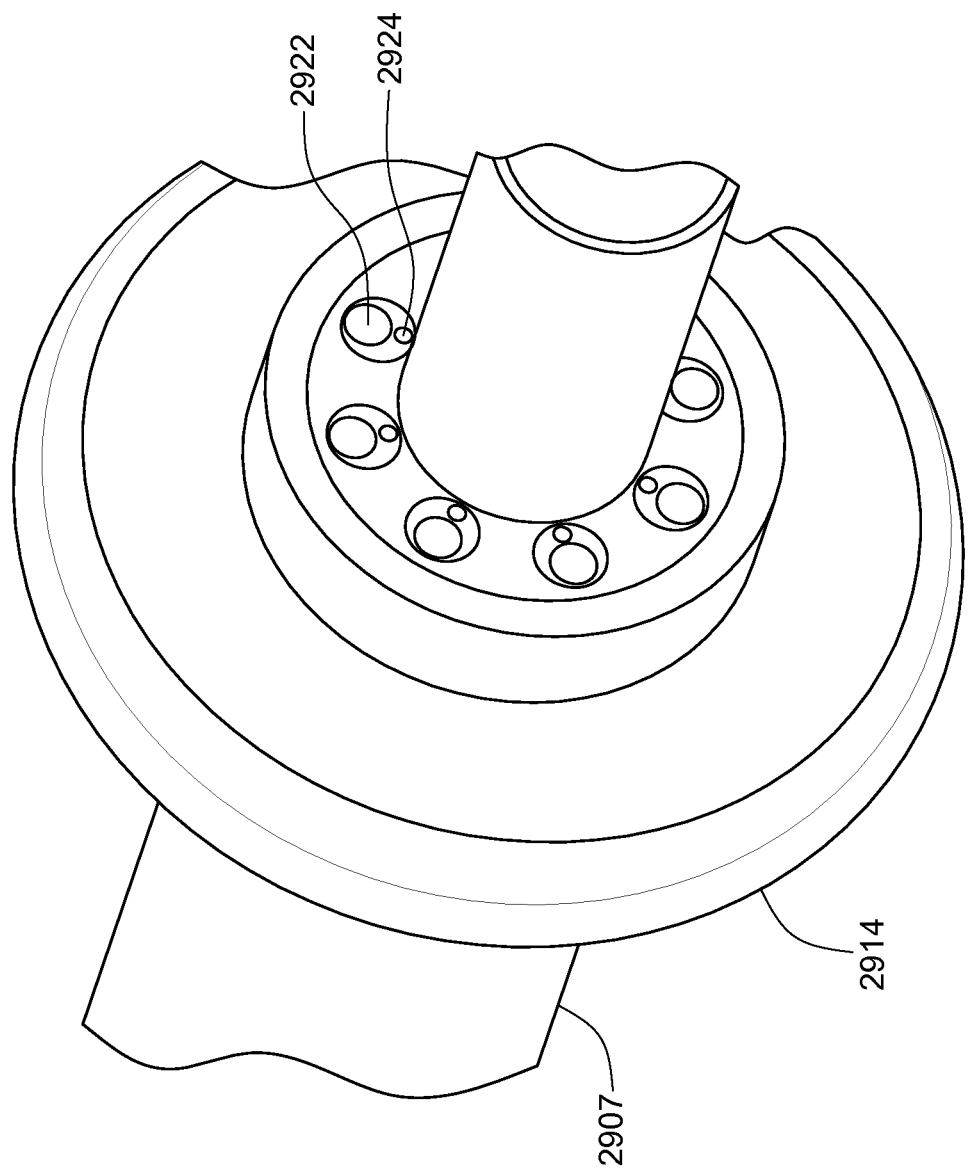
FIG. 29F is a perspective detail of a proximal portion of the apparatus of FIGS. 29A-29D, showing passages for receiving radiation sources therein.

FIG. 29F illustrates a proximal side of the flange 2914 as it may be configured in one embodiment. The flange 2914 may include a series of openings 2922 and 2924 that provide access to the lumens 2918 and 2920 of the members 2906. For example, the opening 2922 may communicate with the lumen 2918 (see FIG. 29D) in a respective elongate member 2906 via a respective lumen (not shown) extending through the body member 2907, while the opening 2924 may communicate with the lumen 2920. As a result, a brachytherapy device and stiffening member (not shown) may be inserted into their respective lumens 2918 and 2920 either before or after the apparatus 2900 is implanted into a target location, as described elsewhere herein. Optionally, the flange 2914 may further include a locking member or ring (not shown) that may secure one or both of the brachytherapy devices and stiffening members relative to the flange 2914.

While not illustrated, the flange 2914 may include indicia (such as alphanumeric symbols, e.g., consecutive numbers like a clock, letters, and the like) to identify the respective openings 2922/2924 around the circumference of the flange 2914. As a result, the physician/oncologist may know which opening 2922 is to receive a particular brachytherapy device in accordance with a desired dose plan, e.g., before or after introducing the apparatus 2900 into a target location. For example, the dose plan may call for a low activity device (device no. "1") to be placed in an area that is proximate the patient's skin. The corresponding opening 2922/2924 may include the same number (no. "1"), or otherwise be identified as the correct opening 2922/2924 to receive the particular low activity device. Thus, with the apparatus 2900 properly oriented within a target location (e.g., with the low activity pathway of elongate member "1" oriented towards the skin), the low activity device may be placed along the low activity pathway, which may reduce the risk of damaging the skin. Correspondingly, higher activity brachytherapy devices may be placed in other specified openings in accordance with the desired dose plan.

Dose planning may be accomplished with the aid of current imaging methods (e.g., CT or ultrasound) and with commercially available dose planning software for either HDR or LDR applications. The timing and general scenario of the dose planning process is at the discretion of the clinical physicist/oncologist. However, one such scenario may include placing the apparatus 2900 into the target tissue region and activating the elongate members 2906 into a deployed configuration. Then, with the aid of imaging (e.g., CT), both the target tissue region and the position of the elongate members 2906 may be delineated. A dose plan may then be developed and, if desired, modified as configuration adjustments are made to the apparatus 2900 and the elongate members 2906.

When the dose plan is optimized, the characteristics of the radioactive sources (e.g., brachytherapy devices) are chosen (e.g., LDR seed activity levels, HDR dwell positions, etc.), and prepared for placement into the apparatus 2900 via the access openings 2922/2924. For example, during LDR brachytherapy, individual pods or other radiation sources may be loaded into respective elongate members 2906 simultaneously or sequentially, thereby providing a three dimensional array of seeds or radiation sources that may remain in the target location for an extended period of time. The seeds may be spaced apart on each pod or have different radioactive intensities, according to the dose plan. For example, the seeds in different portions of the array may also have different lengths and/or spacing along respective elongate members 2906 such that the array is substantially asymmetrical, e.g., radially and/or axially relative to a central axis of the apparatus 2900. Alternatively, during HDR brachytherapy, an individual radiation source may be positioned sequentially along each pathway of the elongate members 2906 for specified exposure times. Optionally, more than one HDR radiation source may be directed along the pathways simultaneously.

While described herein as utilizing separate components, in other embodiments of the apparatus 2900, the elongate members 2906 may extend from the distal hub 2909 proximally all the way to the flange 2914. Thus, the elongate members 2906 may define one or more lumens extending from their respective distal ends 2906a to the flange 2914. The lumens may then receive a brachytherapy device (not shown) having its own stiffening member incorporated therein, see, e.g., device 1202 described elsewhere herein. Alternatively, the elongate members 2906 may already include stiffening members, e.g., within the lumens 2920 or otherwise secured along the elongate members 2906.

Optionally, the stiffening members may provide shielding, similar to other embodiments described elsewhere herein. For example, with generally spherical arrays or radioactive sources, a central region of the array tends to receive greater radioactive exposure than peripheral regions of the array. Shielding placed along inner regions of the elongate members 2906 may reduce overdosing in the central region. For example, FIGS. 32F and 32G show stiffening/attenuating members extending along inner regions of the elongate members 3106 for this purpose.

Figure 30B:
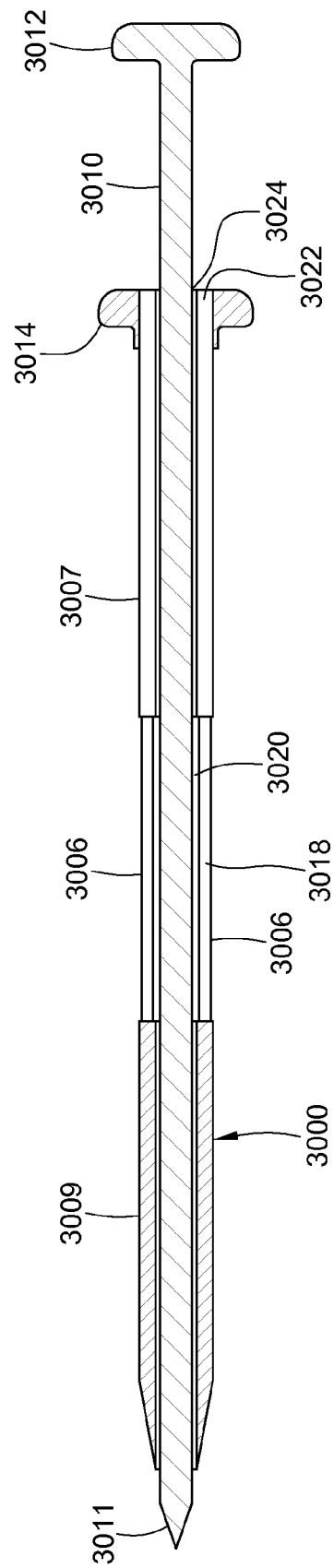
FIGS. 30B and 30C are longitudinal cross-sectional views of the apparatus of FIG. 30A in collapsed and expanded configurations, respectively.
Figure 30C:
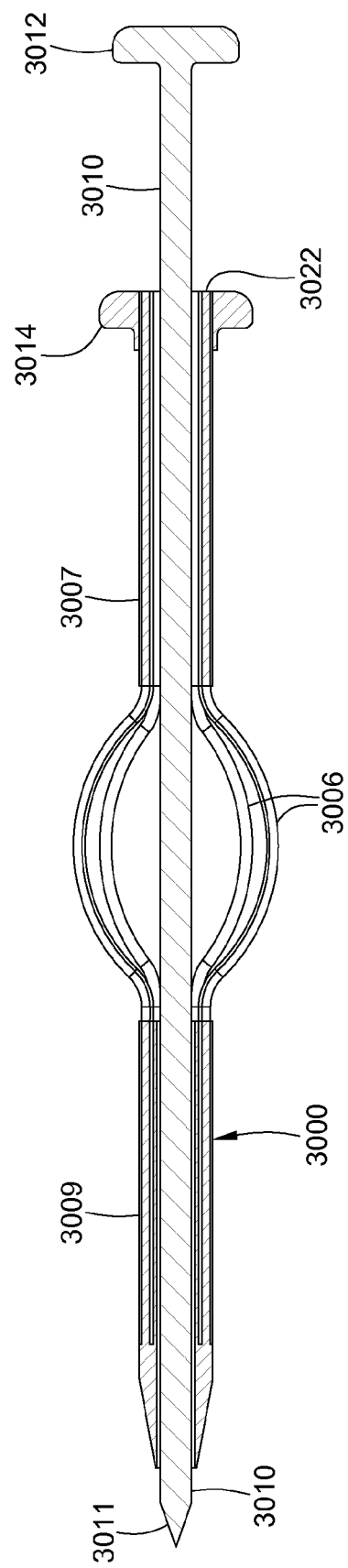

FIGS. 30A-30C illustrate a brachytherapy apparatus 3000 similar in many respects to the apparatus 2900 described above. The apparatus 3000 differs however, in that it is designed to penetrate entirely through a body or tissue structure, e.g., through a breast (not shown). As a result, a distal end of the apparatus 3000 is modified somewhat from the apparatus 2900 to accommodate this application.

FIG. 30A illustrates a side elevation view of the apparatus 3000. Like the apparatus 2900, the apparatus 3000 includes radioactive and flexible elongate members 3006 that are coupled at a proximal end 3006a to a body member 3007 and, at a distal end 3006b, to a hub 3009. A core member 3010, having a button 3012 at one end and a sharp distal tip 3011 at the other, may extend through the body member 3007 and the hub 3009. The sharp distal tip 3011 may permit penetration of tissue by the apparatus 3000 during implantation. Unlike the apparatus 2900, the core member 3010 is not permanently fixed to the hub 3009. Rather, it may slide relative to the hub 3009 and the body member 3007. Optionally, the core member 3010, body member 3007, and/or hub 3009 may include one or more connectors (not shown) for releasably securing the core member 3010, e.g., during implantation, but allowing the core member 3010 to be removed after implantation.

FIG. 30B illustrates a cross-sectional view of the apparatus 3000 in a first collapsed configuration. As illustrated in this view, the elongate members 3006 include lumens 3018, 3020 (e.g., similar to lumens 2918 and 2920 illustrated in FIG. 29D) that either extend through the body member 3007, or that communicate with separate lumens 3022 and 3024 that extend through the body member 3007. As a result, brachytherapy devices, e.g., device 102, 152, 402, 502, and 602 described above, may be threaded into the elongate members 3006 either before or after implantation of the apparatus 3000.

FIG. 30C illustrates a cross-sectional view of the apparatus 3000 in the second expanded configuration. This configuration is achieved by displacing the hub 3009 and body member 3007 towards one another, e.g., using an actuator, such as the button 3012 and flange 3014, or other embodiments described herein.

In use, while in the collapsed configuration shown in FIG. 30B, the apparatus 3000 may be inserted into the body, e.g., breast or other tissue structure (not shown), until the elongate members 3006 are disposed within a cavity or other target location (also not shown). The apparatus 3000 may be inserted until the hub 3009 extends out the opposite (distal) side of the breast. The sharp tip 3011 of the core member 3010 may be used to penetrate tissue on either side of the cavity during implantation. Optionally, once the apparatus 3000 is passed entirely through the breast, the core member 3010 may be removed from the apparatus 3000, e.g., by pulling the core member 3010 out the proximal end of the apparatus 3000. At this point, the physician may grasp the body member 3007 and the hub 3009 and push the two components 3007, 3009 towards one another. As this occurs, the elongate members 3006 expand radially outwardly towards the cavity walls, e.g., towards the expanded configuration illustrated in FIG. 30C.

When fully deployed, the body member 3007 and the hub 3009 may be secured to the body, e.g., to the skin, with tape, sutures, or the like. Alternatively, a locking member (not shown) may be inserted through the body member 3007 and/ or the hub 3009 that holds the two components relative to one another (e.g., a long plastic threaded bolt with nut, not shown). In another alternative, movement of the body member 3007 and/or hub 3009 may be limited, e.g., using ratchets, detents, and the like (not shown) that may fix the body member 3007 and hub 3009 relative to one another, but may be overcome to move the body member 3007 and/or hub 3009, as described elsewhere herein.

The brachytherapy devices (not shown) may be carried by the elongate members 3006 when the apparatus 3000 is introduced, or the apparatus 3000 may be introduced without the brachytherapy devices. If the brachytherapy devices are not included in the apparatus 3000 at implantation, a radiation oncologist or similarly trained clinician may then insert the brachytherapy devices through the lumens 3022 or other pathways along the elongate members 3006. Alternatively, automated systems may be provided for delivering one or more radiation sources along the pathways. In other embodiments, the brachytherapy devices may be preloaded into the apparatus 3000 before implantation, either removably or permanently carried by the elongate members 3006.

FIGS. 31A-31F illustrate an in-situ actuatable brachytherapy treatment apparatus 3100, in accordance with yet another embodiment. The apparatus 3100 includes a series of radioactive and elongate flexible members 3106, that are deployable from a first collapsed, e.g., straight, configuration (shown in FIG. 31A), to a second deployed e.g., curvilinear, configuration (shown in FIG. 31B). In the collapsed configuration, the members 3106 may be collapsed against the apparatus 3100 (e.g., are generally parallel to a central longitudinal axis of the apparatus 3100), e.g., to minimize size for implantation. However, in the deployed configuration shown in FIG. 31B, at least a portion of the elongate members 3106 expand radially towards and/or into the outer walls of a body cavity, e.g., a lumpectomy cavity (see, e.g., FIGS. 32D-32G). As a result, the apparatus 3100 is generally fixed within the tissue surrounding the cavity.

In the illustrated embodiment, the elongate members 3106 may be configured in two distinct groups best viewed in FIG. 31B. The first or outer group includes elongate members identified by reference numeral 3106*a* and forms a football or watermelon-shaped boundary, as shown in FIG. 31B. The second or inner group includes elongate members identified by reference numeral 3106*b* and defines a similar, but smaller, watermelon shape. In the illustrated embodiment, the outer group includes seven separate members 3106*a*, while the inner group includes three separate members 3106*b*. However, other embodiments may vary the number of elongate members 3106 in either group. The elongate members 3106*a* and 3106*b* may be referred to generically, or collectively, as elongate members 3106.

The elongate members 3106 may be attached at a first (e.g., proximal) end to a body member 3107. However, the elongate members 3106*a* may be attached at their respective second (e.g., distal) ends to a distal hub 3109, while the distal ends of the members 3106*b* may be attached to a separate floating hub 3108.

The apparatus 3100 may further include a core member 3110 that is attached to the distal hub 3109 and extends out the proximal side of the body member 3107. The core member 3110 may be fixed to the distal hub 3109, yet pass with clearance through openings in both the body member 3107 and the floating hub 3108. As a result, the body member 3107 and the floating hub 3108 may slide along the core member 3110, as further described below. The core member 3110 may function as a tension member. As a result, it may be generally rigid or, alternatively, a tension-only member such as a cable or a suture.

Each of the elongate members 3106 may include a stiffening member, which in the illustrated embodiments, is an elastic flat wire 3112. The wire 3112 ensures that the elongate members 3106 expand and contract in the desired orientation (e.g., without twisting). The wire 3112 may also provide some integrity to the elongate members 3106, e.g., to ensure that the elongate members 3106 may be forced outwardly into the cavity walls with sufficient radial and lateral stability. While not wishing to be bound to any particular material, the wires 3112 may, in one embodiment, be made from tempered stainless steel or a shape memory alloy such as nitinol or the like. Such materials may permit the apparatus 3100 to invaginate the lumpectomy walls and/or remain in a substantially secure geometry (see FIGS. 32D-32G), while also permitting collapse of the apparatus 3100 to its pre-deployed configuration at therapy completion.

Individual tubes 3114 may be attached to respective flat wires 3112. The tubes 3114 are operable to receive a brachytherapy device (not shown), as already described elsewhere herein, e.g., devices similar to devices 102, 152, 402, 502. Alternatively, the tubes 3114 may be made to receive individual radioactive sources, e.g., seeds 108 described elsewhere herein, and spacers, which may be loaded into the tubes 3114 during or before a treatment. Thus, the tubes 3114 may form the outer surface of the actual brachytherapy devices. The tubes 3114 may be made from most any biocompatible material that is capable of retaining the radioactive sources or a pre-assembled brachytherapy device, e.g., fluoropolymers, such as fluorinated ethylene-propylene ("FEP"), nylon, and polyurethane.

FIG. 31C illustrates a side elevation view of the apparatus 3100, while FIG. 31D illustrates an end view. These two views illustrate a variation of the body member 3107 that includes a flange 3111 formed thereon or attached thereto. This optional flange 3111 may be beneficial to the physician during the implantation and/or removal process, by providing a location to be gripped during positioning of the core member 3110.

Figure 31A:
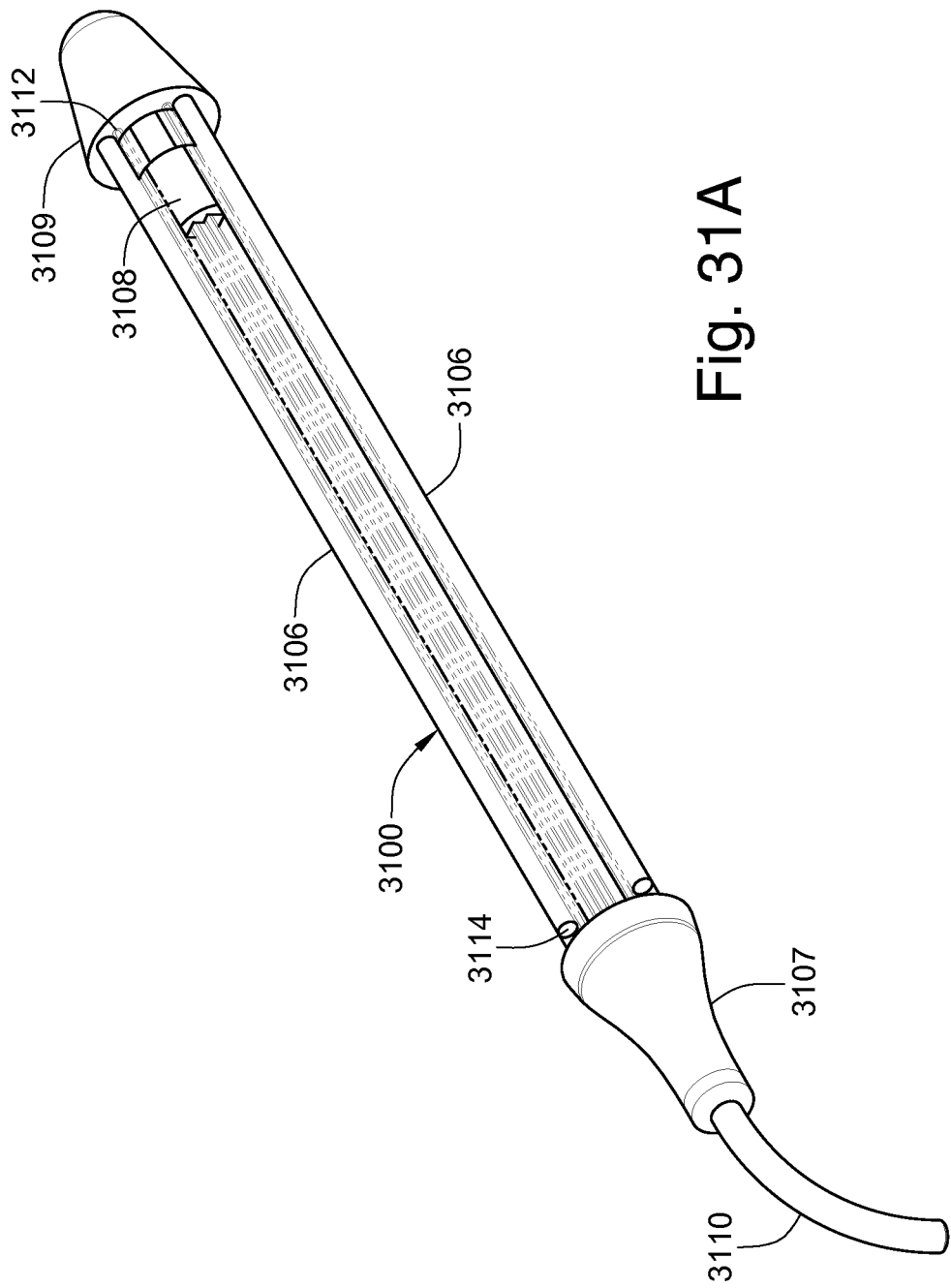
Figure 31E:
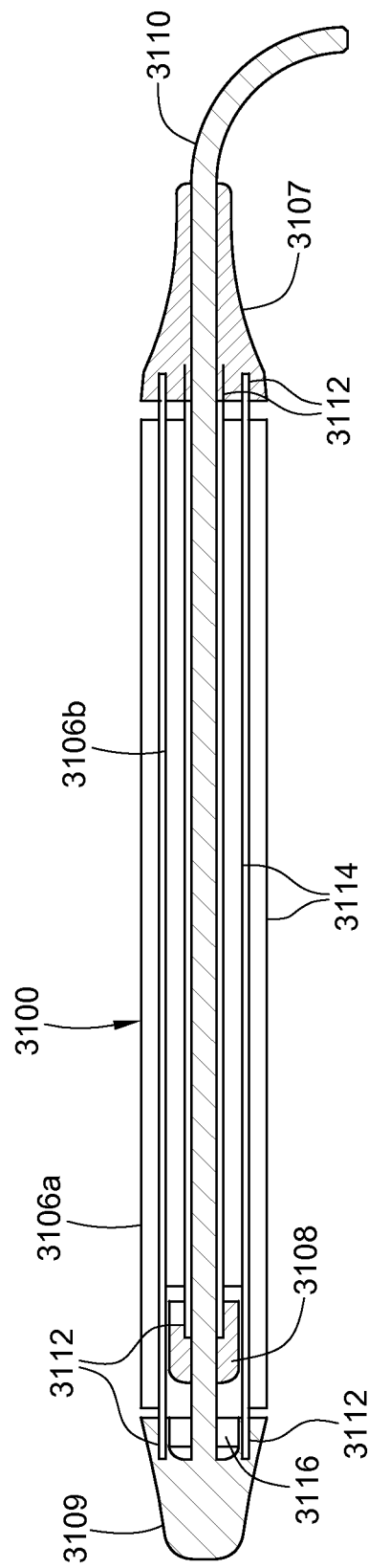
FIGS. 31E and 31F are longitudinal cross-sectional views of the apparatus of FIGS. 31A-31B in the collapsed and expanded configurations, respectively.

FIG. 31E is a staggered longitudinal cross-sectional view of the apparatus 3100 in the collapsed configuration (by staggering the cross-section, this figure illustrates sections of two elongate members 3106a and two elongate members 3106b that would not otherwise appear in a straight cross-section). In this view, the attachment of the core member 3110 to the distal hub 3109 is clearly shown, as is the fixation of the flat wires 3112 with the distal hub 3109, the floating hub 3108, and the body member 3107.

FIG. 31E further illustrates a pocket 3116 formed within the distal hub 3109. The pocket 3116 provides a stop surface that limits axial movement of the floating hub 3108 when the apparatus 3100 is in the deployed configuration. While illustrated as a pocket 3116, another embodiment could be configured to have the floating hub 3108 merely contact a flat inside face of the distal hub 3109.

Figure 31F:
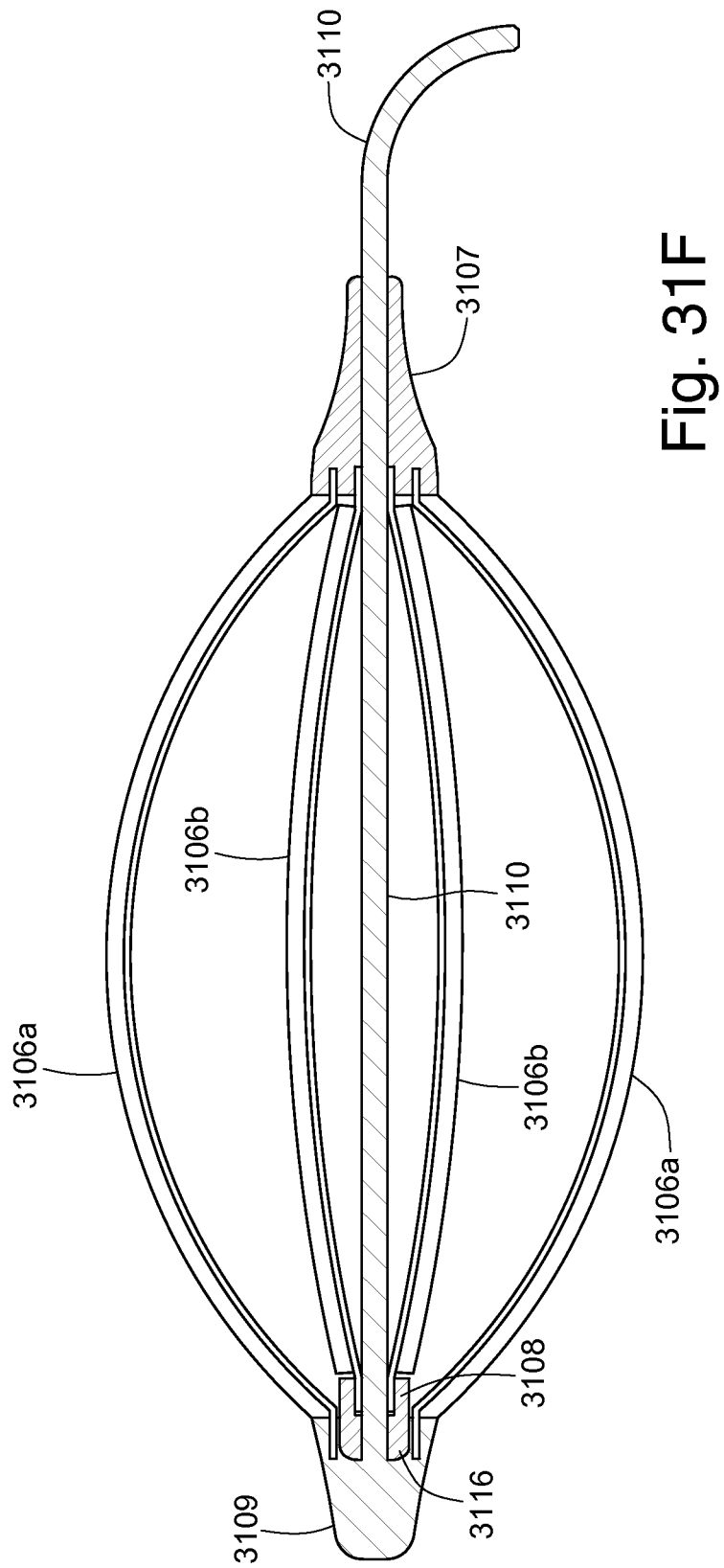

FIG. 31F is a staggered longitudinal cross-sectional view, similar to FIG. 31E, with the apparatus 3100 in the deployed configuration. As shown in this view, the deployed configuration may be achieved by applying a tensile force to the tail portion of the core member 3110 while holding the body member 3107 in place. Applying such a tensile force causes the distal hub 3109 to move towards the body member 3107. As this movement occurs, the elongate members 3106a begin to bow outwardly as illustrated. Once the floating hub 3108 contacts the pocket 3116, the members 3106b also begin to bow outwardly. Further tensioning of the core member 3110 may result in outward movement of both the elongate members 3106a and 3106b. By changing the axial position of the core member 3110 relative to the body member 3107, a variety of deployed diameters are possible. When the apparatus 3100 is deployed to the desired diameter, a clamp or similar device (not shown) may be crimped around the core member 3110 immediately adjacent the body member 3107 to prevent the core member 3110 from sliding relative to the body member 3107.

Other methods for securing the apparatus 3100 in the desired diameter may include a threaded nut and bolt assembly (not shown). For example, the body member 3107 may be split and externally threaded like a conventional machinist's collet (not shown). A nut (not shown) may be threaded around the collet and tightened to hold the core member 3110, thereby holding the apparatus 3100 at the desired degree of expansion. Alternatively, the core member 3110 may include a series of closely spaced holes or pockets (not shown) residing along the region where the core member 3110 protrudes from body member 3107. A cotter pin and the like (not shown) may be placed at the desired hole or pocket to hold the apparatus 3100 with the desired degree of expansion.

Figure 32A:
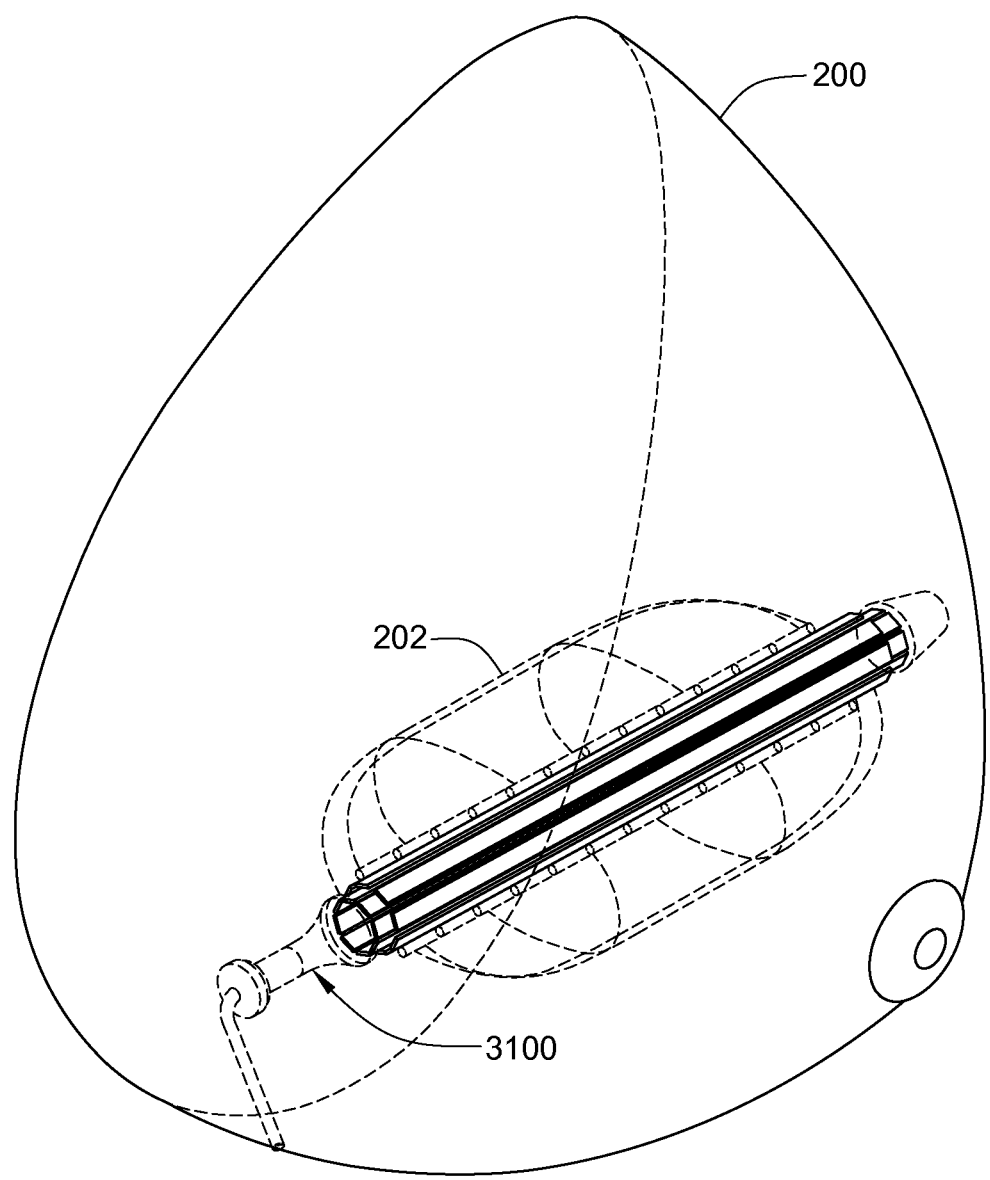
FIGS. 32A-32C are perspective, front, and side views, respectively, showing a method for using the apparatus of FIGS. 31A-31F to delivery brachytherapy to a cavity within a body, e.g., a lumpectomy cavity of a breast.
Figure 32B:
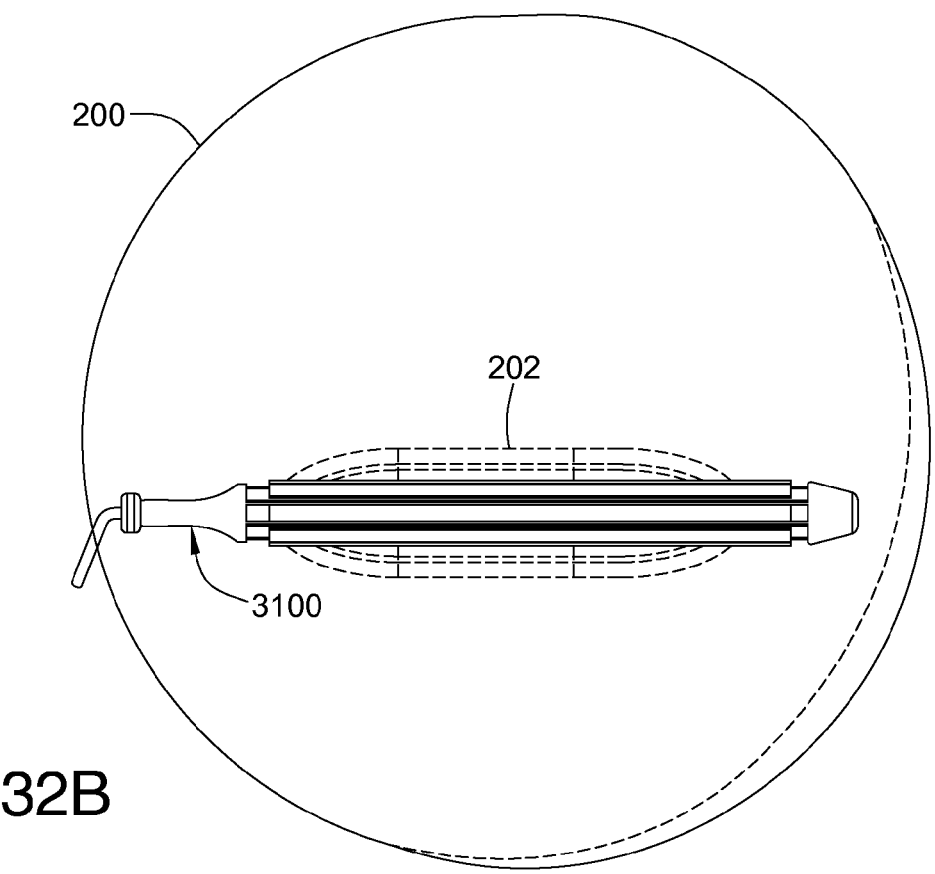
Figure 32C:
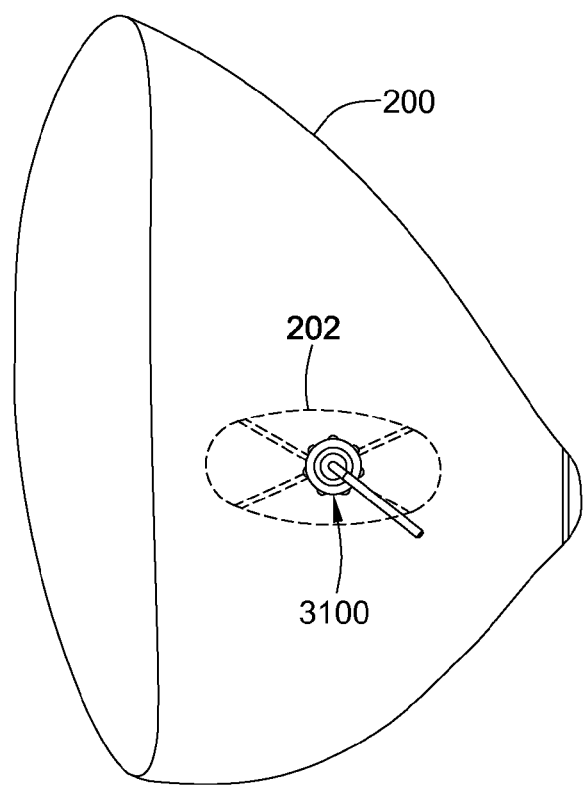
Figure 32D:
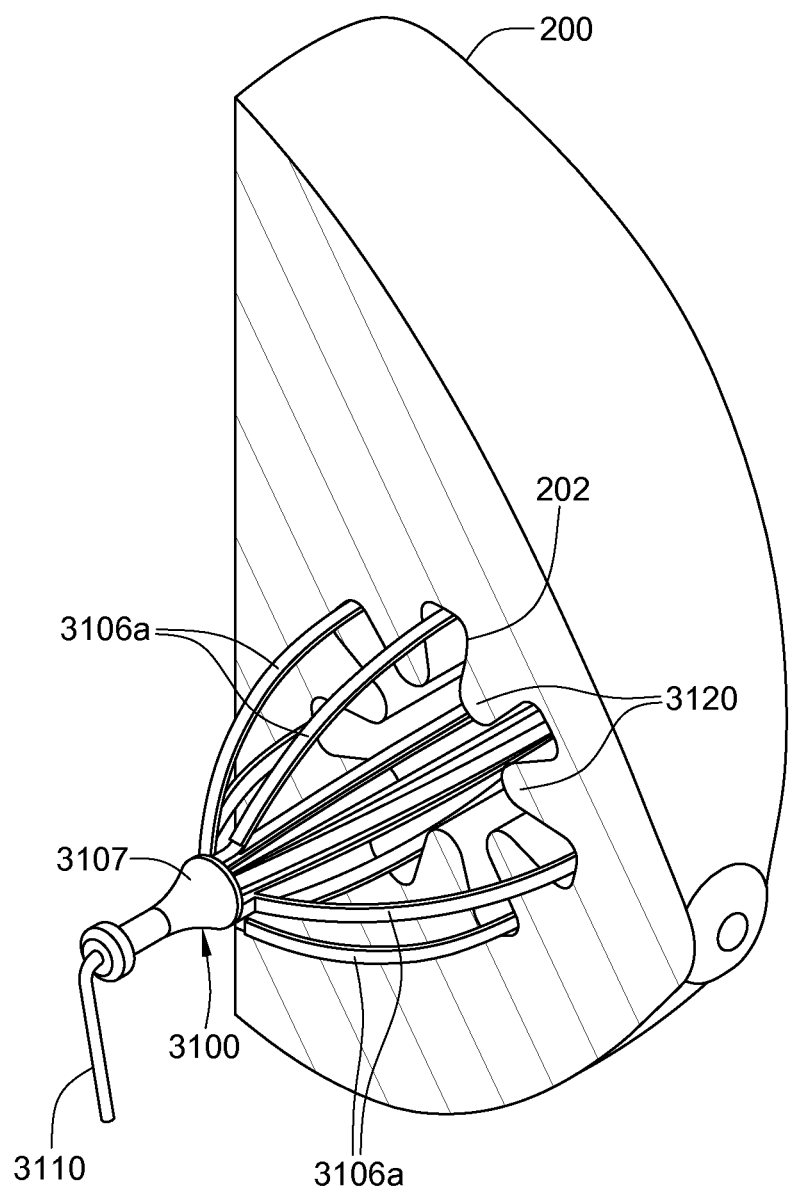
FIGS. 32D and 32E are perspective and side cross-sectional views of the breast of FIGS. 32A-32C, showing the apparatus in the expanded configuration.
Figure 32E:
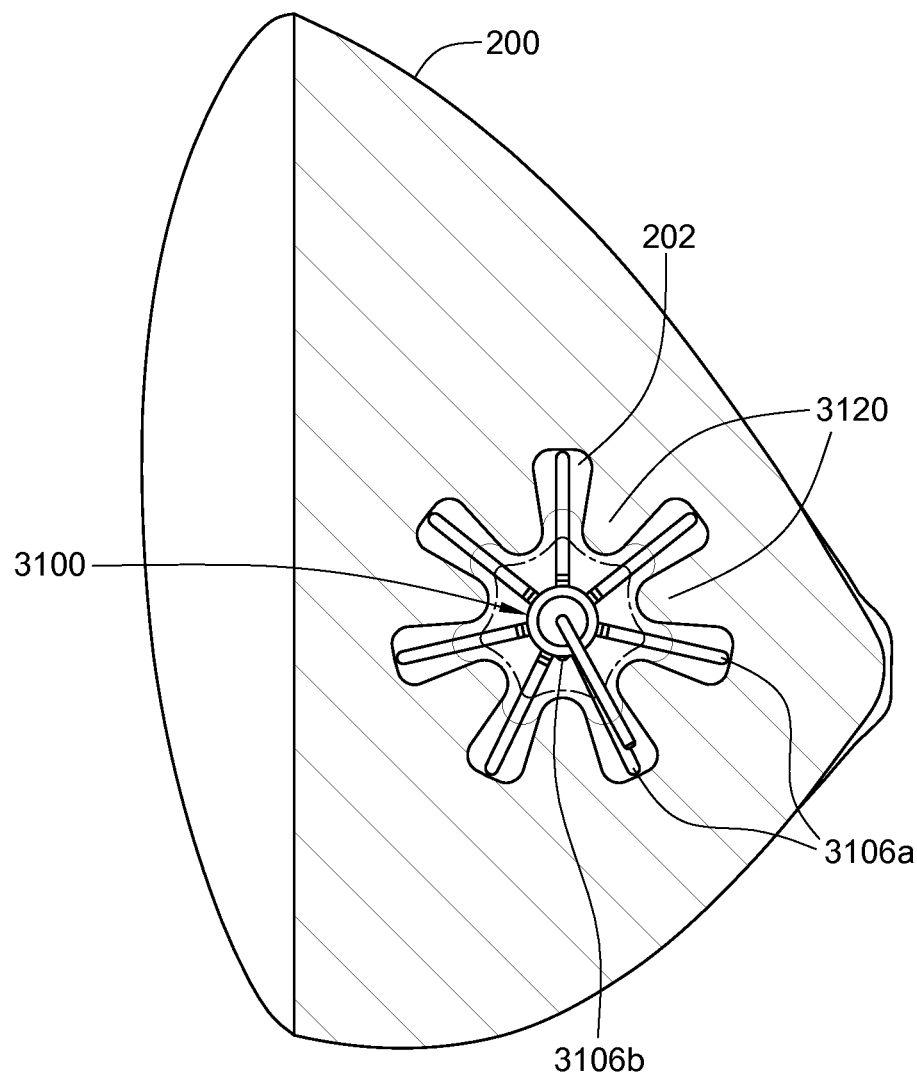
Figure 32F:
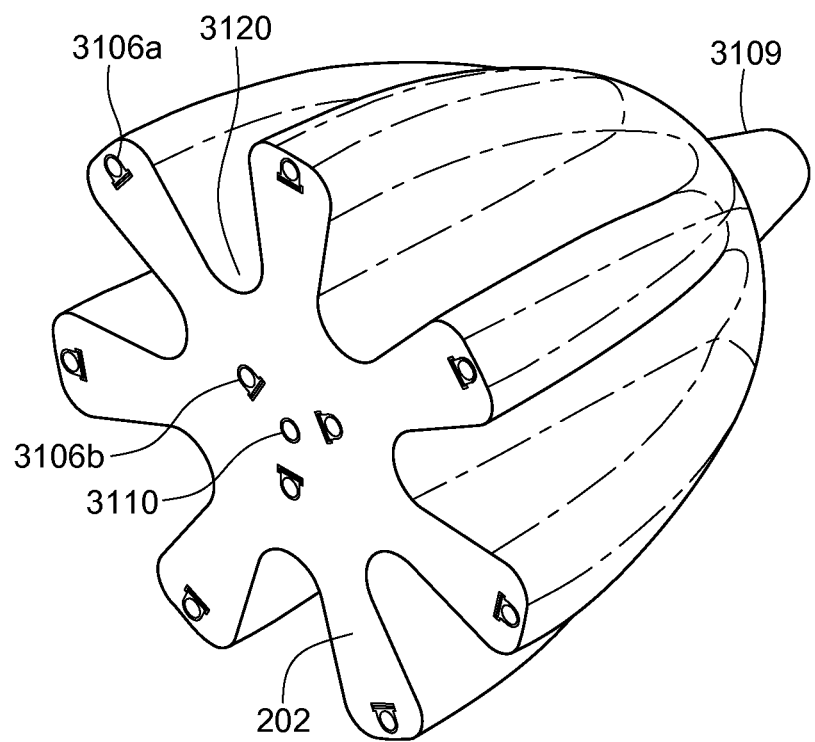
FIG. 32F is a cross-sectional view of the breast cavity of FIGS. 32A-32E, with the apparatus in the deployed configuration.
Figure 32G:
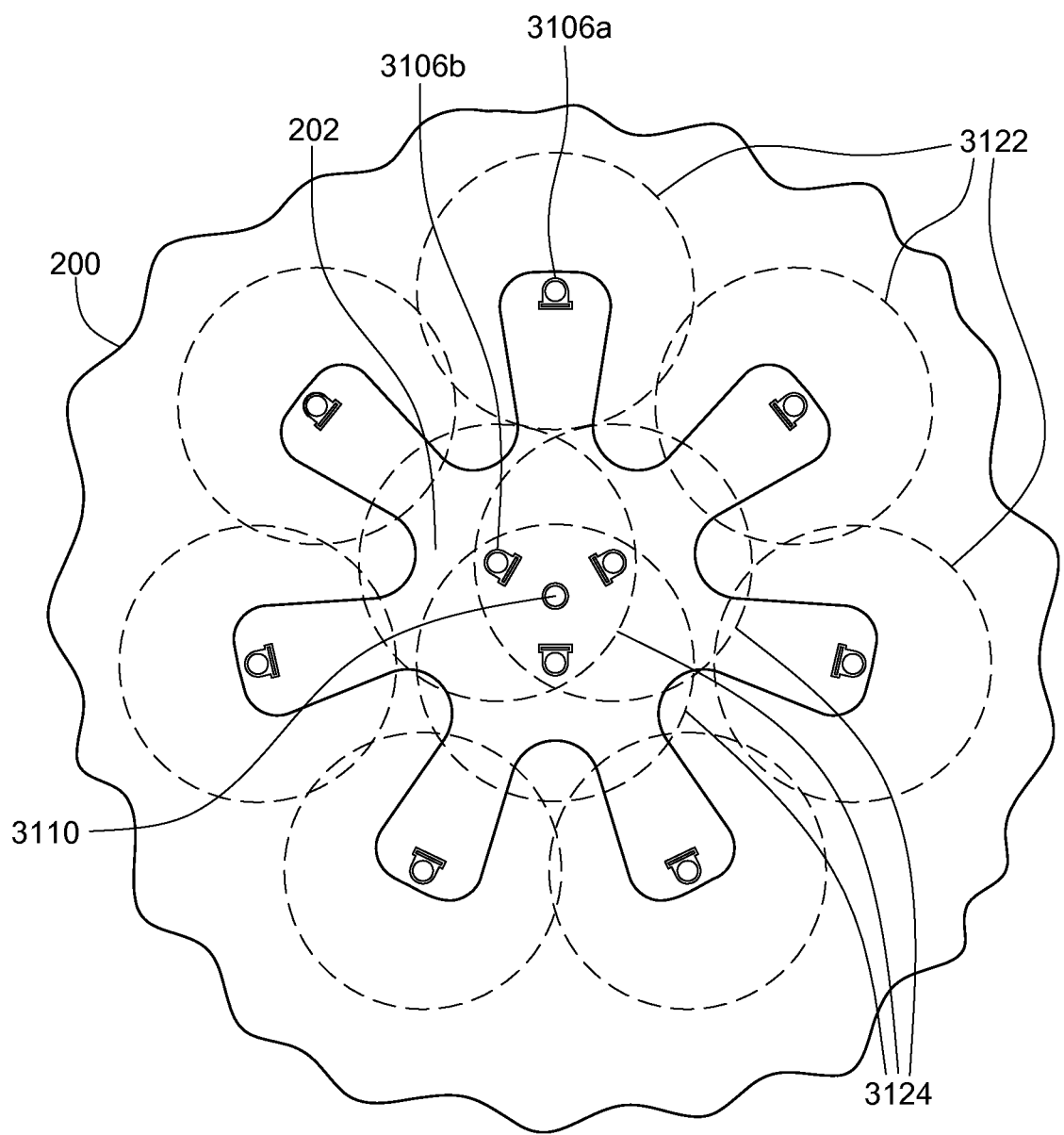
FIG. 32G is a cross-sectional detail of the breast cavity of FIG. 32F, showing exemplary radiation coverage provided by the apparatus.

FIG. 32A-32F illustrate a method for using the apparatus 3100 of FIGS. 31A-31F. FIG. 32A illustrates a perspective view of a portion of a body (e.g., a breast 200) having a cavity (e.g., a lumpectomy cavity 202) formed therein by removal of cancerous tissue. The apparatus 3100 is shown inserted and in its collapsed position. The apparatus 3100 may be inserted via an existing incision, e.g., the incision used to perform the lumpectomy, or via a new incision created for delivering the apparatus 3100. FIGS. 32B and 32C illustrate a front and side view of the breast 200, respectively, with the collapsed apparatus 3100 shown in place within the cavity 202.

Once the apparatus 3100 is in the desired position, the core member 3110 may be pulled by the physician while the body member 3107 is held against the breast incision. The length of the body member 3107 may be sufficient to extend to the skin surface, regardless of the distance from the skin to the lumpectomy cavity 202. As the apparatus 3100 deploys, it may tend to center itself within the cavity 202, e.g., as shown in FIGS. 32D-32F.

Figure 32H:
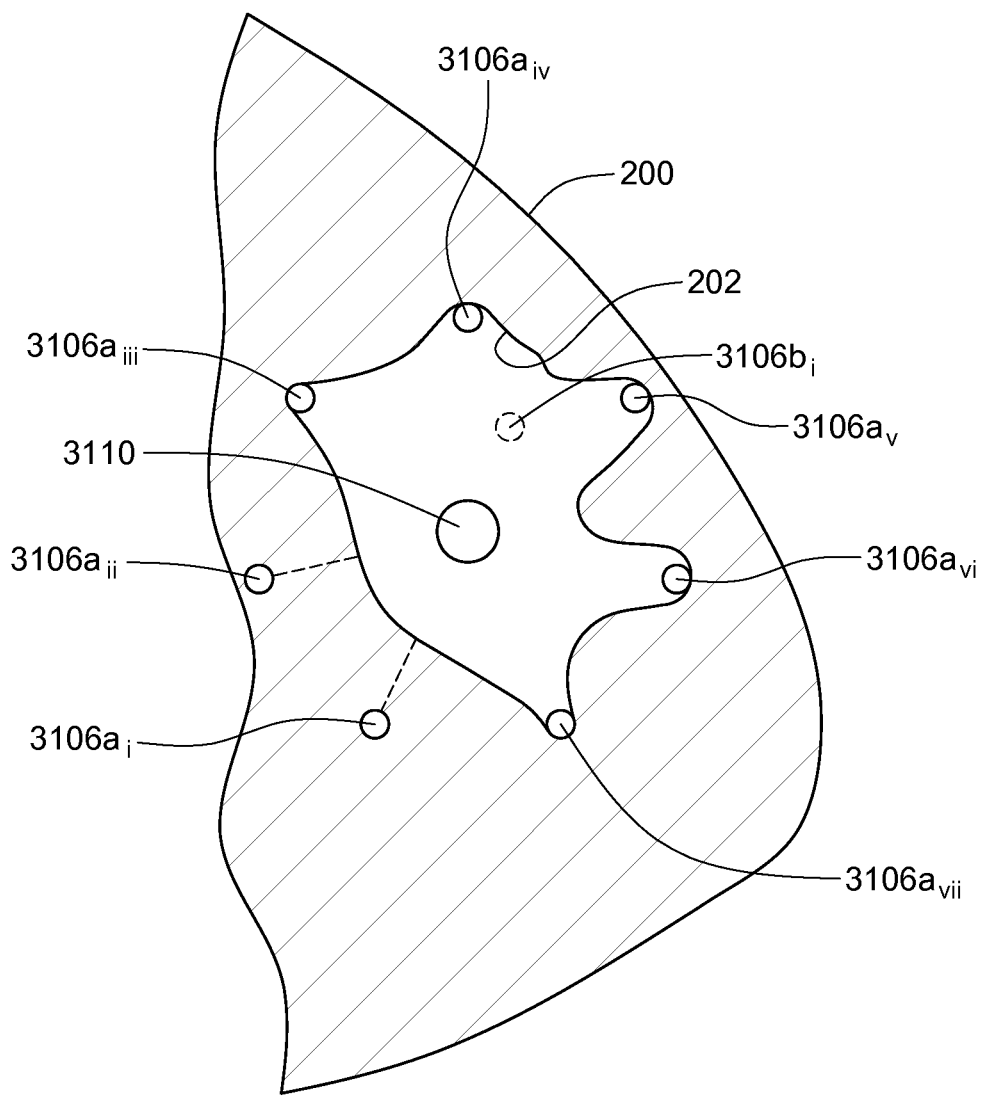
FIG. 32H is a cross-sectional view of an apparatus deployed within a lumpectomy cavity within a tissue structure, showing penetration of elongate members of the apparatus into surrounding tissue.

Alternatively, the apparatus 3100 may also move within the cavity during expansion of the apparatus 3100 due to varying amounts of penetration of the elongate members within the adjacent tissue. For example, as shown in FIG. 32H, the region adjacent the skin is less prone to penetration by the elongate members 3106 than the tissue underlying the cavity 202. As shown in FIG. 32H, the elongate members 3106 may be sufficiently small such that at least some of the elongate members (e.g., elongate members $3106_i$, $3106_{ii}$) may cut, tear, or otherwise penetrate through tissue surrounding the cavity 202, thereby allowing radiation to be delivered deeper into tissue than if there was no penetration of the elongate members 3106 into the adjacent tissue. This ability of the elongate members 316 to penetrate the tissue and, in some cases be circumferentially surrounded by adjacent tissue (e.g., as shown in FIG. 32H), effectively provides an interstitial form of radionuclide placement for the apparatus 3100.

FIG. 32D illustrates a perspective cross section of the breast 200 and cavity 202 with the apparatus 3100 shown in its full expanded configuration therein. As illustrated in this view, the elongate members 3106a may push beyond the walls of the cavity 202, resulting in invagination of the tissue around the elongate members 3106a, e.g., portions of wall tissue 3120 may flow, extrude, or extend inwardly between the elongate members 3106a to substantially surround the elongate members. In one embodiment, the wall tissue 3120 may extend radially inwardly about 0.7 centimeter from the outermost elongate members 3106a. However, actual invagination distances may vary based on several variables, including, for example, apparatus size and shape, cavity size and shape, and tissue properties. The elongate members 3106b preferably remain within the diameter defined by the innermost portions of the extruded wall tissue 3120. As can be appreciated from this view, invagination may result in substantial fixation of the apparatus 3100 relative to the surrounding tissue, and may distort the cavity 202 until it generally conforms to the shape of the apparatus 3100.

In one embodiment, a vacuum system (not shown) may be coupled to the apparatus 3100, e.g., to apply a vacuum pressure to the cavity 202 to increase the degree of tissue invagination. Such a vacuum may be left active during all or part of the implantation period, or may be disconnected immediately following treatment, e.g., for HDR therapy.

In still other embodiments, the elongate members 3106a may be conductive or otherwise excitable, such as by radio frequency (RF). Such activation of the elongate members 3106a after deployment may allow the elongate members 3106a to cut into the cavity walls, and therefore penetrate deeper into the surrounding tissue, which may further increase the degree of invagination.

FIG. 32E illustrates a section view of the apparatus 3100 implanted and fully deployed. The inwardly extending wall tissue 3120 is clearly visible in this view. FIG. 32F illustrates a partial perspective section view of the cavity 202 with diagrammatic representations of the elongate members 3106 shown therein in their deployed configuration.

FIG. 32G illustrates a cross-sectional view of the cavity 202 with the apparatus 3100 in its deployed configuration (and with some structure of the apparatus 3100 removed for clarity). This view further illustrates exemplary dose clouds provided by the brachytherapy devices contained within the elongate members 3106. For example, each of the elongate members 3106a may yield a dose cloud generally represented by circles 3122, while each of the elongate members 3106b may yield a simplified dose cloud generally represented by circles 3124. The circles 3122 and 3124 represent the effective two-dimensional cloud boundaries at a particular cross section, i.e., the dose clouds may create two layers of radiation, an outer layer around elongate members 3106a and an inner layer around elongate members 3106b. The actual cloud produced by each of the elongate members 3106 would be generally in the form of a curvilinear cylinder.

The three-dimensional cumulative effect of all the radiation sources in each of the two layers of elongate members 3106 is a therapeutic dose cloud shell that extends over the volume of tissue that immediately surrounds the cavity 202. With proper dose mapping and dose selection, the three-dimensional dose cloud shell may typically expose an adequate margin of tissue (e.g., one centimeter (1 cm) or more beyond the wall of the cavity 202) to the proper therapeutic dose. Because of the interstitial nature of many of the radionuclide sources, a therapeutic dose may be delivered to the desired region of tissue with lower risk of overdose effects that might be obtained if all the radionuclide sources resided within or at the edge of the cavity 202 (e.g., as may occur with a balloon applicator or other intracavitary applicator).

In addition, unlike a balloon applicator, individual elongate members 3106 may apply local discrete radial forces to surrounding tissue. A balloon applicator has a continuous surface and, consequently, applies a relatively continuous radial force along its surface to the adjacent cavity surface. In contrast, because the elongate members 3106 are intermittently spaced with voids therebetween, each elongate member 3106 may apply highly localized radial forces against the cavity surface, leading to invagination of tissue between one or more adjacent elongate members during expansion.

Turning to FIG. 32H, in some applications, one or more of the elongate members $3106a_{i_v}$, $3106a_v$ may be located towards a relatively thin region of tissue adjacent the cavity 202, e.g., adjacent the patient's skin. If pods or other radiation sources having uniform radiation intensities are introduced into each of the elongate members 3106, there is a risk of overexposing or "burning" such thin tissue regions or the skin itself. For this reason, a dose plan may recommend introducing a radiation source into the elongate members $3106a_{i_v}$, $3106a_v$ that has a relatively lower radiation intensity, or may even have one or more seeds "turned off" (i.e., by providing nonradioactive spacers between sources along at least a portion of one or both of the elongate members $3106a_{i_v}$, $3106a_v$).

Optionally, the dose plan may recommend delivering radiation to the thin region from an inner layer of elongate members. For example, as shown in FIG. 32H, a single elongate member $3106b_i$ may be provided that is disposed between the elongate members $3106a_{i_v}$, $3106a_v$ and closer to the central axis of the core member 3110. A radiation source may be introduced into the single elongate member $3106b_i$ to deliver radiation past the elongate members $3106a_{i_v}$, $3106a_v$ and into the thin region of tissue. Thus, an inner layer of elongate members may be provided to enhance delivering radiation locally according to a desired dose plan.

In the embodiment illustrated in FIGS. 32D-32H, the elongate members 3106a may be configured to be spaced about one centimeter (1 cm) from each other (when fully expanded) at their largest diameter (which may be up to about three centimeters (3 cm)). Moreover, the radioactive sources, e.g., seeds 108 as described elsewhere herein, may yield a therapeutic dose cloud (circle 3122 and 3124) about the wires of approximately one centimeter (1 cm). As a result, the apparatus 3100 may provide radiation to all, or substantially all, of the cavity wall and surrounding tissue as represented by the circles 3122 and 3124 in FIG. 32G. It is noted that the radiation sources used with the apparatus 3100 may be low dose rate sources or, alternatively, high dose rate sources (such as Iridium or Ytterbium) that are delivered intermittently.

At the completion of brachytherapy treatment, the apparatus 3100 may be returned to its collapsed configuration, and the apparatus 3100 removed from the breast 200 via the insertion incision.

Figure 33A:
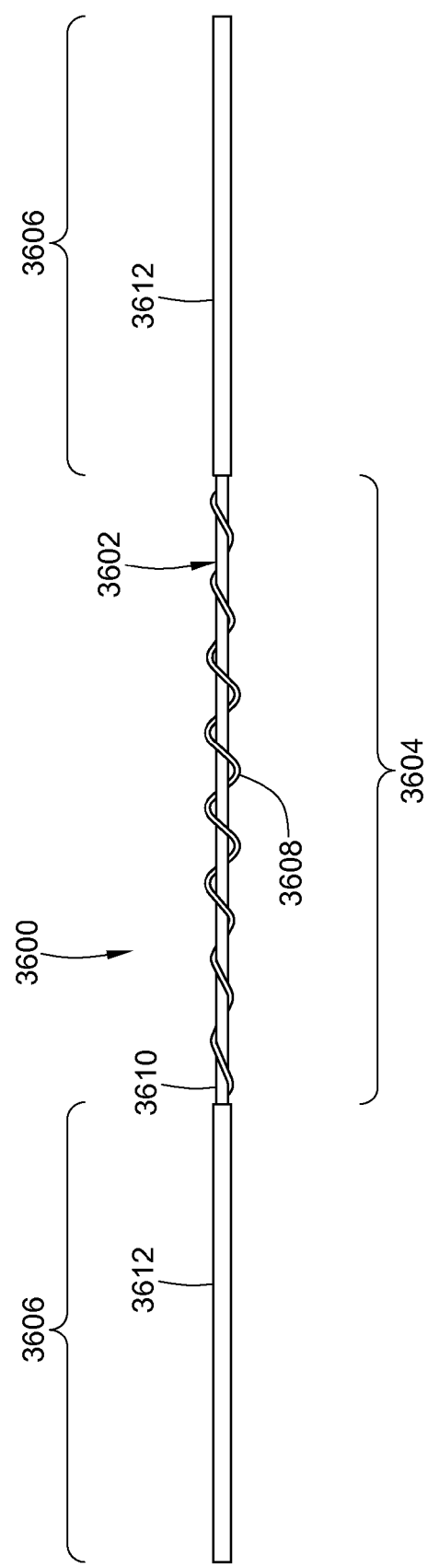
FIGS. 33A and 33B are perspective views of a fifth exemplary embodiment of an expandable brachytherapy apparatus in collapsed and expanded configurations, respectively.

FIGS. 33A-33G illustrate an alternative embodiment of an intracavitary brachytherapy apparatus 3600. The apparatus 3600 may include a brachytherapy device 3602 having a therapy delivery portion 3604 and external, e.g., tail, portions 3606. As shown in FIG. 33A, the therapy delivery portion 3604 may be formed by a deformable and elongate radioactive source, e.g., coil member 3608. The coil member 3608 may form a helical coil wound about an elongate core member 3610. At least one end of the coil member 3608 (e.g., a proximal end) may be secured to an attachment member (e.g., a sleeve 3612) that translates and/or rotates about the core member 3610. This configuration provides a low profile device that may be inserted into a target region, e.g., lumpectomy cavity (not shown), via a relatively small incision.

Figure 33B:
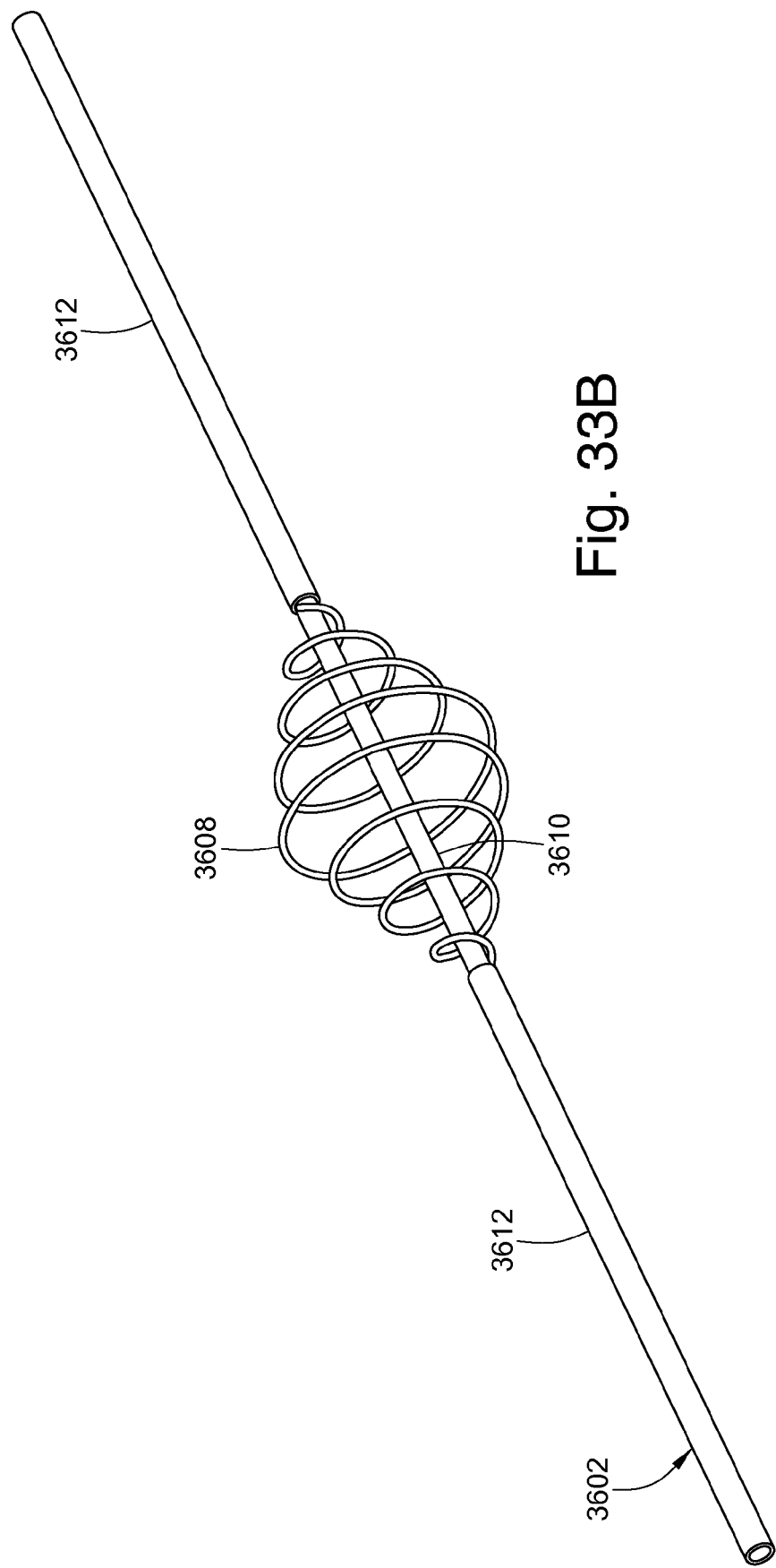
Figure 33F:
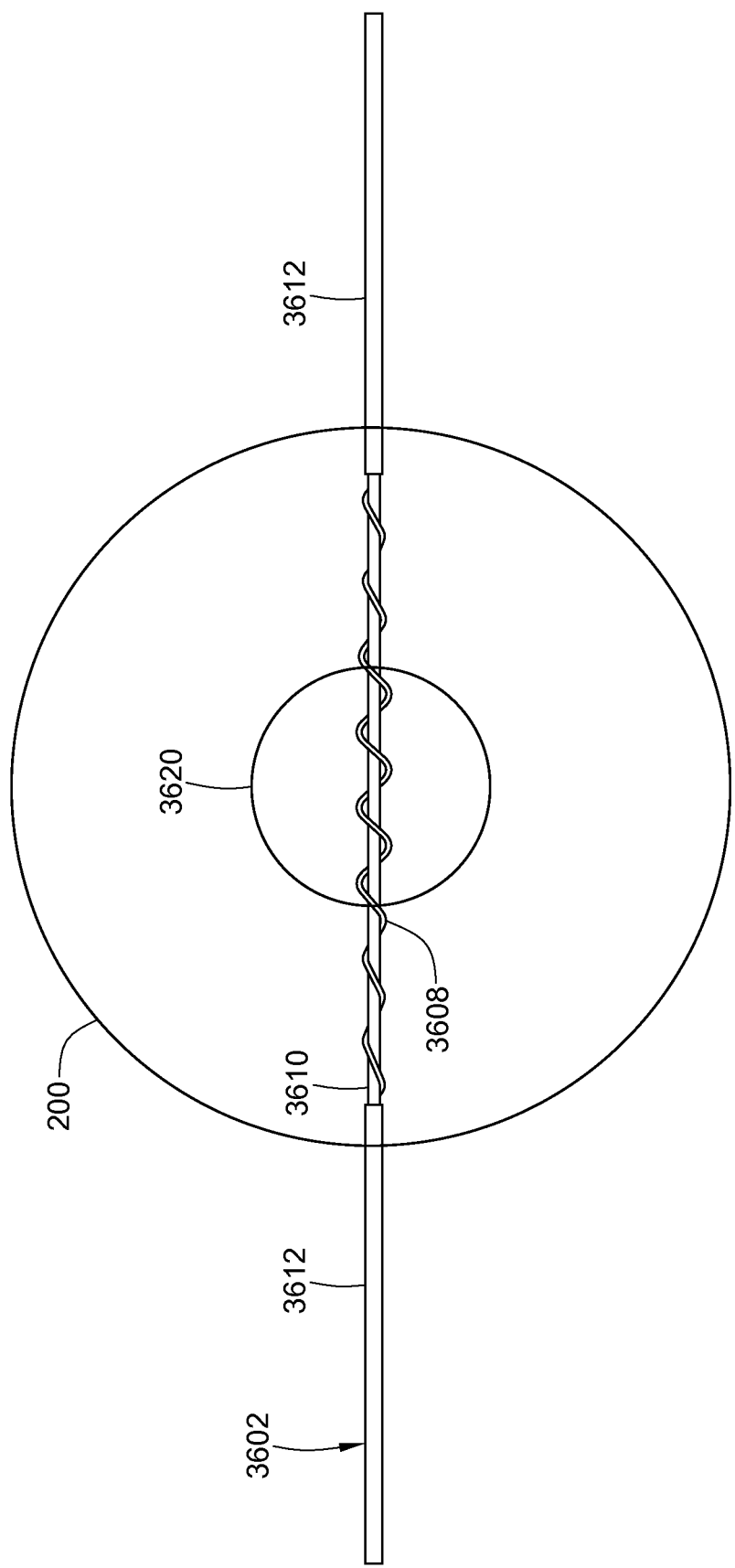
Figure 34:
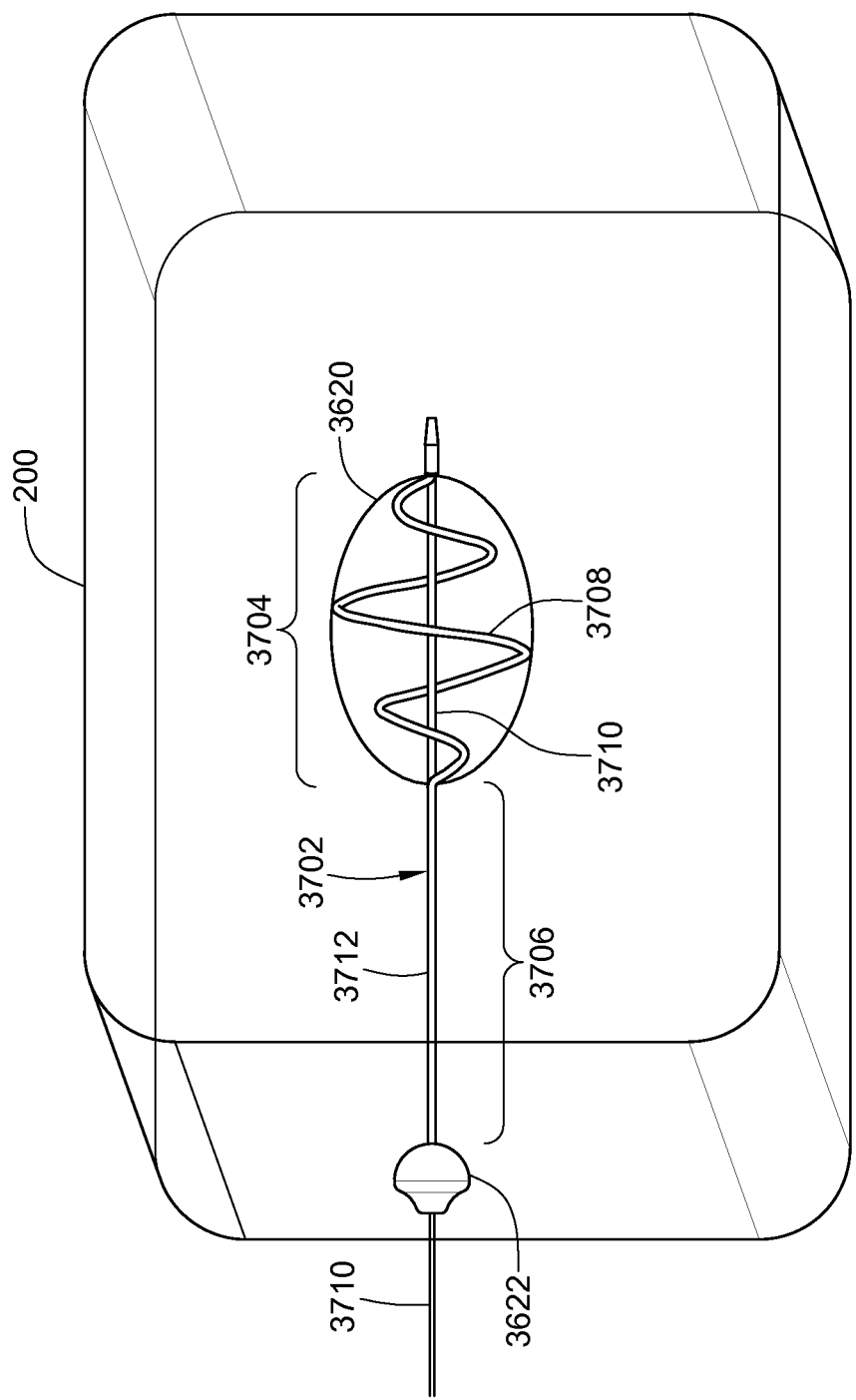
FIG. 34 is a cross-sectional view of a tissue structure, showing a sixth exemplary embodiment of an expandable brachytherapy apparatus implanted and expanded within a cavity of the tissue structure.

Once in place, however, the coil member 3608 may be deployed to form a spiral pathway within the cavity as shown in FIG. 33B. To deploy the device 3602, the sleeves 3612, which may extend outside of the body after implantation, may be rotated about the core member 3608 relative to one another. Relative rotation of the sleeves in one direction may cause the coil member 3608 to expand, i.e., move away, from the central core member 3610. Relative rotation of the sleeves 3612 in the opposite direction may similarly cause the coil member 3608 to contract around the core member 3610. The greater the expansile rotation, the more radial force may be exerted against the walls of the lumpectomy cavity. Greater force exerted against the walls of the lumpectomy cavity may result in a higher degree of invagination of the breast tissue within the turns of the expanded coil member 3608.

In addition to rotational movement of the sleeves 3612, the sleeves may also translate axially relative to the core member 3610. Axial translation permits adjustment in length of the coil member 3608 when in its expanded configuration. Due to the ability to independently control the axial length and the diameter (and hence the expansile force against the cavity walls) of the coil member 3608, the apparatus 3600 may be utilized to treat a variety of sizes and shapes of lumpectomy cavities.

Turning to FIGS. 35A and 35B, another embodiment of an expandable brachytherapy treatment apparatus 3200 is shown. Similar to the previous embodiments, the apparatus 3200 generally includes a proximal hub 3207, a distal hub 3209, and a plurality of elongate members 3206 extending between the hubs 3207, 3209, thereby defining a longitudinal axis 3201. Also similar to previous embodiments, the hubs 3207, 3209 may be movable axially relative to one another to direct the elongate members 3206 between a first collapsed, e.g., straight, configuration (not shown), to a second deployed e.g., curvilinear, configuration (shown in FIGS. 35A and 35B).

Optionally, the apparatus 3200 may include an actuator (not shown), similar to those described elsewhere herein, which may be coupled to the proximal hub 3207. The actuator may be removably connectable to the proximal hub 3207 or permanently attached to the apparatus 3200 (not shown).

As best seen in FIG. 35B, the elongate members 3206 may be configured in two distinct groups, arrays, or layers. The first or outer group includes a plurality of elongate members 3206a (e.g., six shown), formed from tubular extrusions or bodies, which may include one or more lumens (not shown), stiffening members (also not shown), and the like, similar to other embodiments described herein. The second or inner group includes elongate members 3206b, which may also be formed from tubular bodies 3216b, including one or more lumens (not shown), stiffening members (also not shown), and the like. The inner elongate members 3206b may be shaped and/or otherwise configured similar to or different from the outer elongate members 3206a.

The elongate members 3206 may be formed from individual tubular bodies. For example, a tubular extrusion having a desired cross-section may be formed, which may then be cut into individual lengths corresponding to each of the elongate members 3206. Alternatively, as described elsewhere herein, a plurality of the elongate members 3206 may be formed as a single extrusion or other unitary tubular structure, which may be cut to separate the tubular structure into individual elongate members 3206b.

First or proximal ends of the elongate members 3206 may be attached to the proximal hub 3207 and second or distal ends of the elongate members 3206 may be attached to the distal hub 3209. For example, the proximal ends of the elongate members 3206 may extend at least partially through corresponding lumens in the proximal hub 3207 and be bonded, fused, or otherwise fixed to the proximal hub 3207. Alternatively, the proximal ends of the elongate members 3206 may be attached to nipples or other features on the proximal hub 3207. Similarly, the distal ends of the elongate members 3206 may be received in corresponding pockets in the distal hub 3209 and/or may be bonded, fused, or otherwise fixed to the distal hub 3209.

In any of the embodiments described herein, it may be advantageous to have the distal hub 3209 be removable or otherwise temporarily attached to the distal ends of the elongate members 3206 (not shown). This may expedite or otherwise facilitate removal of the apparatus 3200. For example, the distal ends of the elongate members 3206 may be released from the distal hub 3209 just prior to removal of the apparatus 3200.

Unlike previous embodiments, the inner elongate members 3206b include lateral extensions 3217 extending from the tubular bodies 3216b that increase a surface area of the inner elongate members 3206b. As shown, an extension 3217 is provided on opposite sides of each tubular body 3216b, e.g., extending laterally and/or circumferentially relative to the longitudinal axis 3201, thereby increasing a surface area of the inner elongate members 3206b that may contact tissue surrounding a cavity within which the apparatus 3200 is introduced. The resulting increased surface area may facilitate shaping tissue surrounding the cavity when the apparatus 3200 is expanded, e.g., by providing atraumatic contact surfaces that may push the surrounding tissue radially outwardly.

FIGS. 43A-44B include various cross-sections, into which the inner elongate members 3206b (or any of the elongate members in other embodiments described herein) may be formed. These cross-sectional views show multiple elongate members in various arrays in collapsed configurations. These cross-sectional configurations may provide a preferred bending bias in the radial direction, and/or may enhance lateral stability (e.g., resistance to lateral deflection during expansion). These configurations may provide a substantially symmetrical geometry of the elongate members in the expanded configuration, which may allow stiffening members, e.g., metal strips and the like, as described herein, to be eliminated. Eliminating stiffening members may also simplify compatibility with common LDR radiation sources, such as Palladium, Iodine and Cesium. Stiffening members, particularly, metal strips, may at least partially attenuate penetration of radiation into surrounding tissue, when LDR radiation sources are provided within the elongate members. However, such stiffening members may only minimally affect penetration of radiation from commonly used HDR radiation sources (e.g. Iridium).

Figure 43A:
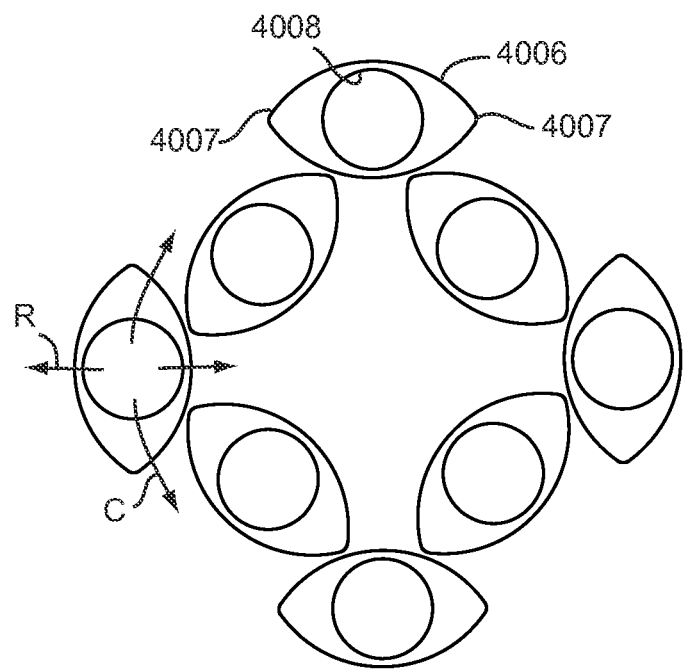
FIGS. 43A-43D are cross-sectional views of alternate embodiments of extrusions that may be used to form elongate members, similar to that shown in FIGS. 41A and 41B, that may have increased lateral stability, a radial bending bias, and/or an enlarged footprint.

Turning to FIG. 43A, an exemplary embodiment of an array of elongate members 4006 is shown, each elongate member 4006 having a substantially eyelet shape and including an internal lumen 4008. The eyelet shape provides an increased outer surface defined at least partially by side extensions 4007, which may provide a substantially atraumatic contact surface that may push the surrounding tissue radially outwardly. In addition, the eyelet shape may provide an elongate member having a greater moment of inertia in a circumferential direction (represented by arrows "C") than in a radial direction (represented by arrows "R"). Such an orientation may bias the elongate members to deflect radially outwardly during expansion and/or may enhance lateral stability of the elongate members, e.g., by resisting movement in the direction of greater moment (i.e., the circumferential direction). As shown, the elongate members 4006 are arranged in inner and outer groups, similar to other embodiments described herein. It will be appreciated that a single layer of elongate members 4006 may be provided and/or different numbers of elongate members may be provided than the eight elongate members 4006 shown in FIG. 43A.

Figure 43B:
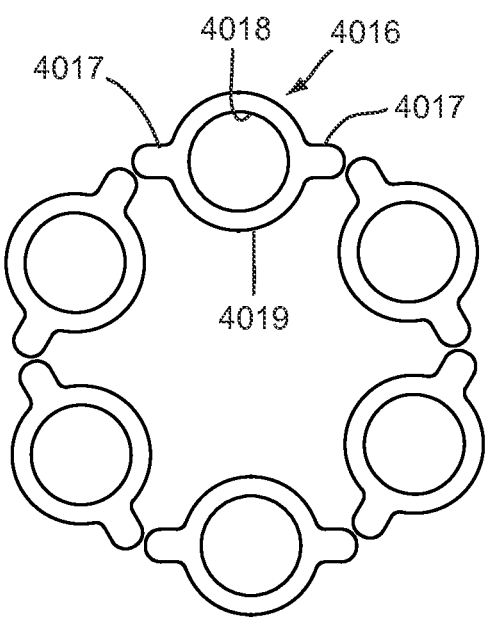

Turning to FIG. 43B, another array of elongate members 4016 is shown arranged symmetrically around a central axis in a single layer. In this embodiment, each elongate member 4016 includes a central tubular portion 4019 defining a lumen 4018, and a pair of opposing extensions 4017. The elongate members 4016 may be formed from individual tubular bodies or from a single tubular body that is separated between adjacent extensions 4017, similar to methods described elsewhere herein.

Figure 43C:
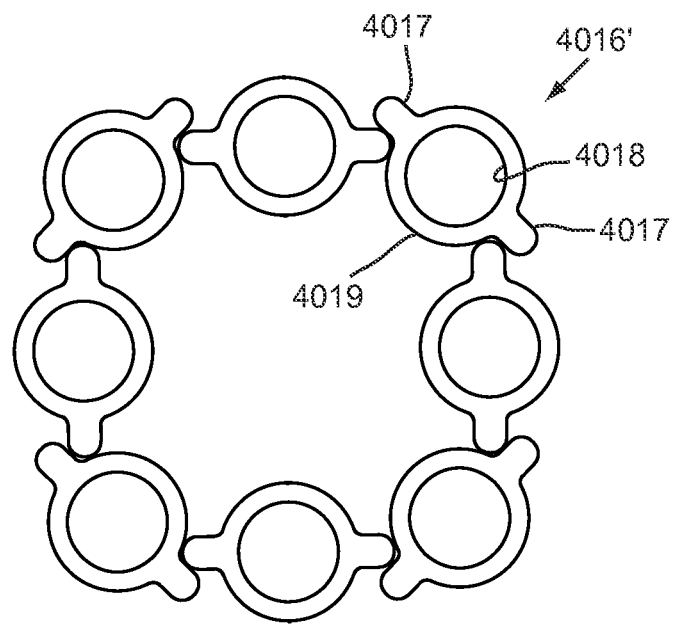

FIG. 43C shows an alternative array of elongate members 4016' generally formed similar to those shown in FIG. 43B. Unlike the array in FIG. 43B, which are generally disposed in a side-by-side circular arrangement, the elongate members 4016' in FIG. 43C are arranged in a generally square arrangement, e.g., by partially nesting adjacent extensions 4017.

Figure 43D:
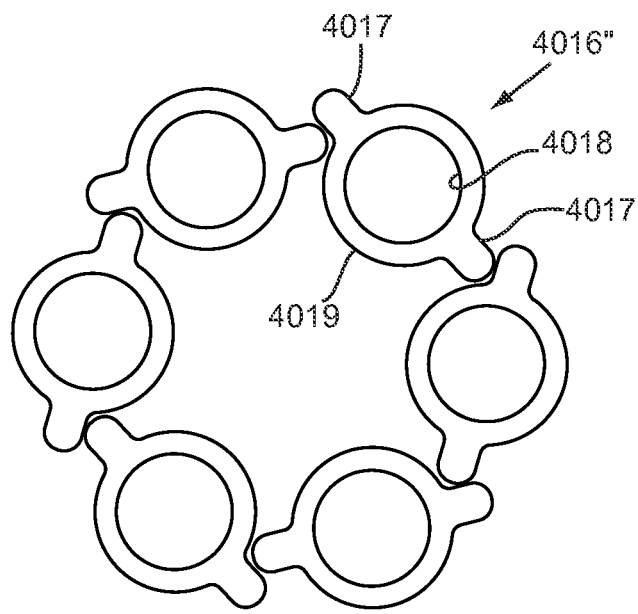

FIG. 43D shows another array of elongate members 4016" generally similar to those shown in FIGS. 43B and 43C. Unlike the previous embodiments, the array includes six elongate members 4016" arranged in a substantially circular arrangement, also involving partially nesting adjacent extensions 4017. Each of these arrangements may provide elongate members that have greater moment of inertia in the circumferential direction than in the radial direction, also providing greater contact surface area, radial bias, and/or lateral stability.

It will be appreciated that the number of elongate members in any of the embodiments described herein may be increased and/or the width of the individual elongate members (or extensions) may be increased, e.g., to reduce tissue invagination and/or increase cavity reshaping and/or enlargement. Conversely, the number of elongate members and/or width of the individual elongate members may be decreased, if it is desired to increase tissue invagination and/or reduce the extent of cavity reshaping and/or enlargement.

Figure 44A:
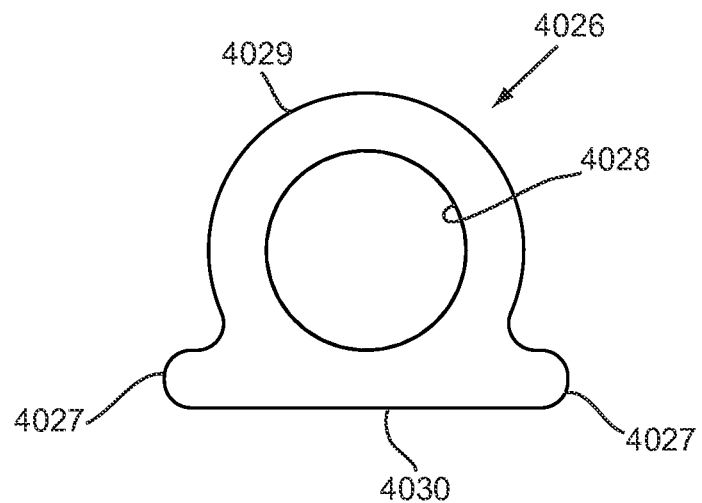
FIGS. 44A and 44B are cross-sectional views of additional alternative embodiments of an individual elongate member that may be included in the expandable brachytherapy apparatus described herein.

Turning to FIG. 44A, a cross-section of an alternative embodiment of an elongate member 4026 is shown that generally includes a tubular portion 4029 defining a lumen 4028 (providing a pathway for a radiation source, not shown, similar to the previous embodiments). In addition, the elongate member 4026 includes lateral extensions 4027, which, in this embodiment, define a substantially flat outer surface 4030. The flat outer surface 4030 may facilitate contact with surrounding tissue, e.g., to enhance shaping tissue surrounding a lumpectomy cavity, similar to embodiments described elsewhere herein.

Figure 44B:
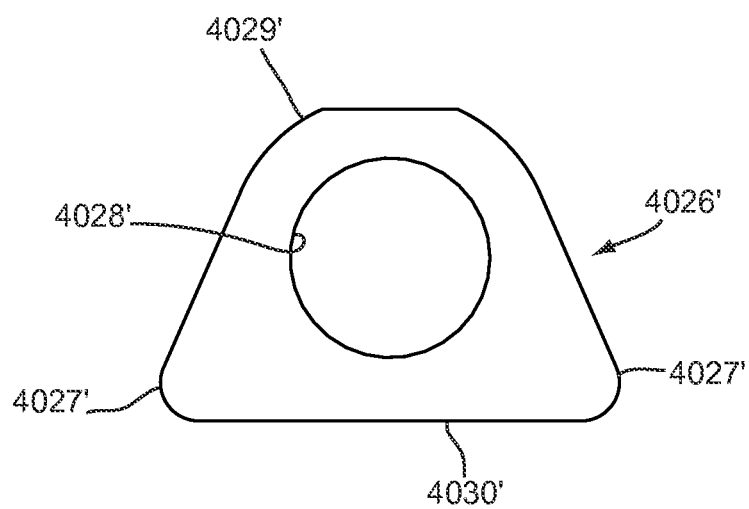

An alternative embodiment of an elongate member 4026' is shown in FIG. 44B, in which the tubular portion 4029' and lateral extensions 4027' are more closely integrated than in the embodiment shown in FIG. 44A. Similar to the previous embodiment, the elongate member 4026' includes a lumen 4028' for receiving a radiation source (not shown), and a substantially flat outer surface 4030' for contacting surrounding tissue. The elongate members 4026, 4026' shown in FIGS. 44A and 44B may be incorporated into any of the embodiments disclosed herein, e.g., such that the outer surface 4030, 4030' is oriented radially outwardly.

Returning to the embodiment shown in FIGS. 35A and 35B, the outer elongate members 3206a do not include extensions and/or increased surface areas, unlike the inner elongate members 3206b. This may enhance tissue invagination and/or penetration of the outer elongate members 3206a into tissue surrounding a cavity within which the apparatus 3200 is expanded. Alternatively, the outer elongate members 3206a may include extensions and/or increased surface area if it is desired for the outer elongate members to push the surrounding tissue and/or otherwise shape the cavity upon expansion, thereby reducing the degree of tissue invagination between the elongate members. Optionally, in such an alternative, the inner elongate members may be eliminated (e.g., as shown in FIGS. 38A and 38B) or may be provided with or without the extensions 3217.

With continued reference to FIG. 35A, the apparatus 3200 may include a core member 3210 that is attached to the distal hub 3209 and extends into and/or through the proximal hub 3207. Consequently, the proximal hub 3207 may slide axially along the core member 3210, similar to the previous embodiments. An actuator (not shown) may be coupled to the proximal hub 3207 and/or core member 3210 to control relative axial movement, as described elsewhere herein.

As described elsewhere herein, each of the elongate members 3206 may include one or more stiffening members (not shown), which may bias the elongate members 3206 to expand and contract in the desired orientation, e.g., without twisting or deviating from radial movement substantially orthogonal to the longitudinal axis 3201. The stiffening member(s) may also provide some integrity to the tubular bodies of the elongate members 3206, which may be otherwise substantially flexible and/or prone to kinking. Alternatively, the stiffening members may be unnecessary, e.g., because of the bias and/or lateral stability provided by the cross-sectional shape of the elongate members. This alternative may provide some advantages for LDR applications, since stiffening members may attenuate or otherwise affect radiation delivery, e.g., due to metallic materials in the stiffening members, as described elsewhere herein.

During use, the apparatus 3200 may be provided with the elongate members 3206 in the collapsed configuration (not shown). The distal hub 3209 may be inserted into a tract through tissue (either alone, e.g., using a sharpened or pointed distal tip, or via a cannula or other tubular member, not shown) until the elongate members 3206 are disposed within a target tissue region, e.g., within a lumpectomy cavity. In an alternative embodiment, as shown in FIG. 54, a delivery apparatus 4050 may be used to access and/or deliver the apparatus 3200. Generally, the delivery apparatus 4050 may include a trocar 4052 and a sheath 4062. The trocar 4052 may be a substantially rigid or semi-rigid elongate body including a proximal end 4054 and a sharpened distal tip 4056. The sheath 4062 may include a proximal end 4064, a distal end 4066, and one or more handles 4068 fixed to or otherwise on the proximal end 4064. In addition, the sheath 4062 may include one or more weakened regions or other seams 4070 extending between the proximal and distal ends 4064, 4066. The sheath 4062 may be sized for receiving a brachytherapy treatment apparatus, such as apparatus 3200 therethrough with the elongate members 3206 in the collapsed configuration.

As shown in FIG. 54, the delivery apparatus 4050 may be provided initially with the sheath 4062 surrounding the trocar 4052 such that the sharpened distal tip 4056 extends beyond the distal end 4066 of the sheath 4062. The delivery apparatus 4050 may be inserted through tissue, e.g., by penetrating the sharpened distal tip 4056 directly through the patient's skin (e.g. via a skin nick), through the intervening breast tissue, and into the treatment site, e.g., a lumpectomy cavity (all not shown). Once the distal end 4066 of the sheath 4062 is disposed within the treatment site, the trocar 4052 may be removed proximally from the sheath 4062. Optionally, the proximal end 4054 of the trocar 4052 and the handle(s) 4068 on the sheath 4062 may include features (e.g., detents) that interlock or otherwise secure the trocar 4052 within the sheath 4062. When the trocar 4052 is removed, such features may be disengaged, e.g., by unlocking the features or simply pulling with sufficient force to release the features.

With additional reference to FIG. 35A, the brachytherapy treatment apparatus 3200 may be advanced through the sheath 4062 in the collapsed configuration until the elongate members 3206 are disposed within the treatment site. With the elongate members 3206 disposed within the treatment site, e.g., adjacent to the distal end 4066 of the sheath 4062, the sheath 4062 may be removed to expose the elongate members 3206 within the treatment site. To do so, the sheath 4062 may be separated, e.g., by pulling the handles 4068 proximally and away from one another, thereby causing the sheath 4062 to split along the seam(s) 4070. Thus, the sheath 4062 may simply tear-away to accommodate removing the sheath 4062, e.g., over an enlarged proximal hub 3207 on the apparatus 3200. Such a delivery apparatus 4050 and method for placing the apparatus 3200 may also be used to deliver any of the other embodiments described elsewhere herein.

As an alternative delivery method and apparatus, a needle may be placed into the treatment location, e.g., a lumpectomy cavity, by conventional imaging techniques (e.g., ultrasound). Once the needle tip is in the desired location, e.g., the lumpectomy cavity), a guidewire may be passed through the needle. The needle may then be removed, leaving the tip of the guidewire in the desired location. Then, a tapered tip dilator/sheath assembly may be advanced over the guidewire so that the distal tip of the outer sheath is within the treatment location. The guidewire and dilator may then be removed, leaving the sheath in position extending to the treatment location. The apparatus 3200 may then be placed through the sheath and, once apparatus 3200 is in the desired position within the tissue, the sheath may be removed, e.g., peeled away similar to the method described previously.

Returning to FIGS. 35A and 35B, the proximal hub 3207 may be directed distally relative to the core member 3210, thereby causing the elongate members 3206 to bow outwardly, as shown. When the apparatus 3200 is directed to the expanded configuration, the extensions 3217 of the inner elongate members 3206b may at least partially direct tissue that invaginates between the outer elongate members 3206a to shape the cavity in a desired manner. In other words, an elongate member with a wider footprint (that presses into tissue surrounding a lumpectomy cavity) may tend to reshape and/or enlarge the lumpectomy cavity and have less invagination than a narrower footprint. Conversely, a relatively narrower footprint on the elongate members may be more likely to penetrate deeper into the tissue, which may enhance invagination and/or create less cavity reshaping and/or enlargement.

Thereafter, the apparatus 3200 may be secured, e.g., to prevent the elongate members 3206 from moving back towards the collapsed configuration. For example, a clamp or similar device (not shown) may be crimped around the core member 3210 immediately adjacent the proximal hub 3207 to prevent the core member 3210 and/or proximal hub 3207 from sliding relative to one another. Alternatively, if the actuator is removable, the proximal hub 3207 may be configured to remain substantially stationary unless manipulated by the actuator, e.g., due to friction between mating threads on the proximal hub 3207 and the core member 3210. Thus, upon removing the actuator, the proximal hub 3207 may remain substantially stationary when the actuator is disconnected and removed. Other methods for securing the apparatus 3200 in the desired diameter or other expanded configuration may also be provided, as described elsewhere herein.

One or more radiation sources may then be directed into the elongate members 3206 to deliver radiation to the tissue surrounding the cavity. Thus, the elongate members 3206 may define pathways for receiving radiation source(s). For example, a plurality of LDR sources may be delivered into the elongate members 3206 and remain indwelling for a predetermined time. Alternatively, one or more HDR sources may be delivered sequentially into the elongate members 3206 according to a desired dose plan, as described elsewhere herein. For example, an HDR source may be introduced into a first elongate member 3206, advanced to a first position, and maintained at the first position for a predetermined time. The HDR source may then be advanced and/or retracted to a second position, and maintained there for a predetermined time, etc. The HDR source may then be removed from the first elongate member 3206, and then introduced sequentially into each of the other elongate members 3206 in a similar manner. In a further alternative, one or more radiation sources may be preloaded or secured within the elongate members 3206 before introduction into the cavity.

Turning to FIGS. 36A and 36B, another embodiment of an expandable brachytherapy treatment apparatus 3300 is shown, which generally includes a proximal hub 3307, a distal hub 3309, and a plurality of elongate members 3306 extending between the hubs 3307, 3309. The apparatus 3300 may also include a core member (not shown) or other actuator for directing the elongate members 3306 between a collapsed configuration (not shown) and an expanded configuration, as shown. The construction of these components may be similar to other embodiments described herein.

Unlike previous embodiments, the apparatus 3300 includes one or more flexible membranes 3317 extending between adjacent elongate members 3306. For example, an elastomeric or other thin and/or flexible material, e.g., silicone, polyurethane and the like, may be attached to or otherwise suspended from edges of adjacent elongate members 3306, thereby providing an individual web or surface extending between the adjacent elongate members 3306. Alternatively, a single sleeve, sheet, or other membrane 3317 may be attached around all of the elongate members 3306. In this alternative, the membrane 3317 may be substantially deformable to accommodate expansion of the elongate members 3306, while causing the membrane to stretch inwardly between adjacent elongate members 3306. In a further alternative, the membrane(s) 3317 may be a substantially non-elastomeric or partially elastomeric material that may unfold in addition to or instead of stretching when the elongate members 3306 are directed from the collapsed configuration towards the expanded configuration. In yet a further alternative, the membrane(s) 3317 may have a non-uniform thickness (e.g., thicker at the central region between the adjacent elongate members 3306 and thinner in the immediate vicinity of the elongate members 3306) to help create a concave profile of membrane 3317, e.g., as shown in FIG. 36B.

The membrane(s) 3317 may define a substantially flat or concave web, a braided array of polymer filaments, or other surface extending between adjacent elongate members 3306. During use, when the apparatus 3300 is expanded within a cavity, the elongate members 3306 may press outwardly against surrounding tissue. As this occurs, the surrounding tissue may invaginate at least partially between the elongate members 3306, as described elsewhere herein. However, as the tissue invaginates, the membrane(s) 3317 may press or otherwise contact the invaginating tissue, which may limit or otherwise control the degree of invagination. Thus, once the apparatus 3300 is fully expanded, the profile of the surrounding tissue may be predicted more easily, which may facilitate selecting and/or using an appropriate dose plan for radiation delivered using the apparatus 3300. Thereafter, one or more radiation sources may be introduced into the apparatus 3300 similar to other embodiments described elsewhere herein.

Optionally, in some embodiments, the membrane(s) 3317 may completely surround the expanded elongate members 3306 and form a seal around the interior of the expanded apparatus 3300. In other embodiments, however, it may be desirable for the membrane to have openings, voids or other gaps therethrough (not shown). These gaps may allow fluids to pass between the internal and external surfaces of the membrane. In this way, any buildup of fluid (e.g., seroma) against the exterior or interior surface of the membrane may be minimized, thereby minimizing movement of target tissue relative to the expanded elongate members 3306, to optimize consistent dosing.

Turning to FIGS. 37A and 37B, yet another embodiment of an expandable brachytherapy treatment apparatus 3400 is shown, which generally includes a proximal hub 3407, a distal hub 3409, and a plurality of elongate members 3406 extending between the hubs 3407, 3409. The apparatus 3400 may also include a core member (not shown) or other actuator for directing the elongate members 3406 between a collapsed configuration (not shown) and an expanded configuration, as shown. The construction of these components may be similar to other embodiments described herein.

In addition, the apparatus 3400 includes a sleeve 3417 supported within an interior space defined by an array of outer elongate members 3406a. For example, in the embodiment shown, the sleeve 3417 is at least partially supported by a plurality of inner elongate members 3406b, which may be constructed similar to previous embodiments. The inner elongate members 3406b may include tubular bodies for receiving one or more sources of radiation (not shown). Alternatively, the inner elongate members 3406b may simply be ribs, stiffening members, or other structures within, attached to, or otherwise contacting the sleeve 3417. Thus, the sleeve 3417 may define an inner volume spaced apart from the outer elongate members 3406a.

The sleeve 3417 may include one or more membranes, which may be constructed and/or attached to the inner elongate members 3406b similar to the membrane(s) 3317 shown in FIGS. 36A and 36B. For example, the sleeve 3417 may be formed from an elastomeric or similar material that may surround the inner elongate members 3406b such that sleeve 3417 may stretch or otherwise expand elastically as the inner elongate members 3406b are directed from the collapsed configuration to the expanded configuration. Alternatively, the sleeve 3417 may be formed from a substantially inelastic and/or noncompliant material, and the sleeve 3417 may at least partially unfold when the inner elongate members 3406b are directed towards the expanded configuration.

When the apparatus 3400 is expanded, the sleeve 3417 may expand to a substantially bulbous shape, e.g., a substantially spherical, football, watermelon, or other shape. The sleeve 3417 may contact surrounding tissue, e.g., that invaginates or otherwise extends between the outer elongate members 3406a, thereby limiting and/or controlling the positioning of the surrounding tissue. Similar to the previous embodiment, the sleeve 3417 may direct the surrounding tissue in a desired and/or more predictable manner, such that the profile and/or configuration of the surrounding tissue may be predicted more easily, which may facilitate selecting an appropriate dose plan for radiation delivered using the apparatus 3400.

Turning to FIGS. 38A and 38B, still another embodiment of an expandable brachytherapy treatment apparatus 3500 is shown, which generally includes a proximal hub 3507, a distal hub 3509, and a plurality of elongate members 3506 extending between the hubs 3507, 3509. The apparatus 3500 may also include a core member 3510 or other actuator for directing the elongate members 3506 between a collapsed configuration (not shown) and an expanded configuration, as shown. The construction of these components may be similar to other embodiments described herein.

Unlike previous embodiments, the elongate members 3506 include lateral extensions 3517 extending from the tubular bodies 3516 that increase a surface area of the elongate members 3506. As shown, an extension 3517 is provided on opposite sides of each tubular body 3516, e.g., extending laterally and/or circumferentially relative to the longitudinal axis 3501, thereby increasing a surface area of the inner elongate members 3506 that may contact tissue surrounding a cavity within which the apparatus 3500 is introduced. The resulting increased surface area may facilitate shaping tissue surrounding the cavity when the apparatus 3500 is expanded, e.g., by providing atraumatic contact surfaces that may push the surrounding tissue radially outwardly.

Figure 39A:
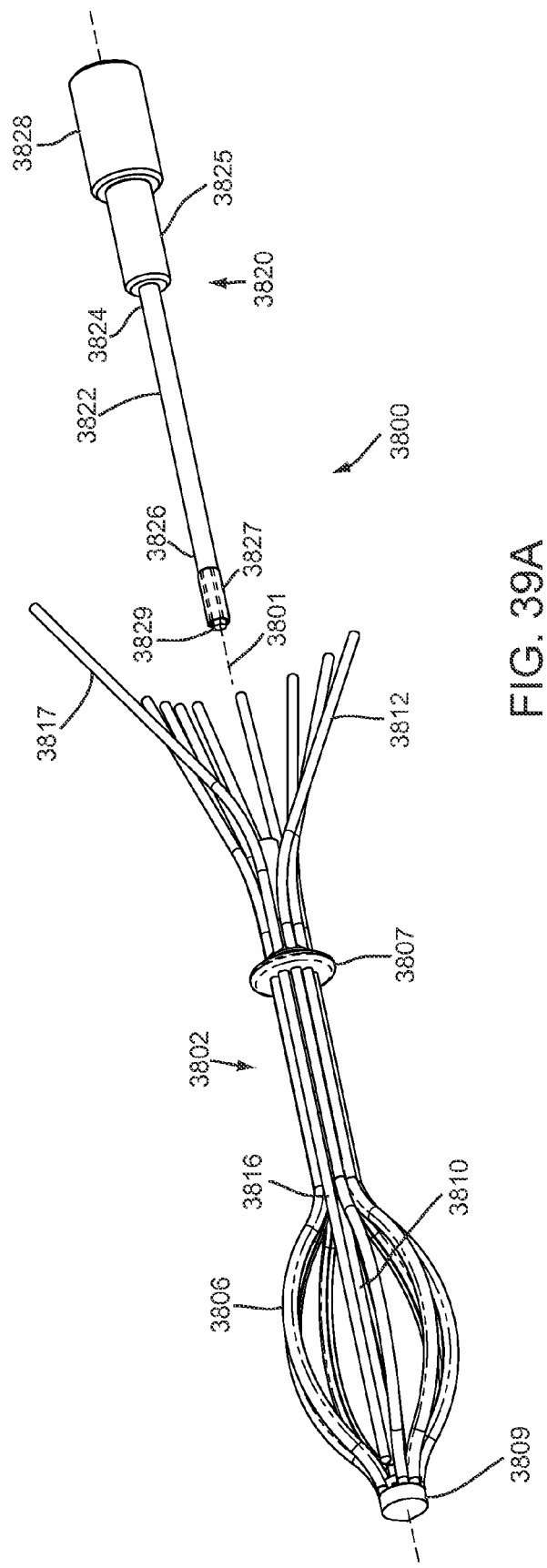
FIGS. 39A and 39B are perspective and side views, respectively, of an eleventh exemplary embodiment of an expandable brachytherapy apparatus, including a removable expansion tool and a central lumen for receiving a radiation source.
Figure 39B:
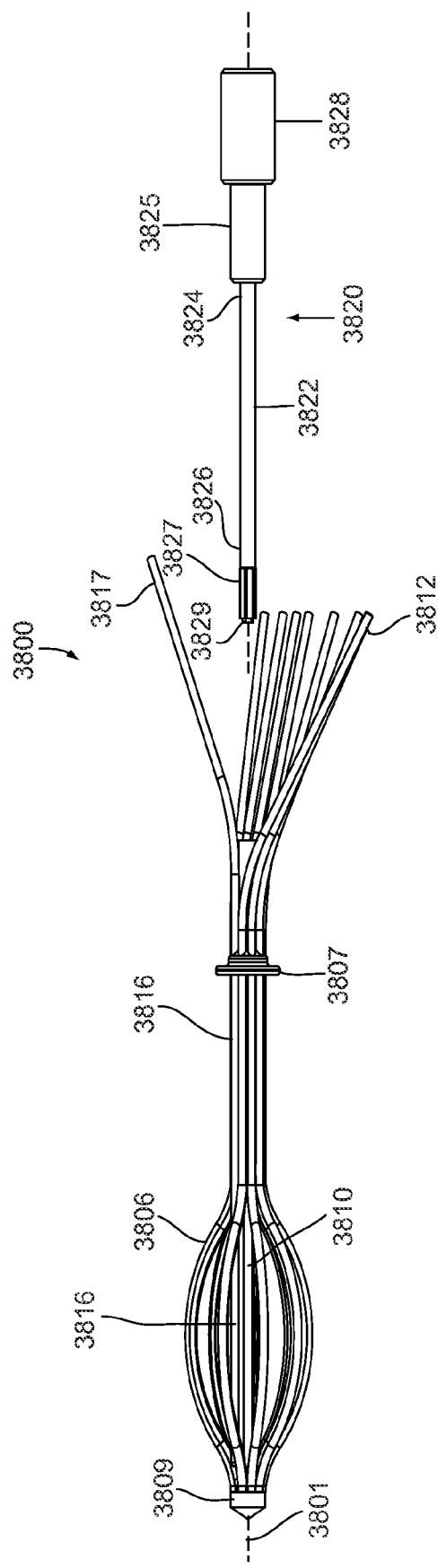

Turning to FIGS. 39A and 39B, another embodiment of an expandable brachytherapy treatment apparatus 3800 is shown that includes an expandable device 3802 and an actuator tool 3820. Generally, the expandable device 3802 includes a proximal hub (not shown), sliding button 3807, a distal hub 3809, and a plurality of elongate members 3806 extending between the proximal and distal hubs. The apparatus 3800 may also include a core member 3810 extending between the proximal and distal hubs 3807, 3809 for directing the elongate members 3806 between a collapsed configuration (not shown) and an expanded configuration, as shown. The construction of these components may be similar to other embodiments described herein.

Unlike previous embodiments, the elongate members 3806 extend from the distal hub 3809, through the proximal hub and sliding button 3807 to proximal ends 3812. The elongate members 3806 may be formed from single extrusions or other tubular bodies, or may be formed from multiple tubular bodies connected to one another, e.g., by bonding, fusing, lapping, and the like. As shown, the proximal ends 3812 extend radially away from the central longitudinal axis 3801. The proximal ends 3812 may be substantially rigid in the radial direction to securely attach to an after-loader transfer tube (not shown), yet flexible along their lengths for patient comfort and/or maneuverability. This configuration may facilitate identifying particular elongate members 3806, e.g., for receiving one or more radiation sources, as described elsewhere herein.

In addition, the expandable device 3802 also includes a central tubular member 3816, which may extend substantially parallel to the longitudinal axis 3801, e.g., adjacent the core member 3810, and may include a central lumen or other pathway (not shown). The central tubular member 3816 may include a proximal end 3817, which may also extend away from the longitudinal axis 3801, e.g., diagonally, as shown. Optionally, the proximal end 3817 of the central tubular member 3816 may be offset from the proximal ends 3812 of the other elongate members 3806 or otherwise distinguished, e.g., to facilitate identification of the central tubular member 3816. For example, the proximal ends 3812 of the elongate members 3806 may be disposed around one portion of the circumference of the expandable device 3802, while the proximal end 3817 of the central tubular member 3816 may be disposed on the opposite portion of the circumference.

Similar to previous embodiments, the button 3807 may be movable axially relative to the elongate members 3806 anywhere from the skin surface to the proximal ends 3812, e.g., to help organize the array of elongate members 3806, as desired. The apparatus 3800 includes a removable expansion tool 3820, which may be coupled to the expandable device 3802 for directing the elongate members 3806 between the collapsed and expanded configurations.

The expansion tool 3820 generally includes inner and outer elongate shafts, e.g., an outer tubular shaft 3822 and an inner rod, cable, wire, or other shaft (not shown), that are rotatable relative to one another. The outer shaft 3822 includes a proximal end 3824 with a handle 3825 and a distal end 3826 including one or more features 3827, e.g., an outer hexagonal shape that may engage with corresponding features on the proximal hub, e.g., an inner hexagonal shape (not shown). The inner shaft includes a proximal handle 3828 adjacent the handle 3825 and one or more features, e.g., a hexagonal keyed tip 3829 adjacent or beyond the keyed distal end 3827 of the outer shaft 3822. The tip 3829 may be received in a corresponding keyed region, e.g., a hexagonal region or other feature (not shown) or otherwise engage with a proximal end of the core member 3810.

During use, the expansion tool 3820 may be inserted between the elongate members 3806 and engaged with the proximal hub and core member 3810. For example, the expansion tool 3820 may be rotated until the hex-keyed end 3827 on the outer shaft 3822 engages the hexagonal region in the proximal hub and the keyed tip 3829 is received in the corresponding pocket in the core member 3810. Thereafter, when the handles 3825, 3828 are rotated in opposite directions relative to one another, the proximal hub may be advanced distally and/or proximally relative to the core member 3810 to expand and/or collapse the elongate members 3806, similar to other embodiments described elsewhere herein.

If desired, a flexible tubing member (not shown) may be attached to the proximal hub 3807 with the longitudinal axis of the tubing member in line with the center of the keyed element of the proximal hub 3807. In this way, the expansion tool may be passed within or around the tubing member to insure that the two mating surfaces will easily and properly engage one another. This tubing member may be a tubing element defining a radiation pathway, or it may be a relatively large diameter tube that receives the shaft 3826 of the expansion tool.

Figure 47A:
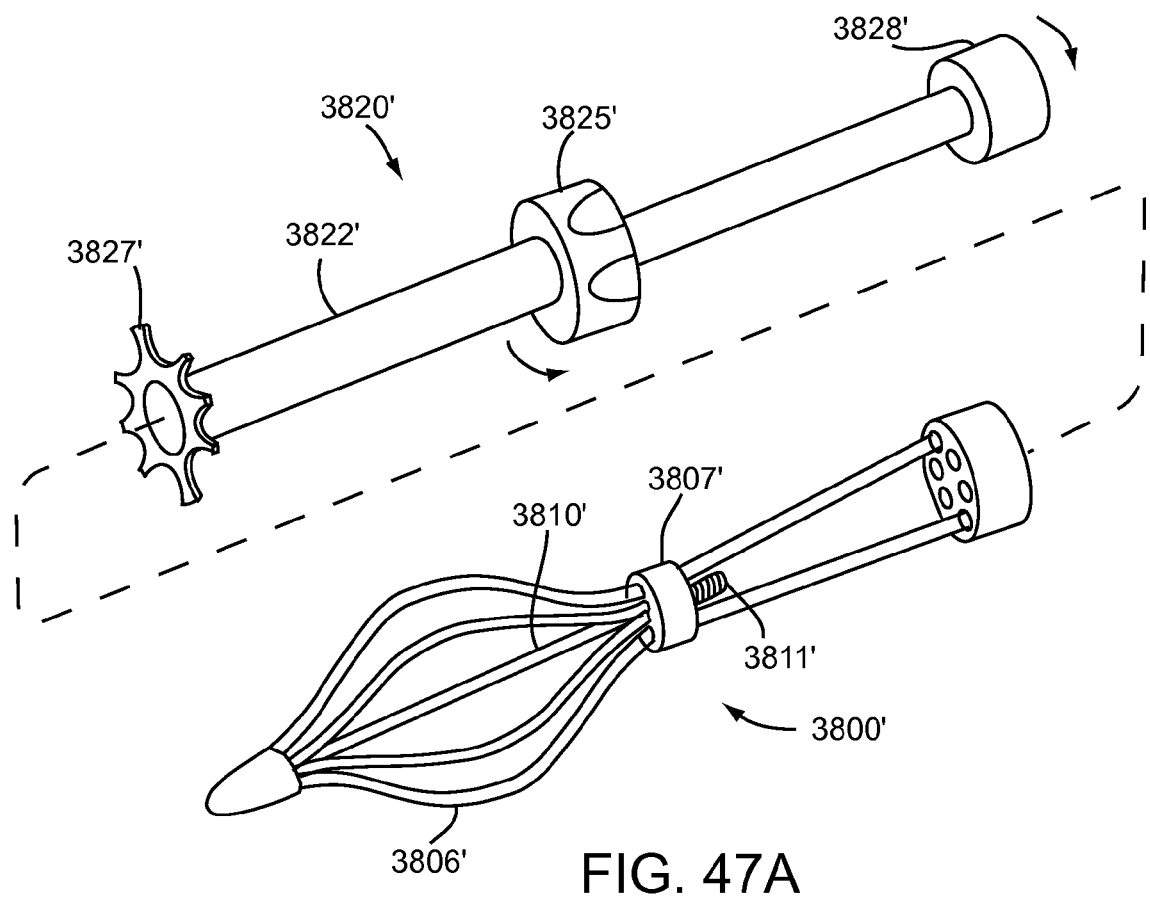
FIG. 47A is a perspective view of an expandable brachytherapy apparatus and a tool for actuating the apparatus between collapsed and expanded configurations.

Turning to FIG. 47A, an alternative embodiment of an expansion tool 3820' is shown that may be used to expand and collapse a brachytherapy treatment apparatus 3800,' which may be similar to any of the embodiments described herein. Similar to the previous embodiment, the expansion tool 3820' includes an outer tubular shaft 3822' and an inner rod, cable, wire, or other shaft 3830', that are rotatable relative to one another. The outer shaft 3822' includes a proximal end 3824' with a handle 3825' and a distal end 3826' including one or more features 3827,' e.g., spokes, that may be received between adjacent elongate members 3806' on the apparatus 3800' and/or within the proximal hub 3807,' thereby rotationally coupling the outer shaft 3822' to the apparatus 3800.' The inner shaft 3830' includes a proximal handle 3828' and one or more features, e.g., a keyed tip 3829' adjacent or within the distal end 3826' of the outer shaft 3822,' which may engage with a proximal end 3811' of the core member 3810.'

Thus, when the expansion tool 3820' is coupled to the apparatus 3800,' the handles 3825,' 3828' may be rotated in opposite directions to expand or collapse the elongate members 3806.' For example, the expansion tool 3820' may be coupled to the apparatus 3800' before or after introducing the apparatus 3800' into a patient's body, i.e., with the elongate members 3806' in the collapsed configuration (not shown). The handles 3825,' 3828' may be rotated in first opposing directions, thereby expanding the elongate members 3806' to the expanded configuration, as shown in FIG. 47A.

The expansion tool 3820' may then be disengaged and removed. When it is desired to remove the apparatus 3800' (or adjust the expanded configuration of the elongate members 3806'), the expansion tool 3820' may be recoupled to the apparatus 3800.' To remove the apparatus 3800,' the handles 3825,' 3828' may be rotated in second opposing directions, thereby collapsing the elongate members 3806,' whereupon the apparatus 3800' may be removed from the patient's body. The expansion tool 3820' may minimize or substantially eliminate unwanted torque being applied to the apparatus 3800' and/or surrounding tissue when the expansion tool 3820' is used to expand or collapse the elongate members 3806.'

Returning to FIGS. 39A and 39B, the apparatus 3800 may be used to deliver radiation to a patient, similar to other embodiments described herein. In addition, the central lumen 3816 may be used as an additional pathway for delivering radiation, e.g., during HDR radiation treatment. Thus, subsequent to or concurrent with introducing one or more radiation sources into the elongate members 3806, a radiation source may be introduced into the central lumen 3816.

For example, the central lumen 3816 may be used in a manner to minimize overexposure or "burning" of surrounding tissue adjacent the proximal and/or distal ends of the elongate members 3806 (also referred to as "at the poles" where the largest diameter of the elongate members 3806 in the expanded configuration defines the "equator"). If full dose radiation source(s) were delivered into the elongate members 3806 immediately adjacent the proximal or distal ends thereof, the resulting radiation intensity may be higher than desired. One option is to use spacers or lower activity sources at the ends of the elongate members 3806, e.g., for LDR applications, or to reduce the dwell time at the poles for HDR applications. However, this approach may in some instances lead to inadequate penetration of the radiation dose at the polar regions of the device. Therefore, using the central lumen 3816 may allow radiation delivery to enhance the desirable dose distribution in these polar regions. In general, using the central lumen 3816 may allow radiation to be delivered with more precision and flexibility, when used in combination with the outer layers of the elongate members 3806. In some instances, for example when treating symmetrical cavity regions in proximity to adjacent radiation-sensitive structures (e.g., skin, chest wall, and the like), the central lumen 3816 may be the only lumen used for radiation delivery.

It will be appreciated that a central tubular member and/or lumen may be included in any of the embodiments described herein. Turning to FIGS. 52A and 52B, an alternative embodiment of an expandable brachytherapy apparatus 3800' is shown that includes a plurality of elongate members 3806,' a core member 3810,' and a central tubular member 3816' extending between proximal and distal hubs 3807,' 3809.' The components of the apparatus 3800' may be generally similar to the apparatus 3800 shown in FIGS. 39A and 39B. Unlike the apparatus 3800, the apparatus 3800' includes a distal hub 3809' that includes a hub cap or bump tip 3819,' which may be integrally formed with or attached to the distal hub 3809.' The bump tip 3819' provides an interior cavity for receiving a distal end 3816a' of the central tubular member 3816,' such that the central tubular member 3816' extends distally beyond the elongate members 3806.'

The extension of the central tubular member 3816' may accommodate receiving a radiation source that extends distally beyond the elongate members 3806,' which are attached to the distal hub 3809' radially outwardly from a central axis of the apparatus 3800.' Thus, a radiation source (not shown) may be advanced into the central tubular member 3816' into the bump tip 3816a,' which may enhance radiation delivery to tissue distally beyond, surrounding, or otherwise adjacent the distal hub 3809' and bump tip 3819.'

Figure 40A:
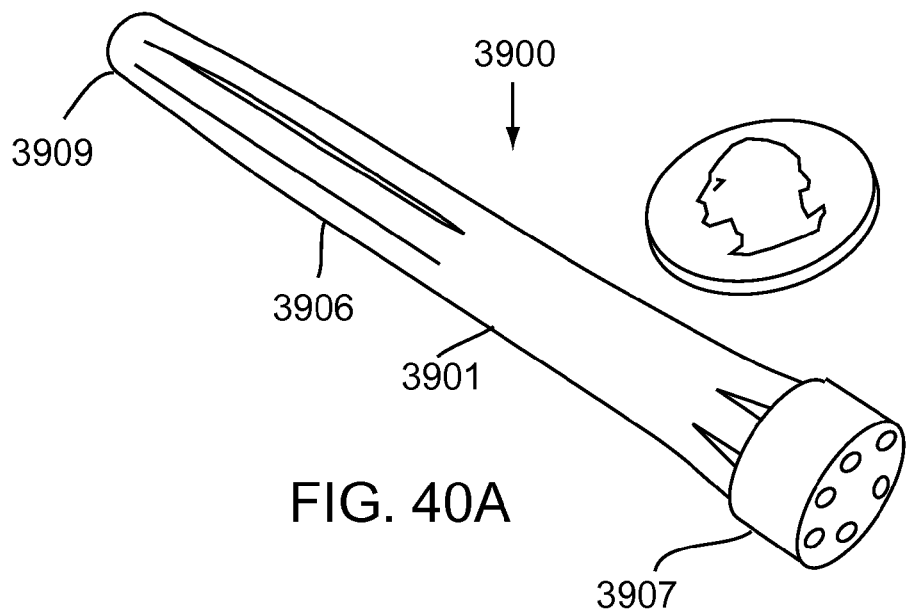
FIGS. 40A and 40B are perspective views of a twelfth exemplary embodiment of an expandable brachytherapy apparatus, including a unitary body of elongate members in collapsed and expanded configurations, respectively.
Figure 40B:
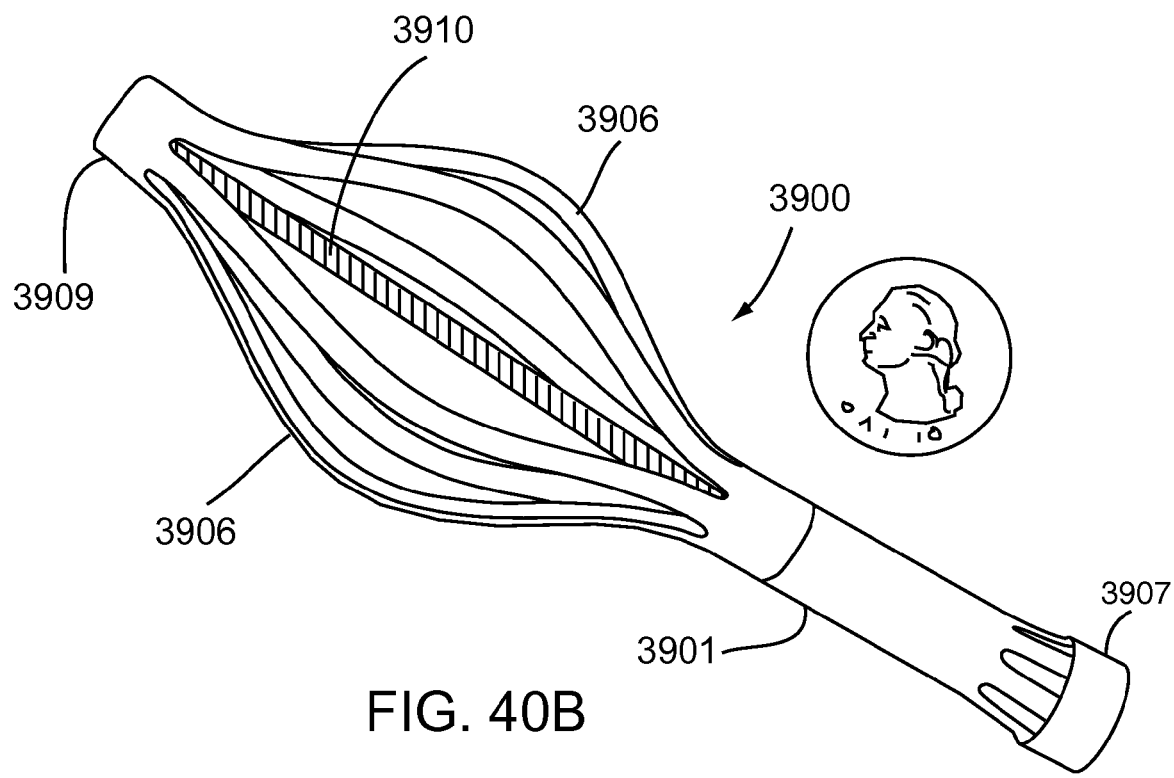

Turning to FIGS. 40A and 40B, another embodiment of an expandable brachytherapy treatment apparatus 3900 is shown that includes a plurality of elongate members 3906 extending between proximal and distal hubs 3907, 3909, which are formed as a unitary body 3901. FIG. 40A shows the elongate members 3806 in a collapsed configuration, while FIG. 40B shows the elongate members 3806 in an expanded configuration, allowing a core member 3910 to be seen. The core member 3910 may be a separate elongate member, e.g., threaded at least partially along its length so that the core member 3910 may be rotated within the unitary body to allow the elongate members 3906 to be expanded and collapsed, similar to the other embodiments described herein.

Figure 41A:
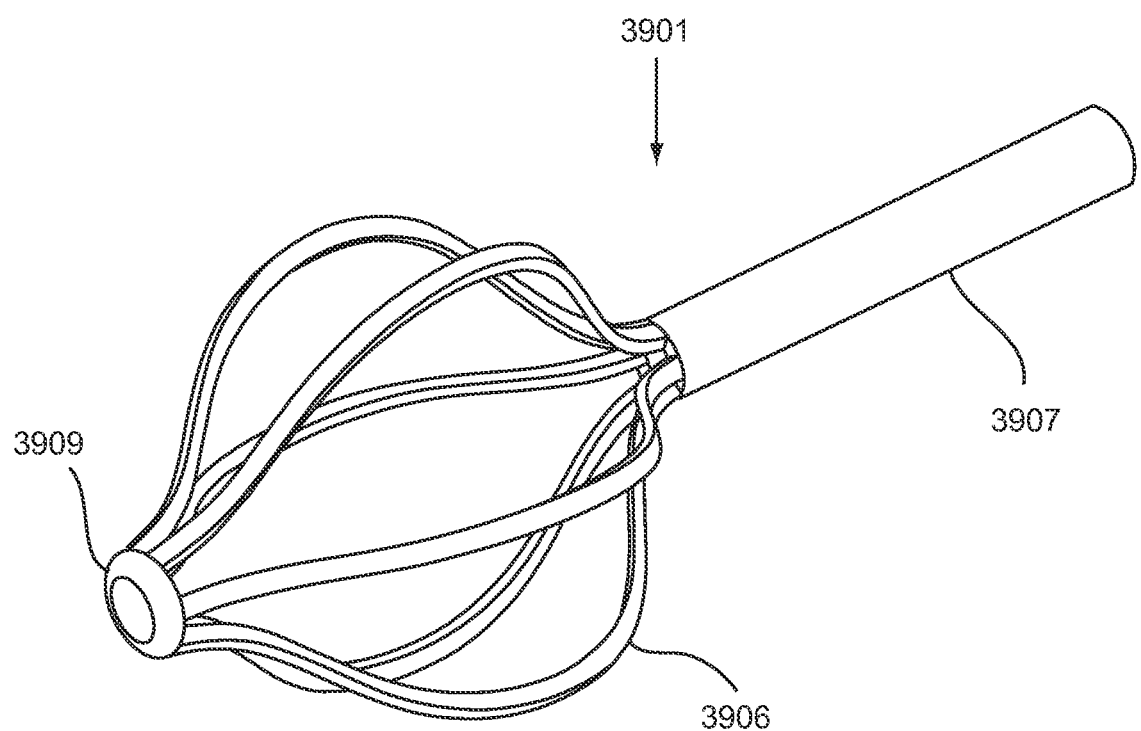
FIGS. 41A and 41B are perspective views of the unitary body of FIGS. 40A and 40B from distal and proximal ends, respectively, with the elongate members in the expanded configuration.
Figure 41B:
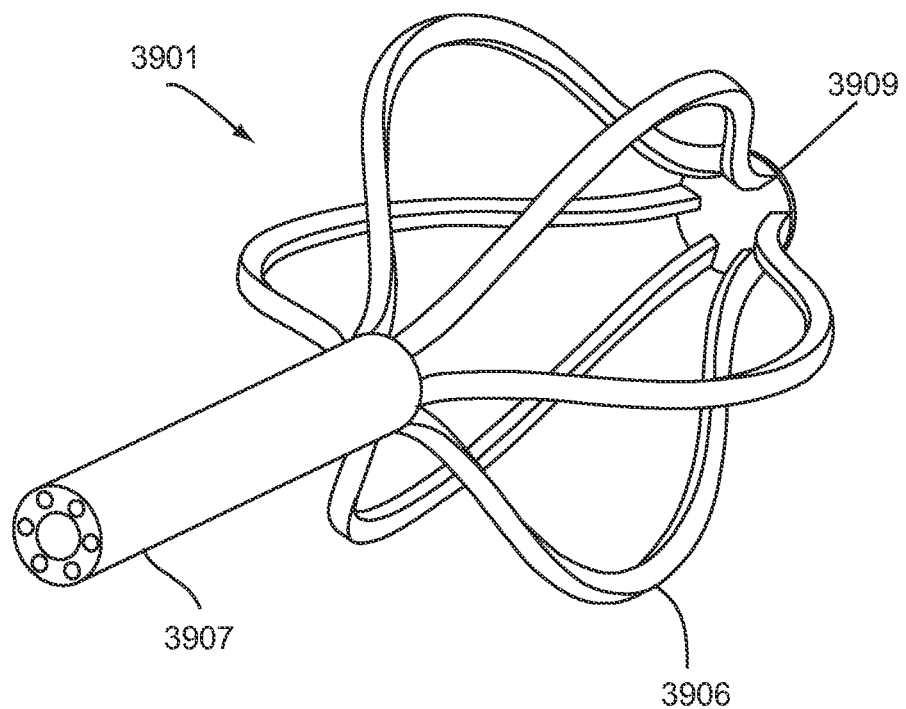
Figure 42:
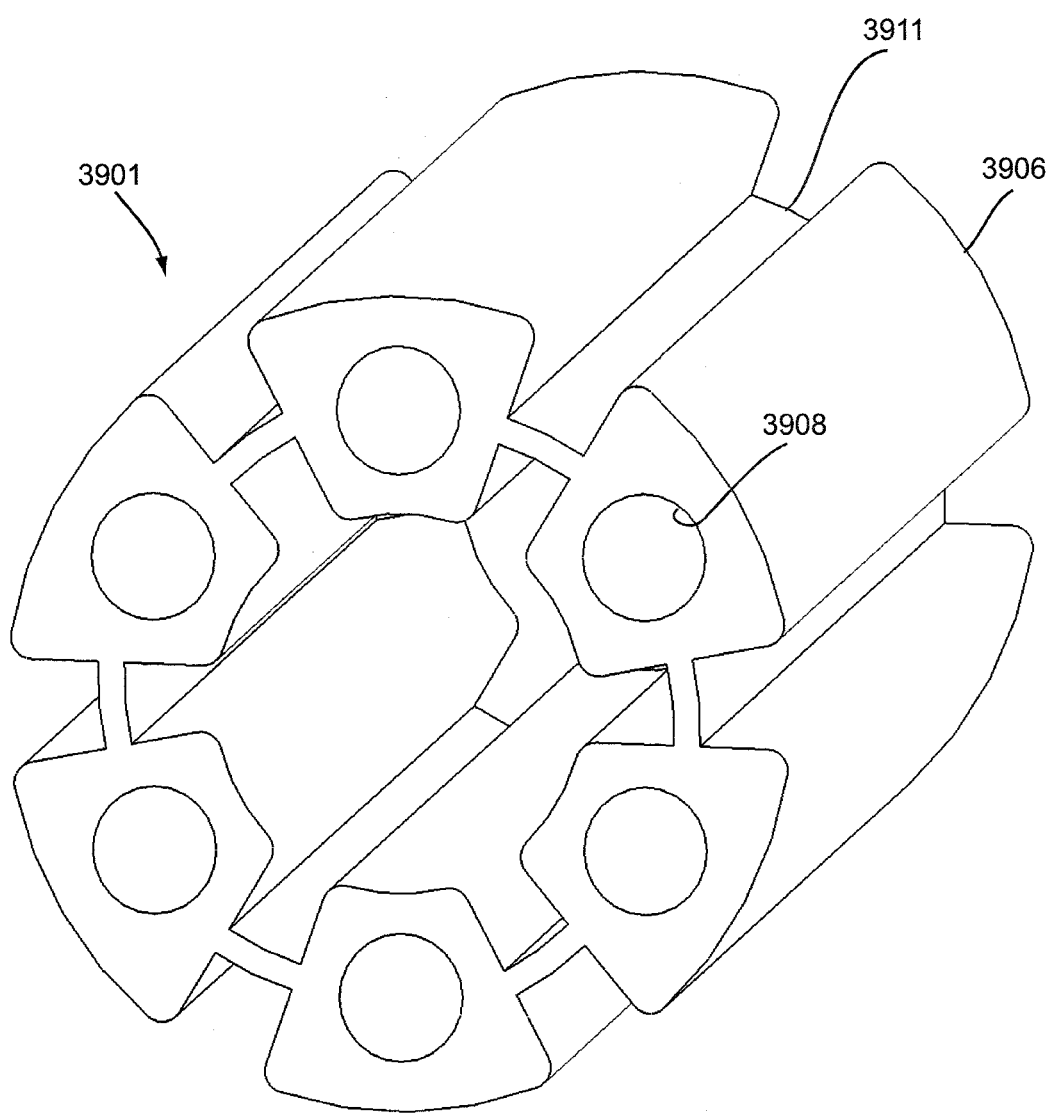
FIG. 42 is a cross-sectional detail of an extrusion that may be used to form the molded body of FIGS. 41A and 41B.

Turning to FIGS. 41A and 41B, the unitary body 3901 may be formed as an extrusion, an injection molded part, a casting and the like, e.g., including all of the features of the elongate members 3906 and proximal, and distal hubs 3907, 3909. As shown in FIG. 42, the unitary body 3901 may be formed as an extrusion with adjacent elongate members 3906 attached to one another, e.g., by relatively thin or weakened regions or webs 3911. The elongate members 3906 may include one or more lumens, e.g., lumen 3908 for receiving one or more radiation sources (not shown). In order to allow expansion of the elongate members 3906, the webs 3911 may be cut or otherwise separated, e.g., along a length of the unitary body 3901 corresponding to the elongate members 3906. Any excess web material may be trimmed, if desired, or may remain to provide lateral extensions (not shown). The webs 3911 may have a substantially uniform thickness along the portion of the unitary body 3901 defining the elongate members 3906 or may have varying thickness, e.g., to create lateral extensions or other features (not shown).

Once the webs 3911 are separated, the core member 3910 or other components of the apparatus 3900 may be attached or otherwise incorporated into the unitary body 3901. For example, if the unitary body 3901 includes additional lumens (not shown) within the elongate members 3906, stiffening members and the like (also not shown) may be inserted into the additional lumens. Optionally, a central tubular member and/or lumen (not shown) may be formed as part of the unitary body 3901 or may be attached to the unitary body 3901, e.g., similar to other embodiments described elsewhere herein.

Figure 45:
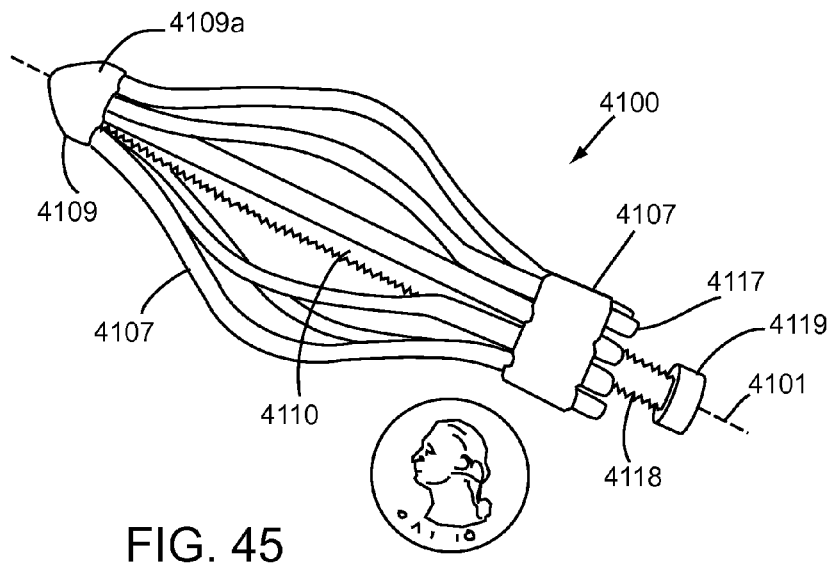
FIG. 45 is a perspective view of a thirteenth exemplary embodiment of an expandable brachytherapy apparatus in an expanded configuration and including a central lumen for receiving a radiation source.
Figure 46A:
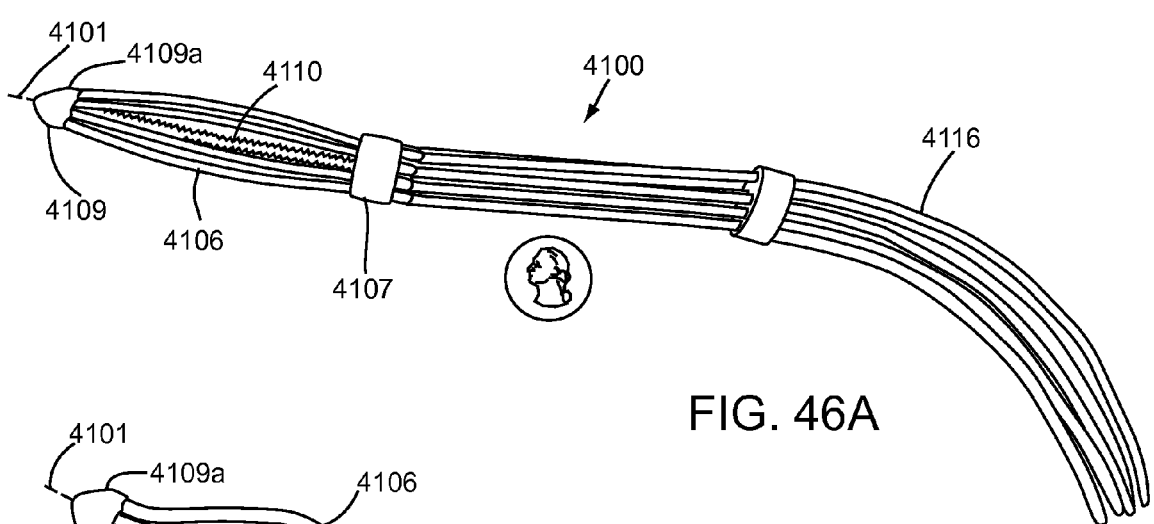
FIGS. 46A and 46B are perspective views of a fourteenth exemplary embodiment of an expandable brachytherapy apparatus including individual lumens communicating with respective all-plastic elongate members, showing the elongate members in collapsed and expanded configurations, respectively.
Figure 46B:
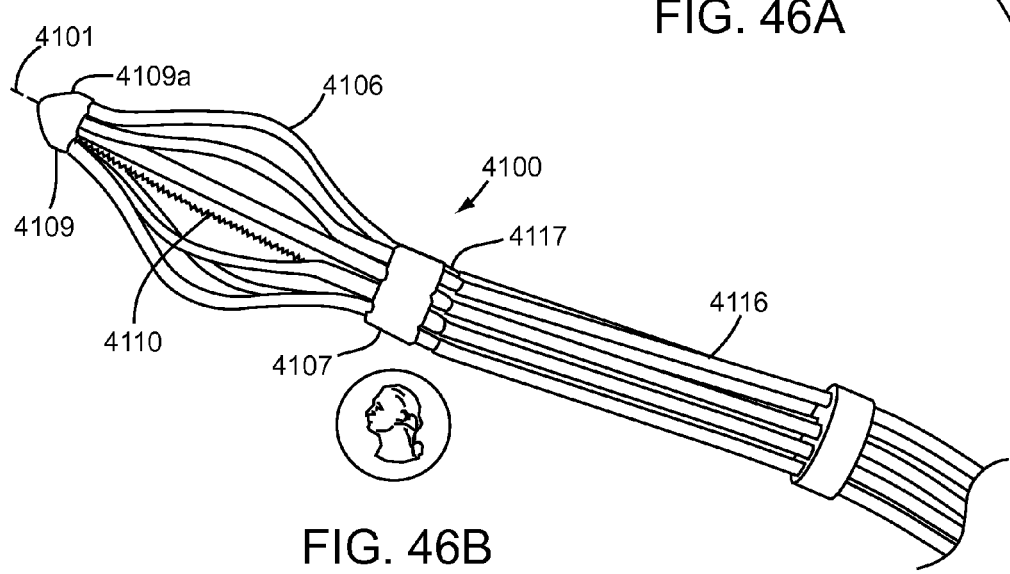

Turning to FIGS. 45-46B, additional embodiments of an expandable brachytherapy apparatus 4100 are shown that include a plurality of elongate members 4106 extending between proximal and distal hubs 4107, 4109 and a core member 4110, constructed similar to other embodiments described elsewhere herein. In addition, the apparatus 4100 includes a plurality of tubular members 4116 extending proximally from the proximal hub 4107. As best seen in FIG. 45, the proximal hub 4107 may include a plurality of nipples 4117 or other features to which respective tubular members 4116 may be attached. Thus, each tubular member 4116 may communicate with a lumen of a respective elongate member 4106, similar to previous embodiments. The tubular members 4116 may have any desired length, e.g., sufficient to provide access from outside a patient's body to a treatment site within which the elongate members 4106 are deployed.

Optionally, as shown in FIG. 45, the core member 4110 may be a hollow tube, e.g., including a lumen (not shown) that may be used as a pathway for radiation. In this option, a tubular member (not shown) may extend proximally from the proximal hub 4107 that communicates with the lumen of the core member 4110.

In addition, the apparatus 4100 may include a threaded element 4118, which may be hollow, e.g., along central axis 4101. The threaded element 4118 may be constructed similar to a rod or tube including an enlarged proximal end 4119, which may have a hexagonal inner recess or surface (not shown), which may be sized and/or shaped to receive a corresponding hexagonal end of an expansion tool (not shown), such as those described elsewhere herein.

In addition, as shown in the embodiment of FIG. 45, the individual tubular elements 4107 are flattened immediately proximal to tip 4109 and cross the central axis 4101 of the apparatus 4100 to return back to the proximal hub 4107. In this way, an array of eight radially spaced elongate members 4106 may be made from only four contiguous tubing segments. For example, each opposing pair of elongate members 4106 may include a single tubing segment that extends distally from the proximal hub 4107, through the distal end of the core member 4110, and proximally back to the proximal hub 4107. Optionally, as in the embodiment shown in FIGS. 46A and 46B, the distal hub 4109 may include a cap 4109a secured over the distal end of the core member 4110, e.g., using an interference fit, adhesive, fusing, mating threads or other connectors, and the like, thereby securing the elongate members 4106 to the distal hub 4109. Alternatively, as shown in FIG. 45, the elongate members 4106 may be fused together at their tips (e.g., using heat bonding or adhesive) and/or may include grooves or other features (not shown) for aligning the tubing segments as they cross the distal end of the core member 4110. By crossing the distal tip orthogonal to the central axis 4101 of the apparatus 4100, the elongate members 4106 may also provide an array that has a shorter tip length than if the elongate members 4106 were connected at the distal hub 4109 in an orientation substantially parallel to the central axis 4101, e.g., as shown in FIGS. 46A and 46B. This shorter tip may allow for better dosimetric conformance to the lumpectomy cavity at the distal tip of the apparatus 4100.

Turning to FIGS. 53A and 53B, an alternative embodiment of an apparatus 4100' is shown, which is generally similar to the apparatus 4100 shown in FIGS. 45-46B. Generally, the apparatus 4100' includes a plurality of elongate members 4106' and a central tubular member 4116' extending between proximal and distal hubs 4107,' 4109.' As shown, the distal hub 4109' includes a bump tip 4119,' which may be similar to the embodiment shown in FIGS. 52A and 52B. The apparatus 4100' may include tubular members or catheters 4126' extending proximally from the proximal hub 4107,' e.g., to provide a desired length, similar to the embodiment shown in FIGS. 46A and 46B.

As shown, the tubular members 4126' may be disposed around a proximal shaft 4128,' supported by a collar 4129' slidably disposed around the shaft 4128.' The collar 4129' may be used to keep the catheters 4126' organized and, during use, the collar 4129' may be slid along the catheters 4126,' e.g., to the surface of the patient's skin within which the apparatus 4100' is implanted. A suture hole (not shown) on the edge of the sliding hub may accommodate a suture, which may be passed through the patient's skin to help secure the apparatus 4100' to the patient.

Alternatively, the collar 4129' may be coupled to the tubular members 4126' such that axial movement of the collar 4129' compresses or extends the tubular members 4126,' thereby expanding and collapsing the elongate members 4106,' similar to the previous embodiments. In this embodiment, the proximal hub 4107' may be fixed relative to the shaft 4128' and the tubular members 4126' may extend through the proximal hub 4107,' such that the proximal hub 4107' remains stationary while the collar 4129' is directed axially, the tubular members 4126' moving through the proximal hub 4107' to expand and collapse the elongate members 4106.'

Figure 47B:
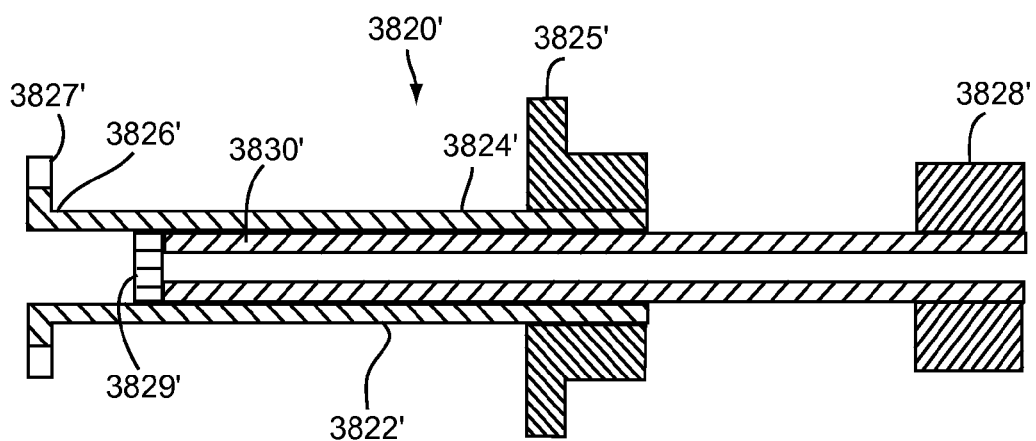
FIG. 47B is a longitudinal cross-section of the tool of FIG. 47A.
Figure 48:
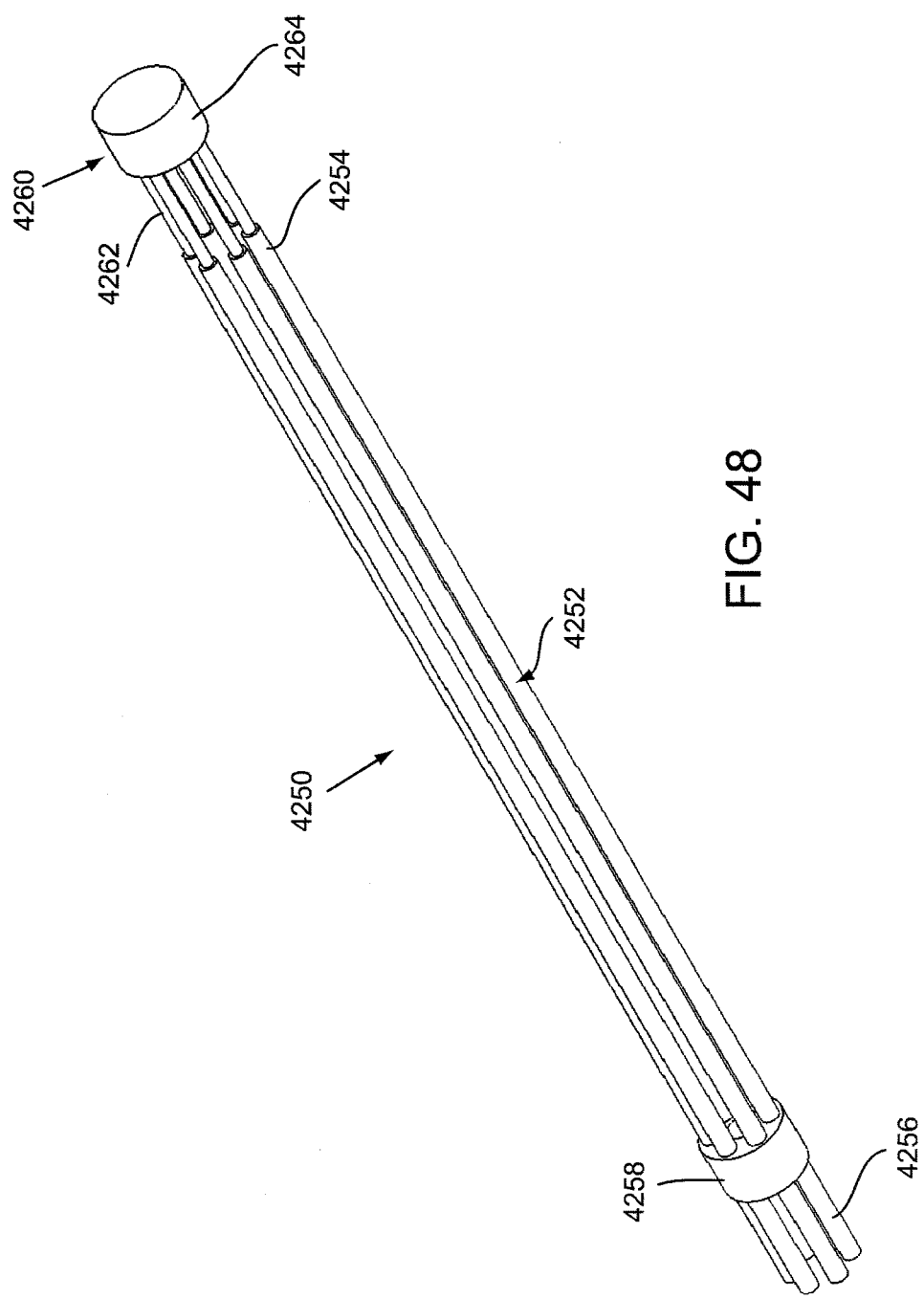
FIG. 48 is a perspective view of a cartridge for loading a plurality of radiation sources into a brachytherapy apparatus.

A pair of handles 4132,' 4134' may be permanently attached or otherwise disposed on a proximal end of the shaft 4128,' which may be rotatable relative to one another, e.g., to allow expansion and collapse of the elongate members 4106, similar to the expansion tool shown in FIGS. 39A, 39B, and 47. With the expansion tool permanently attached to the apparatus 4100,' the core member 4110' need not be rigid. For example, in some embodiments, the core member 4110' may be a flexible cable (not shown) that extends to the distal end of the apparatus 4100' to provide tension to the distal end to effect expansion of the elongate members 4106.' The cable may be a single element, welded or soldered at its distal end to the distal hub 4109' or to an extension (not shown) from the distal hub 4109.'

Alternatively, the cable may be a loop, with the cable passing through an eyelet or hole in the distal hub 4109' or extension therefrom (not shown). The proximal end(s) of the cable may be mounted with set screws (not shown) to the handle element 4134.' As long as the flexible shaft 4128' has sufficient rotational and axial stability, the mating threads used to drive the expansion and collapse of the apparatus 4100' may be located within handle elements 4132,' 4134' (not shown). Such a cable-activated apparatus may provide a lower profile in the region that enters the patient's body, e.g., because the bulk required by the set of the mating threads may be located outside the patient's body (e.g., in the expansion tool). Alternatively, the permanently attached shaft 4128' as well as the rotating elements within the shaft 4128' may be replaced with a removable expansion tool (not shown). The apparatus 4100' may be used similar to other embodiments described herein, with the elongate members 4106' and central tubular member 4116' receiving one or more radiation sources (not shown).

Turning to FIGS. 48-51, a cartridge 4250 is shown, which may be used to deliver a plurality of radiation sources, e.g., LDR pods (not shown), substantially simultaneously into an expandable brachytherapy apparatus 4200, which may be similar to any of the embodiments described herein. Generally, the cartridge 4250 includes a plurality of tubular bodies or other carriers 4252 including proximal and distal ends 4254, 4256. The carriers 4252 may be fixed relative to one another, e.g., by a collar, band, hub, and the like 4258. The distal ends 4256 may be connectable to the apparatus 4200, e.g., by slidable engagement, one or more connectors (not shown), and the like.

Figure 49:
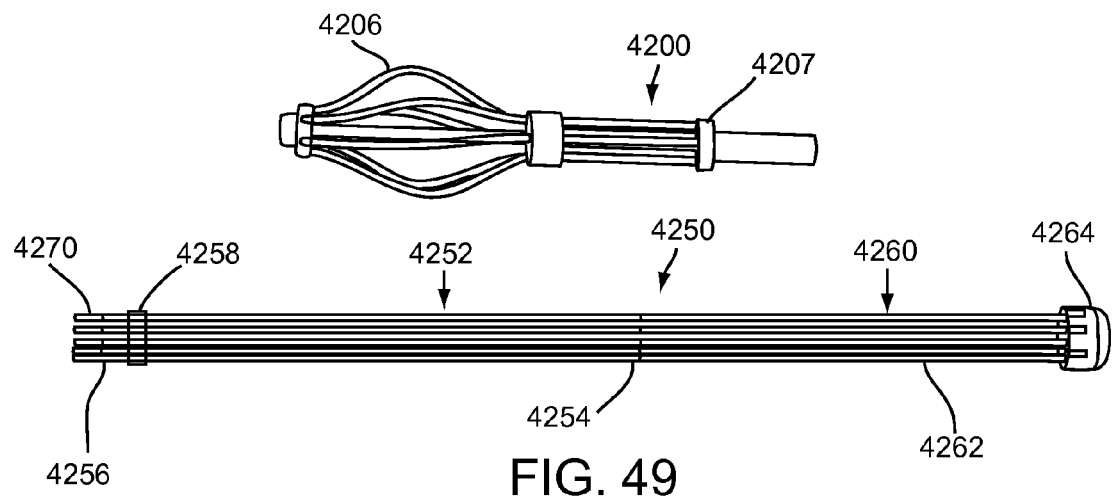
FIG. 49 is a side view of the cartridge of FIG. 48 and an exemplary embodiment of an expandable brachytherapy apparatus.

The cartridge 4250 also includes a piston assembly 4260 including a plurality of pistons 4262 that may be slidably received in respective carriers 4252. The pistons 4262 may be connected or otherwise fixed in an arrangement corresponding the arrangement of the carriers 4252, e.g., by a proximal handle 4264. The carriers 4252 may be loaded with respective radiation sources, e.g., pods 4270, the tips of which are shown in FIG. 49, and the pistons 4262 may be inserted into the carriers 4252 before or after loading.

Figure 51:
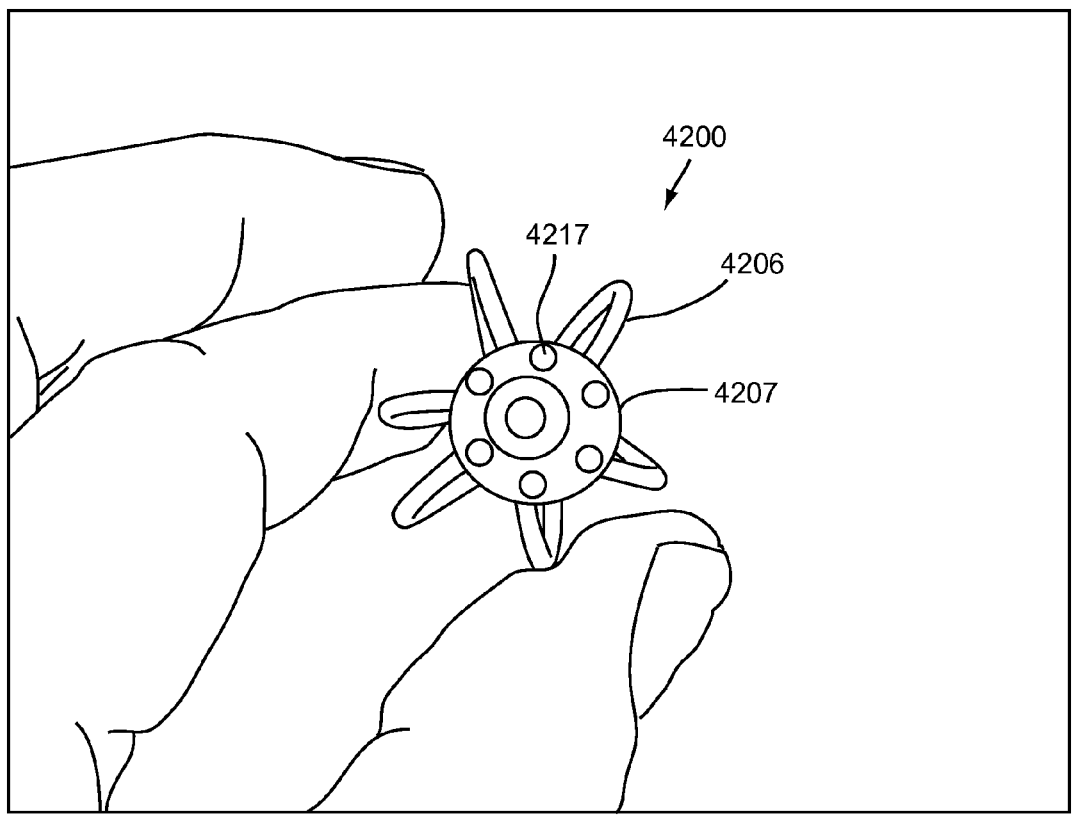
FIG. 51 is an end view of the expandable brachytherapy apparatus of FIGS. 49-50B from a proximal end of the apparatus before attaching the cartridge.
Figure 50A:
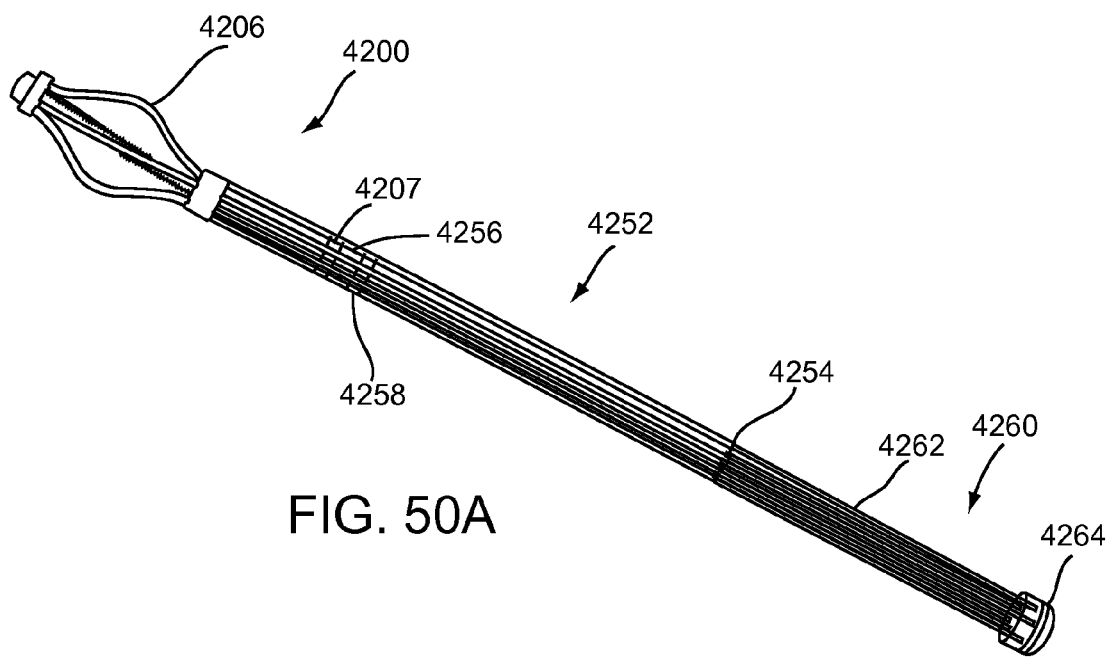
FIGS. 50A and 50B are perspective views of the cartridge and apparatus of FIG. 49, showing the cartridge being used to advance radiation sources into the apparatus.

During use, the apparatus 4200 may be implanted within a patient's body, similar to the embodiments described elsewhere herein. An expansion tool (not shown) used to expand the elongate members 4206 may be disengaged from the proximal hub 4207 or otherwise removed. Thus, the proximal hub 4207 may remain free to be connected to the cartridge 4250, as shown in FIG. 51. Turning to FIG. 50A, the distal ends 4256 of the carriers 4252 may be connected to the proximal hub 4207. For example, the distal ends 4256 may simply be slidably received over or into nipples 4217 on the proximal hub 4207. In addition or alternatively, the distal ends 4256 and/or proximal hub 4207 may include detents or other features that interlock or otherwise engage to secure the cartridge 4250 to the apparatus 4200.

Figure 50B:
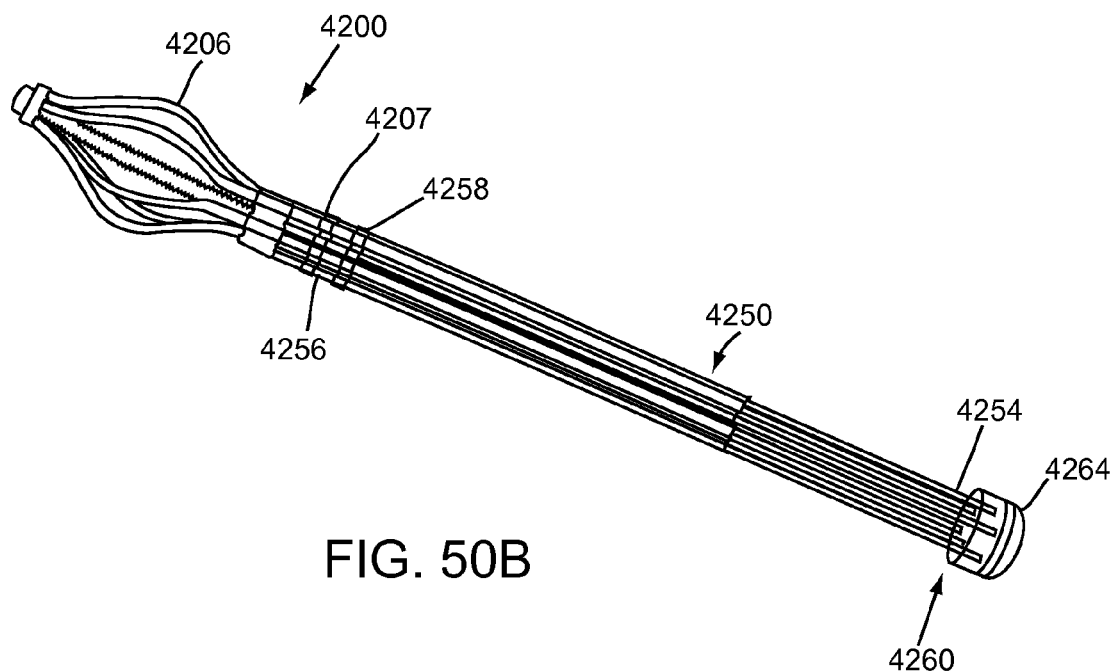

Turning to FIG. 50B, when it desired to introduce the radiation sources 4270 (not shown in FIG. 50B; see FIG. 49), the handle 4264 of the piston assembly 4260 may be depressed, i.e., pushed distally towards the apparatus 4200. This causes the pistons 4262 to be advanced distally into the respective carriers 4250 until the pistons 4262 contact and push the radiation sources distally from the carriers 4250. The radiation sources may then pass through the proximal hub 4207 and into the respective elongate members 4206. The radiation sources may then be used to deliver radiation to tissue surrounding the elongate members 4206 according to a desired dose plan.

The cartridge 4250 may be disengaged or otherwise removed from the apparatus 4200 after introducing the radiation sources. If desired, a threaded or press-fit cap (not shown) may be placed over the end of the proximal hub 4207 to further secure and protect the radiation source elements 4270 during treatment. After delivering sufficient radiation, an expansion tool (not shown) may be used to collapse the elongate members 4206 and the apparatus 4200, along with the radiation sources, may be removed from the patient's body. After sufficient radiation is delivered, the handle 4264 of the piston assembly 4260 may be pulled proximally to withdraw the radiation sources back into the carriers 4252. The cartridge 4205 may then be removed from the apparatus 4200. The apparatus 4200 may remain within the patient, e.g., for subsequent radiation treatment, or may be removed after the cartridge 4250.

The apparatus described herein may permit brachytherapy devices (or other radiation sources) to deliver radiation to tissue surrounding a cavity from a position within the cavity, e.g., via a single point of entry. Moreover, the intracavitary apparatus, methods, and systems described herein may permit substantial fixation of one or more radioactive sources relative to the target tissue surrounding the cavity. The surrounding tissue may invaginate sufficiently around the devices to ensure adequate fixation and/or sufficient depth of penetration of the desired radiation dose to the tissue adjacent the lumpectomy cavity throughout the implantation period. As a result, the desired dose delivery to specific tissue may be achieved over the course of brachytherapy treatment. Moreover, irradiation of unintended tissue, e.g., due to movement of the device relative to the surrounding tissue, may be minimized.

The brachytherapy devices described herein may be implanted into (and/or around) a tumor before surgical excision (neoadjuvantly), and then subsequently removed before or at the time of surgery. Such treatments may shrink or even destroy the tumor. In other embodiments, the apparatus and methods described herein may be used to deliver brachytherapy after surgically removing tumor tissue to treat surrounding tissue post-operatively (post-lumpectomy in breast). In some instances, it is contemplated that brachytherapy apparatus and methods described and illustrated herein may supplement or reduce the need for conventional treatment options, e.g., tumor excision, full field external beam radiation therapy (EBRT), and chemotherapy. Alternatively, the methods described herein may be performed adjuvantly with these and other treatments, e.g., with chemotherapy, EBRT.

Alternatively, the apparatus and methods described herein may be used to perform HDR treatment, e.g., by delivering one or more HDR radiation sources along pathways of the devices in accordance with known HDR dose plans. In a further alternative, a HDR radiation source (e.g., an Iridium tipped afterloader cable from Varian Medical Systems, Inc., or a small diameter x-ray source, such as those disclosed in U.S. Publication No. 2005/0061533A1, the disclosure of which is expressly incorporated by reference herein) may be advanced through any of the core members described herein, with the expandable devices opening a cavity to facilitate delivering radiation more evenly to the tissue surrounding the cavity. Optionally, the core member may shield the radiation source to direct radiation from the radiation source towards a desired portion of the surrounding tissue.

The brachytherapy devices described herein are also substantially flexible, in comparison to conventional HDR catheters, such that they may be placed in either a straight or curvilinear (e.g., curved or spiral) fashion. Such flexibility may permit implantation of radiation sources (e.g., seeds) in configurations and locations that otherwise may be considered inaccessible.

Apparatus and methods of the present invention may also potentially achieve desired dosage with relatively few catheters. For example, the apparatus and methods described herein potentially may obtain desired dose delivery levels with fewer catheters per target than is typically utilized with conventional HDR methods. Yet, the devices described herein may still be implanted with the use of conventional imaging methods (e.g. stereotactic X-ray, ultrasound, CT).

Apparatus and methods of the present invention may also provide other benefits to the patient. For example, potentially less skin damage and discomfort may result from smaller and more flexible catheter insertions. Further, the small flexible tail portions, once in their proper position, may be trimmed short, but may also be folded and taped against the skin, unlike rigid HDR catheters. Thus, the patient may have less discomfort over the course of treatment and potentially improved post-procedural cosmesis. Further, for example, apparatus and techniques in accordance with the present invention may potentially result in reduced side effects as compared to other treatments, e.g., EBRT and chemo, and may require fewer hospital visits over the course of the treatment regimen as compared to, for example, current HDR brachytherapy.

Still further, the brachytherapy delivery systems described herein may provide a standardized dose of radiation based upon lesion size. As a result, the need for extensive dose calculating and mapping systems may potentially be reduced or eliminated with certain cancers (e.g., breast).

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus for treating tissue surrounding a cavity within a body, comprising:
    an elongate body comprising a proximal end and a distal end configured for introduction into tissue; and
    a plurality of elongate members extending between the proximal end and the distal end and comprising pathways that extend from the proximal end to the distal end for receiving a source of radiation therealong, distal portions of the elongate members being movable from a collapsed configuration for introduction through a tissue tract to a target location to an expanded configuration, the distal portions of the elongate members comprising tubular bodies and lateral surfaces extending from the tubular bodies, the lateral surfaces comprising a pair of wings extending laterally from each tubular body, wherein the tubular bodies define an outer cross-sectional dimension and the wings define a substantially uniform thickness that is smaller than the outer cross-sectional dimension, wherein tips of the wings are spaced apart from adjacent elongate members in the expanded configuration, and wherein the wings extend from the tubular bodies such that each elongate member defines an outer surface extending between tips of the wings, the outer surface being substantially flat or arc-shaped and extending substantially continuously between the tips of the wings.

2. The apparatus of claim 1, wherein the wings of each tubular body are flat and lie within the same plane.

3. The apparatus of claim 1, wherein the elongate members comprise tubular extrusions having widths greater then radial depths.

4. The apparatus of claim 1, further comprising a source of radiation introduceable along the pathways for delivering radiation to the target location.

5. The apparatus of claim 1, the elongate members being spaced apart in the expanded configuration such that tissue at the target location invaginates between adjacent elongate members.

6. The apparatus of claim 1, further comprising a proximal hub coupled to proximal ends of the elongate members, the proximal hub being movable relative to the elongate body for moving the elongate members from the collapsed configuration to the expanded configuration.

7. The apparatus of claim 6, wherein the elongate body comprises a core member extending from the proximal end to the distal end and coupled to distal ends of the elongate members, and wherein the proximal hub comprises an outer member coupled to proximal ends of the elongate members, the outer member slidably disposed around the core member.

8. The apparatus of claim 7, wherein the outer member comprises passageways communicating with the pathways of the elongate members.

9. The apparatus of claim 6, wherein the proximal hub comprises a plurality of openings communicating with respective pathways for introducing the source of radiation along the pathways.

10. The apparatus of claim 6, further comprising a distal hub coupled to distal ends of the elongate members.

11. The apparatus of claim 1, wherein the distal end of the elongate body is sharpened to penetrate through tissue.

12. The apparatus of claim 1, wherein the elongate members comprise a three dimensional array in the expanded configuration that provides multiple layers of radiation sources when one or more sources of radiation are introduced into the elongate members.

13. The apparatus of claim 1, wherein the elongate members are formed entirely from non-attenuating material.

14. The apparatus of claim 13, wherein the elongate members are formed entirely from plastic.

15. The apparatus of claim 13, wherein the elongate members are non-metallic.

16. The apparatus of claim 1, the apparatus further comprising a central lumen for receiving a radiation source therein, the central lumen extending distally beyond the pathways of the elongate members, thereby allowing a radiation source to be delivered distally beyond the elongate members for delivering radiation adjacent the distal end of the elongate body.

17. The apparatus of claim 1, wherein the tubular bodies are substantially circular and wherein the outer cross-sectional dimension is an outer diameter.

18. A brachytherapy treatment apparatus for treating tissue surrounding a cavity within a body, comprising:
    an elongate body comprising a proximal end and a distal end configured for introduction into tissue; and
    a plurality of elongate members on the distal end comprising pathways for receiving a source of radiation therealong, the elongate members being movable from a collapsed configuration for introduction through a tissue tract to a target location to an expanded configuration, the elongate members comprising tubular bodies and wings extending from the tubular bodies, wherein tips of the wings are spaced apart from adjacent elongate members in the expanded configuration, wherein the tubular bodies define an outer cross-sectional dimension and the wings define a substantially uniform thickness that is smaller than the outer cross-sectional dimension,
    wherein the elongate members comprise a first inner set of elongate members expandable to define a first diameter in the expanded configuration, the apparatus further comprising a second outer set of elongate members spaced apart about a central axis of the elongate body from the first set of elongate members, the second set of elongate members expandable to define a second diameter in the expanded configuration that is greater than the first diameter.

19. The apparatus of claim 18, wherein the second set of elongate members is angularly offset from the first set of elongate members about the central axis.

20. A brachytherapy treatment apparatus for treating tissue surrounding a cavity within a body, comprising:
an elongate tubular extrusion comprising a proximal portion including a plurality of lumens, and a distal portion including a plurality of expandable elongate members formed by separating lumens of the extrusion along the distal portion, each elongate member comprising a tubular body including opposing wings and at least one of the lumens, wherein tips of the wings of each tubular body are spaced apart from tips of the wings of adjacent tubular bodies in the expanded configuration, and wherein each tubular body defines a substantially continuous outer surface extending between the tips of the wings that is substantially flat or arc-shaped,
wherein the expandable members are movable from a collapsed configuration to an expanded configuration, and wherein adjacent wings partially nest together when the expandable members are in the collapsed configuration such that adjacent wings partially overlap one another.

21. The apparatus of claim 20, wherein first ends of the elongate members extend from the proximal portion and second ends of the elongate members terminate at a distal hub formed as part of the extrusion.

22. The apparatus of claim 20, wherein the opposing wings extend from outer portions of the tubular bodies such that each elongate member defines a substantially flat outer surface extending between the tips of the wings.

23. A brachytherapy treatment apparatus for treating tissue surrounding a cavity within a body, comprising:
an elongate body comprising a proximal end and a distal end sized for introduction into tissue;
a plurality of expandable tubular members on the distal end comprising lumens for receiving a source of radiation therein, the tubular members being movable from a collapsed configuration for introduction through a tissue tract to a target location to an expanded configuration for providing a three dimensional array of pathways at the target location, at least some of the tubular members comprising a pair of wings extending laterally therefrom, the wings of each tubular member defining flat outer surfaces lying within the same plane, thereby providing an increased outer surface for the tubular members that contacts surrounding tissue when the tubular members are expanded to the expanded configuration, wherein the tubular members define an outer cross-sectional dimension and the wings define a thickness that is smaller than the outer cross-sectional dimension;
a hub coupled to proximal ends of the tubular members, the hub being movable relative to the elongate body for moving the tubular members from the collapsed configuration to the expanded configuration, wherein tips of the wings are spaced apart from adjacent tubular members in the expanded configuration; and
a plurality of tubular bodies extending proximally from the hub, the tubular bodies communicating with respective pathways of the expandable tubular members.

24. The apparatus of claim 23, further comprising an actuator for moving the hub relative to the distal end of the elongate body for moving the tubular members between the collapsed configuration and the expanded configuration.

25. The apparatus of claim 23, further comprising a plurality of pods carrying radioactive elements, the pods being introduceable into the tubular bodies such that the pods may be directed into the respective pathways of the expandable tubular members.

26. The apparatus of claim 23, the tubular members being spaced apart in the expanded configuration such that tissue at the target location invaginates between the tubular members.

27. The apparatus of claim 23, wherein the tubular bodies comprise a length that is longer than the expandable tubular members.

28. The apparatus of claim 23, wherein the tubular bodies are separable from the hub.

29. The apparatus of claim 23, wherein the wings of each tubular member comprise a pair of opposing wings extending tangentially from an outer portion of the tubular member.

30. The apparatus of claim 29, wherein adjacent wings are disposed in a side-by-side arrangement when the tubular members are in the collapsed configuration.

31. The apparatus of claim 23, wherein the wings of each tubular member define a substantially flat inner surface.

32. The apparatus of claim 23, wherein the tubular members comprise a first inner set of tubular members and a second outer set of tubular members spaced apart about a central axis of the elongate body from the first set of tubular members, the second set of tubular members defining a maximum diameter in the expanded configuration that is greater than a maximum diameter of the first set of tubular members.

33. The apparatus of claim 32, wherein each of the tubular members of the first set of tubular members comprises a pair of wings.

34. The apparatus of claim 32, wherein each of the tubular members of the second set of tubular members comprises a pair of wings.

35. The apparatus of claim 32, wherein both the first and second sets of tubular members comprise a pair of wings.

36. The apparatus of claim 23, wherein the elongate body comprises a central lumen extending from the proximal end to the distal end.

37. A brachytherapy treatment apparatus for treating tissue surrounding a cavity within a body, comprising:
an elongate body comprising a proximal end and a distal end sized for introduction into tissue;
a plurality of elongate members extending between the proximal end and the distal end and comprising pathways that extend from the proximal end to the distal end for receiving a source of radiation therealong, distal portions of the elongate members being movable from a collapsed configuration for introduction through a tissue tract to a target location to an expanded configuration for providing a three dimensional array of pathways at the target location, the elongate members being spaced apart in the expanded configuration such that tissue at the target location invaginates between adjacent elongate members; and
a pair of opposing wings extending laterally from a plurality of the elongate members for limiting or controlling invagination of tissue at the target location between the elongate members, wherein tips of the wings are spaced apart from adjacent elongate members in the expanded configuration, and wherein the opposing wings of each elongate member are flat and substantially within the same plane.

38. The apparatus of claim 37, further comprising a source of radiation introduceable along the pathways for delivering radiation to the target location.

39. The apparatus of claim 37, wherein the elongate members comprise tubular bodies, the wings extending from the tubular bodies.

40. The apparatus of claim 37, wherein the elongate members comprise tubular members and the pathways comprise lumens within the tubular members, and wherein the tubular members define an outer cross-sectional dimension and the wings define a thickness that is smaller than the outer cross-sectional dimension.

41. A brachytherapy treatment apparatus for treating tissue surrounding a cavity within a body, comprising:
an elongate body comprising a proximal end and a distal end configured for introduction into a tract through tissue, the elongate body comprising a central lumen extending from the proximal end to the distal end; and
a plurality of elongate tubular members on the distal end surrounding the elongate body distal end and comprising lumens for receiving a source of radiation therealong, the elongate tubular members being movable from a collapsed configuration for introduction through a tissue tract to a target location to an expanded configuration for providing a three dimensional array of pathways at the target location, at least some of the elongate tubular members comprising a pair of wings extending from a tubular portion defining a lumen, wherein the tubular portion defines an outer cross-sectional dimension and the wings define a thickness that is smaller than the outer cross-sectional dimension, wherein tips of the wings are spaced apart from adjacent tubular elongate members in the expanded configuration, and wherein the wings of each elongate tubular member define flat outer surfaces lying within the same plane, thereby providing an increased outer surface for the elongate tubular members that contacts surrounding tissue when the elongate tubular members are expanded to the expanded configuration,
wherein the elongate tubular members comprise a first inner set of elongate tubular members and a second outer set of elongate tubular members spaced apart about a central axis of the elongate body from the first set of elongate tubular members, the second set of elongate tubular members defining a maximum diameter in the expanded configuration that is greater than a maximum diameter of the first set of elongate tubular members.

42. The apparatus of claim 41, wherein the central lumen extends distally beyond the lumens of the elongate tubular members, thereby allowing a radiation source to be delivered distally beyond the elongate tubular members for delivering radiation adjacent the distal end of the elongate body.

43. The apparatus of claim 42, the apparatus further comprising a distal hub on the distal end of the elongate body to which distal ends of the elongate tubular members are attached.

44. The apparatus of claim 41, wherein the wings of each elongate tubular member comprise a pair of opposing wings extending tangentially from an outer portion of the tubular portion.

45. The apparatus of claim 44, wherein adjacent wings are disposed in a side-by-side arrangement when the elongate members are in the collapsed configuration.

46. The apparatus of claim 41, wherein the first set of elongate tubular members comprise tubular bodies including one or more wings and lumens defining respective lumens.

47. The apparatus of claim 41, wherein the second set of elongate tubular members comprise tubular bodies including one or more wings and lumens defining respective lumens.

48. The apparatus of claim 41, wherein both the first and second sets of elongate tubular members comprise tubular bodies including one or more wings and lumens defining respective lumens.

49. A brachytherapy treatment apparatus for treating tissue surrounding a cavity within a body, comprising:
an elongate body comprising a proximal end and a distal end configured for introduction into a tract through tissue, the elongate body comprising a central lumen extending from the proximal end to the distal end; and
a plurality of elongate members on the distal end comprising pathways for receiving a source of radiation therealong, the elongate members being movable from a collapsed configuration for introduction through a tissue tract to a target location to an expanded configuration for providing a three dimensional array of pathways at the target location, at least some of the elongate members comprising a tubular body including a pair of wings and a lumen defining the pathway, wherein tips of the wings are spaced apart from adjacent elongate members in the expanded configuration, and wherein the wings of each elongate member define outer surfaces lying within the same plane, thereby providing an increased outer surface for the elongate members that contacts surrounding tissue when the tubular members are expanded to the expanded configuration,
wherein adjacent wings partially nest together when the elongate members are in the collapsed configuration such that adjacent wings partially overlap one another.

50. A brachytherapy treatment apparatus for treating tissue surrounding a cavity within a body, comprising:
an elongate body comprising a proximal end and a distal end sized for introduction into tissue;
a plurality of expandable tubular members on the distal end comprising lumens for receiving a source of radiation therein, the tubular members being movable from a collapsed configuration for introduction through a tissue tract to a target location to an expanded configuration for providing a three dimensional array of pathways at the target location, at least some of the tubular members comprising a pair of wings extending laterally therefrom, the wings of each tubular member defining outer surfaces lying within the same plane, thereby providing an increased outer surface for the tubular members that contacts surrounding tissue when the tubular members are expanded to the expanded configuration;
a hub coupled to proximal ends of the tubular members, the hub being movable relative to the elongate body for moving the tubular members from the collapsed configuration to the expanded configuration, wherein tips of the wings are spaced apart from adjacent tubular members in the expanded configuration; and
a plurality of tubular bodies extending proximally from the hub, the tubular bodies communicating with respective pathways of the expandable tubular members,
wherein adjacent wings partially nest together when the tubular members are in the collapsed configuration such that adjacent wings partially overlap one another.

51. A brachytherapy treatment apparatus for treating tissue surrounding a cavity within a body, comprising:
an elongate body comprising a proximal end and a distal end configured for introduction into a tract through tissue, the elongate body comprising a central lumen extending from the proximal end to the distal end; and
a plurality of elongate tubular members on the distal end surrounding the elongate body distal end and comprising lumens for receiving a source of radiation therealong, the elongate tubular members being movable from a collapsed configuration for introduction through a tissue tract to a target location to an expanded configuration for providing a three dimensional array of pathways at the target location, at least some of the elongate tubular members comprising a pair of wings extending from a tubular portion defining a lumen, wherein the tubular portion defines an outer cross-sectional dimension and the wings define a thickness that is smaller than the outer cross-sectional dimension, wherein tips of the wings are spaced apart from adjacent tubular elongate members in the expanded configuration, and wherein the wings of each elongate tubular member define flat outer surfaces lying within the same plane, thereby providing an increased outer surface for the elongate tubular members that contacts surrounding tissue when the elongate tubular members are expanded to the expanded configuration, wherein the tubular portion of the tubular member is substantially circular, and wherein the outer cross-sectional dimension is an outer diameter of the tubular portion, wherein the wings of each elongate member comprise a pair of opposing wings extending opposite one another at a substantially widest location on the tubular portion.

* * * * *